United States Patent [19]
Humes et al.

[11] Patent Number: 6,124,107
[45] Date of Patent: Sep. 26, 2000

[54] ASSAY FOR MARKER OF HUMAN POLYMORPHONUCLEAR LEUKOCYTE ELASTASE ACTIVITY

[75] Inventors: John L. Humes, Berkeley Heights; Richard Allen Mumford, Red Bank; D. T. Philip Davies, Scotch Plains; Mary Ellen Dahlgren, Metuchen, all of N.J.; Joshua Schafer Boger, Concord, Mass.

[73] Assignee: Merck & Co., Inc., Rahway, N.J.

[21] Appl. No.: 08/469,141

[22] Filed: Jun. 6, 1995

Related U.S. Application Data

[63] Continuation-in-part of application No. 08/335,524, Nov. 7, 1994, abandoned, which is a continuation-in-part of application No. 08/196,663, Feb. 15, 1994, abandoned, which is a continuation of application No. 07/902,102, Jun. 22, 1994, abandoned, which is a continuation of application No. 07/674,280, Mar. 21, 1991, abandoned, which is a continuation of application No. 07/205,416, Jun. 10, 1988, abandoned.

[51] Int. Cl.$^7$ ..................................................... G01N 33/53
[52] U.S. Cl. ........................ 435/7.24; 435/7.92; 436/536; 530/329
[58] Field of Search ..................................... 435/7.24, 7.9, 435/7.92, 13, 961; 436/536, 69; 530/329–330, 388.25, 389.3

[56] References Cited

U.S. PATENT DOCUMENTS

| | | | |
|---|---|---|---|
| 3,912,805 | 10/1975 | Cayzer et al. | 435/13 |
| 4,090,846 | 5/1978 | Buck | 435/13 |
| 4,585,740 | 4/1986 | Vanderlaan | 436/537 |
| 4,654,419 | 3/1987 | Vaughn | 530/326 |
| 4,927,916 | 5/1990 | Matsueda et al. | 530/387 |
| 5,126,264 | 6/1992 | Kemp et al. | 435/252.33 |
| 5,443,965 | 8/1995 | Reyes et al. | 435/5 X |

FOREIGN PATENT DOCUMENTS

| | | |
|---|---|---|
| 0 345 906 | 12/1989 | European Pat. Off. . |
| WO 88/08134 | 4/1987 | WIPO . |

OTHER PUBLICATIONS

Sterrenberg et al., "Purification and Partial Characterization of a D–like fragment from human fibrinogen, produced by human leukocyte elastase," Biochimica et Biophysica Acta, 755 (1983) 300–306.

Addison et al., 1970, Two Site Assay of Human Groth Hormone, Horm. Metab Res 3:59–60.

Bilezikian et al., 1977, Unique Pattern of Fibrinogen Cleavage by Human Leukocyte Proteases, Blood 50:21–28.

Brower et al., 1983, Alpha–1–Antitrypsin–Human Leukocyte Elastase Complexes in Blood . . . , Blood 61:842–849.

Campbell, 1982, Human leukocyte elastase, cathepsin G, and lactoferrin: . . . , PNAS USA 79:6941–6945.

Blomback et al., 1978, A two–step fibrinogen–fibrin transition in blood coagulation, Nature 275:501–505.

Canfield et al, 1976, Reactivity of Fibrinogen and Fibrinopeptide A Containing Fibrinogen Fragments with Antisera to Fibrinopeptide A, Biochemistry 15:1203–1209.

Chen et al., 1979, Radioimmunoassay of fibrinogen–fibrin degradation products: Assay for Fragment E–related Neoantigen–Methodological Aspects, Thrombosis Research 16:601–615.

Doolittle, 1971, The Structure and Evolution of Vertebrate Fibrinogen, Annal NYAS 408:13–26.

Engvall et al., 1971, Enzyme–linked immunosorbent assay (ELISA) Quantitative Assay of Immunoglobulin G. Immunochem. 8:871–874.

Ey et al., 1978, Isolation of Pure IgG1.IgG2 and IgG2b Immunoglobulins from Mouse Serum Using Protein A–Sepharose. Immunochemistry 15:429–436.

Hammarstrom et al., 1975, Nature of the Tumor–Associated Determinants(s) of Carcinoembryonic Antigen, PNAS USA 72:1528–1532.

Harel et al., 1980, Desmosine Radioimmunoassay for Measuring Elastin Degradation in Vivo, Amer. Rev. Resp. Disease 122:769–773.

Henschen et al., 1983, Covalent Structure of Fibrinogen, Annals NYAS 408:28–43.

Janoff, 1985, Elastase in Tissue Injury, Ann. Rev. Med 36:207–216.

Janoff, 1985, Elastases and Emphysema, Am. Rev. Resp Diseases 132:417–433.

Kaplan et al., 1979, Analysis of Macrophage Surface Receptors, J. Biol Chem 254:7329–7335.

King et al., 1980, Radioimmunoassay for Desmosine, Connect. Tiss. Res. 7:263–267.

Kohler et al., 1975, Continuous cultures of fused cells secreting antibody of predefined specificity, Nature 256:495–497.

Lamer et al. 1981, Chemically synthesized peptides predetermined from the nucleotide sequence of the hepatitis B virus genome elat antibodies reactive with the native envelope protein of Dane particles, PNAS USA 78 3403–3407.

MacPherson, 1973, Soft Agar Techniques in Tissue Culture Methods and Applications, pp. 276–280.

Merrifield, 1963, Solid Phase Peptide Synthesis, J. Amer. Chem. Soc. 85:2149–2154.

Miles et al., 1968, Labelled Antibodies and Immunological Assay Systems, Nature 219:186–189.

(List continued on next page.)

*Primary Examiner*—Carol A. Spiegel
*Attorney, Agent, or Firm*—Michael D. Yablonsky; Jack L. Tribble

[57] ABSTRACT

A immunoassay based on the detection of leukocyte-elastase produced fibrinogen cleavage peptides which allows the evaluation of the potency of compounds that inhibit formation of cleavage peptides in a variety of in vitro cell biological situations is provided. The assay may be employed to detect an endogenous leukocyte-elastase produced fibrinogen cleavage peptide signal in normal human plasma and at elevated levels in cystic fibrosis plasma and in rheumatoid arthritis synovial fluid samples. The assay procedure can be a single step assay which allows for the rapid and reproducible detection of specific cleavage peptides.

8 Claims, 22 Drawing Sheets

OTHER PUBLICATIONS

Nakamura et al., 1986, in Handbook of Experimental Immunology, vol. I (D.M. Weir, ed.), pp. 27.1–27.20.

Pelham et al., 1985, Unnary Excretion of Desmosine (Elastine Cross–Links) in Subjects with PiZZ Alpha–a–Antitrypsin Deficiency a Phenotype Associated with Hereditary Predisposition to Pulmonary Emphysema, Am. Rev Resp Dis 132:821–823.

Plow, 1982, Leukocyte Elastase Release during Blood Coagulation, J. jClin. Invest. 69:564–572.

Plow et al., Immunochemical discrimination of leukocyte elastase from plasmic degradation products of fibrinogen, J. Lab. Clin. Med. 102:858–868.

Tockman et al., 1986, Determination of plasma levels of elastin–derived peptides in alpha–1 antitrypsin phenotype variants, Am. Rev. Resp. Dis. 133:A60.

Tanswell et al., 1978, Structure of antigenic determinants in the amino–terminal region of bovine fibrinogen A–alpha chain, Eur. J. Biochem. 88:565–571.

Vaitukaitis, 1981, Production of antisera with small doses of immunogen, multiple intradermal injections, in Methods in Enzymology, 73:46–52.

Van Weemen et al., 1971, Immunoassay using antigen–enzyme conjugates, FEBS Letters 15:232–236.

Weitz et al., 1986, Development of an assay for in vivo human neutrophil elastase activity, J. Clin. Invest. 78:155–162.

Abboud et al., 1983, Comparison of in vitro neutrophil elastase release in nonsmokers and smokers, Am. Rev. Resp. Dis. 128:507–510.

Wallin et al. 1967, Development of a specific radioimmunoassay for determination of peptides derived from human leukocyte elastase degradation of human fibrinogen, XIth Intl Cong Thromb Haem 58 301, Abstract 1100.

Eckhardt et al, 1987, Measurement of elastase–induced fibrinogen–derived peptides in vitro, XIth Intl. Cong. Thromb. Haem. 58:104, Abstract 366.

Schiefers–Borchel, 1985, Discrimination between fibrin and fibrinogen by a monoclonal antibody against a synthetic peptide, PNAS USA 82:7091–7095.

Bodansky, 1984 "Principles of Peptide Synthesis", Springer–Verlag, pp 255–6.

Dewey, et al., "Purification and Characterization by Fast–atom–bombardment mass spectrometry . . . ", Biochem. J., vol. 281, pp. 519–524 (1992).

42 kDa ►

FGN
FGN Digest

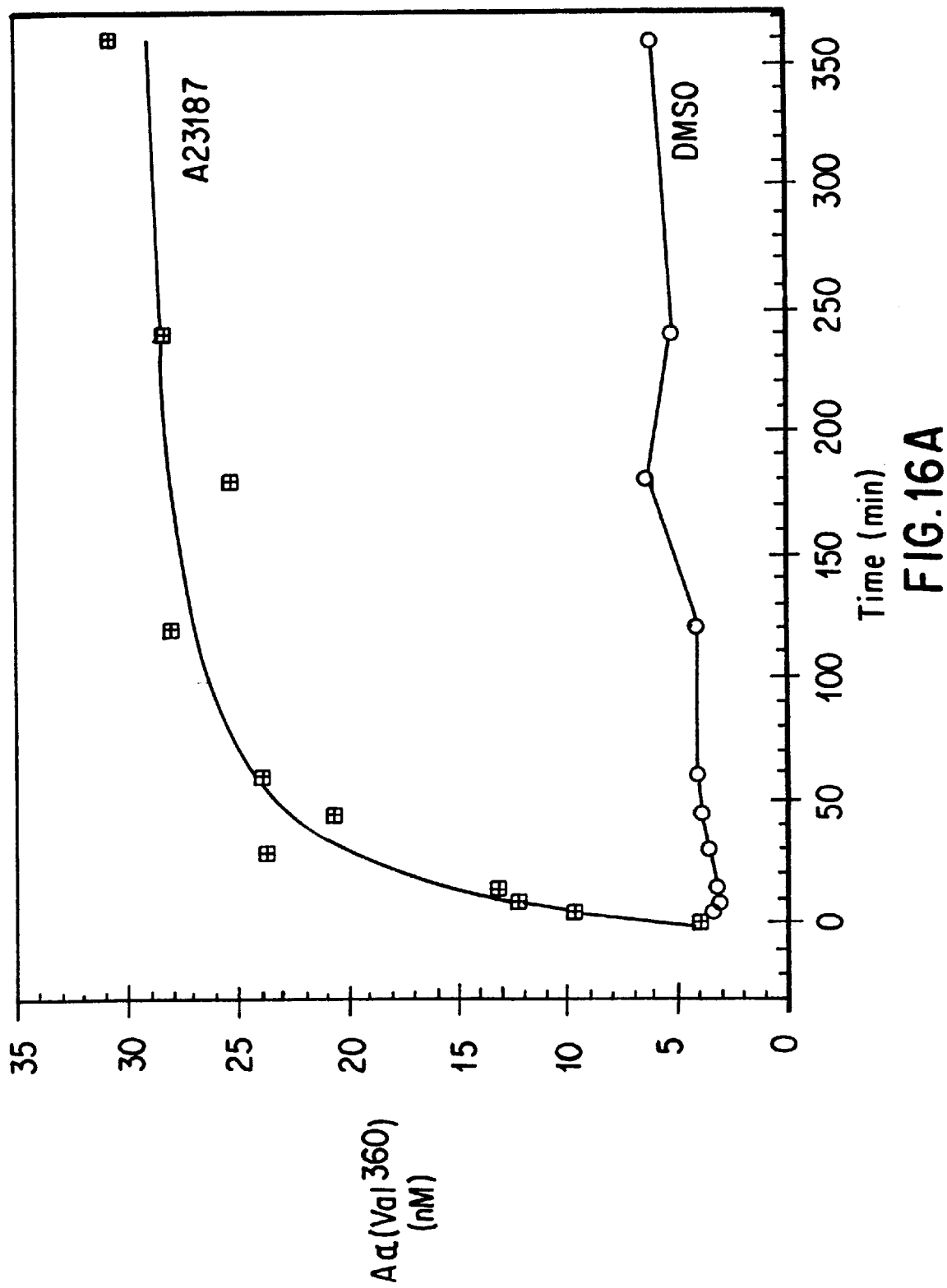

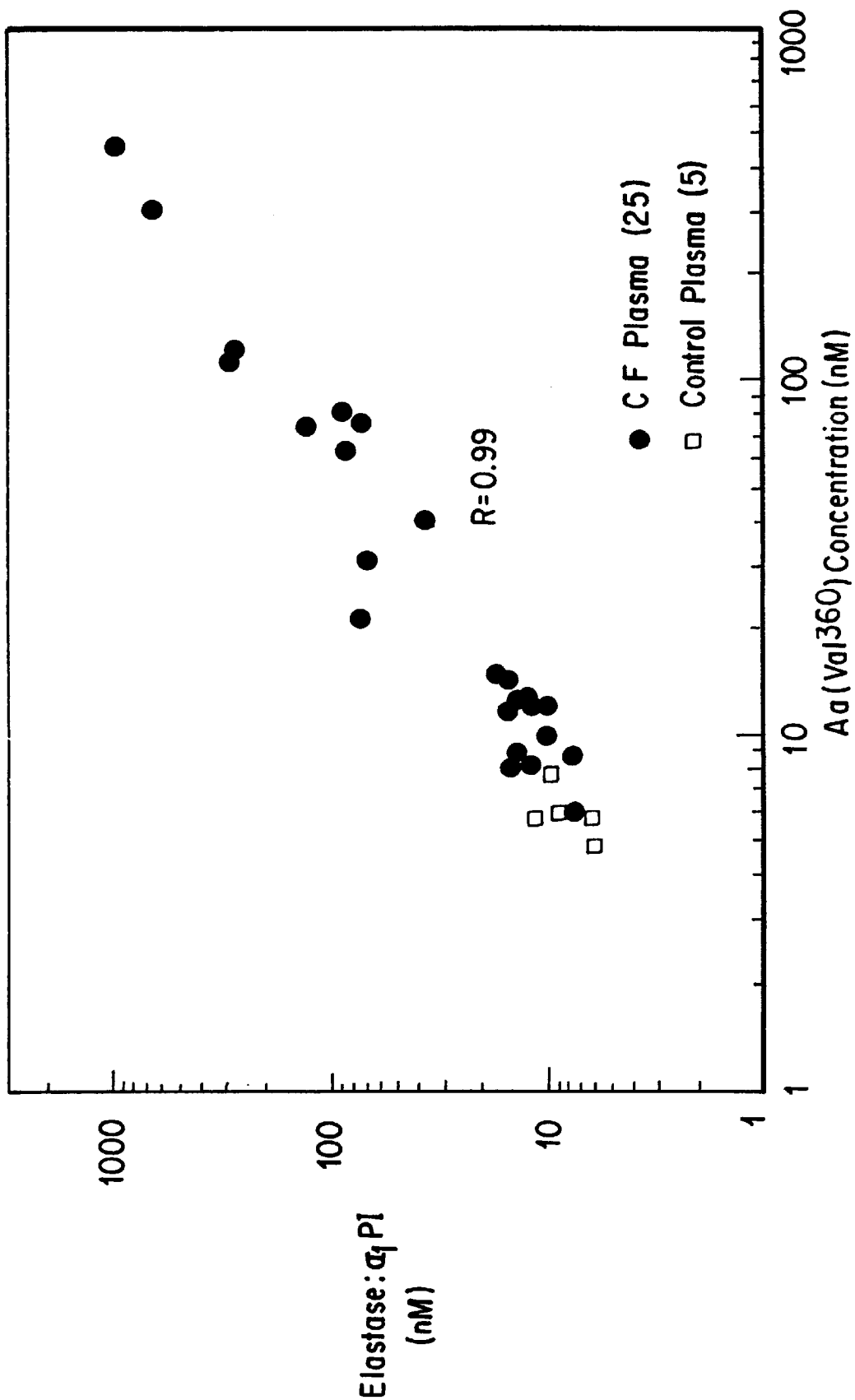

| Incubation Conditions | Plasma Aα (Val 360) nM Concentrations | | | |
|---|---|---|---|---|
| | Found (nM) | Corrected (nM) | Expected (nM) | % Recovery |
| Blood (1 ml) | Plasma/EDTA 3.7 | 0 | — | — |
| Blood + FD (9.7 pmoles) | Plasma/EDTA 20.9 | 17.2 | 15.9 | 108 |
| Blood + sp (20 pmoles) | Plasma/EDTA 4.2 | 0.5 | 32.7 | 2 |
| Blood (1 ml) + EDTA | Plasma 3.9 | 0 | — | — |
| Blood + EDTA + FD (9.7 pmoles) | Plasma 19.7 | 15.8 | 15.9 | 99 |
| Blood + EDTA + SP (20 pmoles) | Plasma 26.6 | 22.7 | 32.7 | 69 |

FIG. 21

| DONOR NUMBER (VENOUS BLOOD) | Aα(Val360) (nM) | DONOR NUMBER (ARTERIAL BLOOD) | Aα(Val360) (nM) |
|---|---|---|---|
| 1 | 3.5 | 1 | 4.8 |
| 2 | 2.8 | 2 | 5.8 |
| 3 | 2.6 | 3 | 6.0 |
| 4 | 4.7 | 4 | 5.8 |
| 4 | 3.4 | 5 | 7.9 |
| 4 | 6.1 | 6 | 4.8 |
| 5 | 5.2 | 7 | 5.8 |
| 6 | 5.0 | 8 | 6.0 |
| 6 | 3.0 | 9 | 5.8 |
| 7 | 7.3 | 10 | 7.9 |
| 8 | 5.0 | | |
| 9 | 2.5 | | |
| 10 | 3.9 | | |
| MEAN ± SD | 4.2 ± 1.5 (N=13) | MEAN ± SD | 6.1 ± 1.1 (N=10) |

FIG.22

| Date | Donor | PMN x10⁶/ml | Aα(Val360) DMSO pmoles/ml | Aα(Val360) A23187 pmoles/ml | Aα(Val360) DMSO pmoles/1x10⁶ PMN | Aα(Val360) A23187 pmoles/1x10⁶ PMN | Recovery % |
|---|---|---|---|---|---|---|---|
| 5-17-94 | 1(M) | 4.7 | 5.1 | 66.1 | 1.1 | 14.1 | 101 |
| 7-29-94 | 1(M) | 4.1 | 4.2 | 52.8 | 1.0 | 12.9 | 133 |
| 3-29-93 | 4(M) | 2.6 | 6.3 | 36.8 | 2.4 | 14.1 | 74 |
| 4-25-94 | 4(M) | 2.4 | 4.7 | 32.8 | 2.0 | 13.6 | 78 |
| 6-22-94 | 4(M) | 2.9 | 4.6 | 38.3 | 1.6 | 13.2 | 108 |
| 3-22-94 | 5(M) | 2.8 | 6.9 | 39.1 | 2.4 | 14.0 | 88 |
| 6-08-94 | 6(M) | 2.6 | 3.5 | 40.7 | 1.3 | 15.6 | 121 |
| 5-12-94 | 8(M) | 2.4 | 3.0 | 17.6 | 1.3 | 7.3 | 106 |
| 5-18-94 | 9(F) | 3.5 | 4.0 | 16.8 | 1.2 | 4.8 | 102 |
| 6-22-94 | 10(M) | 2.9 | 4.1 | 18.2 | 1.4 | 6.3 | 71 |
| 6-22-94 | 11(M) | 2.8 | 4.5 | 24.1 | 1.6 | 8.6 | 91 |
| 7-21-94 | 12(M) | 2.9 | 2.9 | 23.1 | 1.0 | 8.0 | 132 |
| MEAN ± SD | | 3.1 ± 0.7 | 4.5 ± 1.2 | 33.9 ± 15.1 | 1.5 ± 0.5 | 11.0 ± 3.7 | 100 ± 21 |

| NUMBER OF SAMPLES | | | Aα(Val³⁶⁰) | |
|---|---|---|---|---|
| | TESTED | POSITIVE | MEAN nM | RANGE |
| Rheumatoid Arthritis | 17 | 17 | 47 | 7-112 |
| Gout | 5 | 4 | 58 | 0-146 |
| Osteoarthritis | 4 | 0 | 0 | — |

ASSAY FOR MARKER OF HUMAN POLYMORPHONUCLEAR LEUKOCYTE ELASTASE ACTIVITY

CROSS-RELATED TO OTHER APPLICATIONS

This is a continuation in part of U.S. Ser. No. 08/335,524, filed Nov. 07, 1994, abandoned, which is a continuation in part of U.S. Ser. No. 08/196,663, filed Feb. 15, 1994, abandoned; which is a continuation of U.S. Ser. No. 07/902,102, filed Jun. 22, 1992; abandoned, which is a continuation of U.S. Ser. No. 07/674,280, filed Mar. 21, 1991, abandoned; which is a continuation of U.S. Ser. No. 07/205,416, filed Jun. 10, 1988, abandoned; all of which are expressly incorporated herein by reference in their entirety.

BACKGROUND OF THE INVENTION

Human polymorphonuclear leukocyte elastase (PMNE) cleaves human fibrinogen at multiple sites. Cleavage of the A$\alpha$ chain at A$\alpha$(Val$^{360}$–Ser$^{361}$) generates a stable product as indicated by its presence in biological fluids. A radioimmunoassay (RIA) based on the A$\alpha$(Val$^{360}$) epitope of this cleavage site has been developed which allows the evaluation of the potency of elastase inhibitors to inhibit formation of cleavage products containing this neoepitope in a variety of in vitro cell biological situations. The RIA detects an endogenous A$\alpha$(Val$^{360}$) in normal human plasma and at elevated concentrations in cystic fibrosis plasma and in rheumatoid arthritis synovial fluid samples.

Human leukocyte proteinases, elastase in particular, have been implicated in the pathogenesis of various connective tissue destructive diseases including pulmonary emphysema, chronic bronchitis, cystic fibrosis, bronchiectasis, acute respiratory distress syndrome, arthritis, glomerulonephritis, psoriasis, vasculitis and atherosclerosis. Elastase may also be involved in other lung diseases such as PiZZ emphysema and infantile respiratory distress syndrome and in myelogenous leukemia and gout. Elastase, a serine proteinase active at neutral pH, is stored in the azurophilic granules of polymorphonuclear leukocytes and in lysosomes of transient mononuclear leukocytes. Elastase as used herein is defined as elastase derived from leukocytes. Leukocyte as used herein includes neutrophils, macrophages and monocytes. Cellular elastase is released in tissues when the cell encounters matter (such as a pathogen) to be phagocytized or undergoes cellular autolysis. Tissue pathology occurs when the released elastase encounters endogenous connective tissue substrates such as elastin, proteoglycan, types III and IV collagen and fibrinonectin. In addition to connective tissue components, human leukocyte elastase hydrolyzes various plasma proteins including immunoglobulins, fibrin, fibrinogen and complement proteins.

Extracellular PMNE activity is controlled by circulating or locally produced elastase inhibitors. Circulating elastase inhibitors include alpha-1-proteinase inhibitor and alpha-2-macroglobulin. Alpha-1-proteinase inhibitor is the most prevalent regulator of endogenous elastase activity and blocks enzyme activity by complexing with the elastase so that it is unable to act on other substrates. The enzyme-inhibitor complexes are then cleared from the tissues and circulation.

Elastase and the other leukocyte associated proteinases have also been implicated in the alternate fibrinolytic pathway responsible for the dissolution of fibrinogen and fibrin. The fibrinolytic activity may be physiologically important in the thrombi reduction but may also lead to pathological conditions related to blood coagulation.

A thorough understanding of the role of leukocyte elastase in both physiological and pathological states has been hampered by the absence of a quick, efficient and reliable assay for detecting enzymatic activity in vivo with a natural substrate such as human fibrinogen. Direct measurement of the enzymatic activity of released PMNE is difficult because the released enzyme rapidly binds to the substrate or to serum proteinase inhibitors. Bound enzyme may be quickly removed from the circulation. Immunoassay determinations of released enzyme do not distinguish between free enzyme and enzyme bound to inhibitor, and determinations of enzyme-inhibitor complexes have the disadvantage that they detect only the inactivated enzyme.

Since direct detection of enzymatically active PMNE in physiological fluids has not proven reliable, alternate assay procedures dependent upon the detection of PMNE cleavage products have been designed. Two of these methods have used elastase-cleaved products of elastin as markers. One method measured urinary desmosine, a major cross-linking amino acid of elastin, by radioimmunoassay. No consistent difference has been observed between healthy individuals and chronic lung disease patients. A similar result has been reported using ELISA measurements of elastase-generated elastin-derived peptides in serum of lung disease patients and normal controls.

Assays designed to detect plasmin-generated fibrinogen degradation products (FDP) have been used to detect fibrinogen cleavage products. Early assays utilized antibodies reactive with human FDP prepared by human plasmin digestion of human fibrinogen at room temperature for 12 to 36 hours, U.S. Pat. No. 3,912,805. The antibodies are attached to red blood cells and are used in passive agglutination assays to detect FDP. Antibodies to purified FDP fragments such as fragments D and E have also been employed to identify and quantify fibrinogen degradation products, U.S. Pat. No. 4,090,846. The assay consisted of an indirect method in which human serum or urine were mixed with the antiserum to the purified D and E fragments, to which was added FDP bound to latex beads. Other fibrinogen fragments have been used to produce antibody that can be used to detect the fragments in blood. Plasminogen derived fragments such as Fg-E have been described by Chen and Schulof, Thrombos. Res. 16: 601–615 (1979) and antibodies to the fragment have been used in radioimmunoassay to detect the fragment in plasma.

Fibrinogen degradation products prepared by digesting human fibrinogen with PMNE have been used to develop assays for evaluating elastase cleavage products in fluids. Human fibrinogen was digested with PMNE at 1:50 (w/w) enzyme-to-substrate ratio for 24 hrs. at 37° C. The predominant fragment was a D-like fragment of 80,000 MW and designated $D_e$. Antibody to this fragment retained its capacity to recognize the $D_e$ in radioimmunoassays after adsorption with intact fibrinogen and plasmin degradation products. Plow et al. suggested that this indicated the recognition of an elastase-elicited neoantigen that was only expressed by elastase degradation products. When elastase degradation products were added to normal plasma, the elastase-elicited neoantigen could be quantitatively detected in radioimmunoassay. The principal disadvantage of the fibrinogen degradation product assay procedures is that the material being assayed is defined only operationally. The sites of PMNE (or plasmin) cleavage have not been adequately defined. Consequently, the specificity of the antisera cannot be rigorously investigated and the exact nature of the products measured in the immunoassay is unknown.

Immunoassays designed to detect products of thrombin cleavage of fibrinogen have been described in several animal species. For example, a radioimmunoassay has been described which identifies the peptide F-CB1α from the amino end of bovine fibrinogen Aα chain. Thrombin cleavage of F-CB1 yielded two fragments: fibrinopeptide A (residues Aα1–16; residues 1–19; equivalent to human residues 1–16) and the carboxy-terminal fragment Th2 (residues 20–54; equal to human residues 17–51).

Fibrinopeptide A (FPA), the 1–16 amino acid residue of the Aα chain (Aα 1–16), is released by thrombin cleavage and have been used to produce antibodies which can be employed to assay for the fibrinogen cleavage product FPA. Antibodies reactive with FPA were used to study the human elastase cleavage products of human fibrinogen. It was found that the elastase degradation products were different from the thrombin degradation products as determined by radioimmunoassays specific for FPA. The elastase cleavage product was slightly larger than FPA and could be distinguished from FPA by immunological means.

Antibody specifically reactive with FPA has been used to evaluate in vivo human leukocyte elastase activity. Weitz et al. found that leukocyte elastase cleaves fibrinogen into a fibrinopeptide A-containing fragment which can be used as an index of elastase activity. Human leukocyte elastase cleaves a 21 amino acid peptide, fibrinogen Aα 1–21 from the amino terminus of the alpha chain of human fibrinogen. This Aα 1–21 peptide contains the entire FPA peptide. The Weitz assay does not directly measure the elastase cleavage product, but measures FPA, Aα 1–16, which is the normal human thrombin cleavage product of human fibrinogen. The Weitz two step radioimmunoassay utilized fresh human plasma, ethanol treated, presumably totally fibrinogen depleted, either treated or untreated with human thrombin. The difference in immunoreactive FPA, Aα 1–6, between the thrombin treated and untreated samples is attributed to the amount of Aα 1–21 present in the original sample. This assay does not directly measure an elastase cleavage product in body fluids and requires a two-step process to detect what appears to be a single elastase cleavage product.

The development of assays to determine the biochemical efficacy and potency of elastase inhibitors has evolved around the need to measure the activity of PMNE under a variety of circumstances in man. The evaluation of the extracellular activity of PMNE in both physiological and pathological states has been hampered by the lack of a specific assay to detect its activity in vivo. The direct measurement of the enzymatic activity of extracellular PMNE is difficult because the released enzyme binds to substrates and to plasma proteinase inhibitors almost immediately upon its release from PMN. Detection of enzyme by immunoassays does not distinguish between free enzyme and enzyme bound to inhibitors; the disadvantage of immunoassays that measure levels of enzyme inhibitors is that they detect only the inactivated enzyme.

Human fibrinogen is a hetero-dimeric glycoprotein consisting of 3 non-identical chains, Aα, Bβ and γ. PMNE cleaves human fibrinogen at multiple sites. Primary sites of cleavage include Aα(Val$^{21}$–Glu$^{22}$), Aα(Val$^{360}$–Ser$^{361}$), Aα(Val$^{450}$–Ile$^{451}$), Aα(Val$^{464}$–Thr$^{465}$), Aα(Met$^{476}$–Asp$^{477}$), Aα(Thr$^{568}$–Ser$^{569}$), γ(Thr$^{305}$–Ser$^{306}$), γ(Val$^{347}$–Tyr$^{348}$) and γ(Ala$^{357}$–Ser$^{358}$). We have developed two anti-peptide antibodies, one of which specifically measures PMNE hydrolysis of fibrinogen at the Aα(Val$^{21}$–Glu$^{22}$) position to release a 21 residue N-terminal peptide, and a second which measures cleavage at Aα(Val$^{360}$–Ser$^{361}$), to release a 250 residue C-terminal fragment (FIG. 1). The Aα(Val$^{360}$) carboxyl terminal fragment remains associated with the β and γ chains of fibrinogen due to the disulfide network of the protein. Neither of the 2 specific antisera recognize intact fibrinogen. Both of these RIA allow the evaluation of the potency of PMNE inhibitors, such as elastase inhibitors, to inhibit fibrinopeptide neoepitope generation in whole blood stimulated with the calcium ionophore A23187. However, a major disadvantage of the Aα(Val$^{21}$) assay is the rapid in vivo clearance and metabolism of the peptide neoepitope Aα(Val$^{21}$) ($t_{1/2}$ of 30 sec in both the dog and rhesus monkey). In an extensive series of experiments we were unable to detect the Aα(Val$^{21}$) neoepitope in normal human plasma or in plasma samples from PiZZ individuals, nor in plasma from from patients with cystic fibrosis, emphysema or chronic bronchitis.

The Aα(Val$^{360}$) neoepitope is associated with a large protein fragment which results in a substantially slower clearance rate than Aα(Val$^{21}$) peptide. Utilizing the Aα(Val$^{360}$) RIA an endogenous signal is detected in normal human plasma. This signal is elevated in cystic fibrosis plasma samples. In addition, levels of Aα(Val$^{360}$) neoepitope are elevated in both rheumatoid arthritis and gout synovial fluid but not in osteoarthritis synovial fluid.

This assay may be readily incorporated into a diagnostic kit for measuring PMNE activity in man. The assay measures the potency of elastase inhibitors in plasma, sputum and synovial fluid following oral administration of drug. In a Phase 1 clinical study with elastase inhibitors, the Aα(Val$^{360}$) RIA in combination with assays of AAPVase activity and L-740,447 formation in blood, would provide data indicating the extent of inhibition of enzyme activity within cells (AAPVase in isolated PMN), generation of PMNE:elastase inhibitor complexes (L-740,447 assay) in whole blood and upon its release from cells to act on extracellular substrate [Aα(Val$^{360}$) neoepitope]. In subsequent clinical studies in cystic fibrosis patients, lowering of elevated levels of Aα(Val$^{360}$) would provide direct evidence of inhibition of PMNE activity.

The present invention is a radioimmunoassay (RIA) based on the Aα(Val$^{360}$) epitope which allows the evaluation of the potency of elastase inhibitors to inhibit formation of cleavage products containing this neoepitope in a variety of in vitro cell biological situations. This new RIA detects an endogenous Aα(Val$^{360}$) signal in normal human plasma and at elevated levels in cystic fibrosis plasma and in rheumatoid arthritis synovial fluid samples. The assay procedure is a single step assay which allows for the rapid and reproducible detection of a PMNE-specific cleavage peptide.

SUMMARY OF THE INVENTION

The present invention is a radioimmunoassay based on the Aα(Val$^{360}$) epitope which allows the evaluation of the potency of elastase inhibitors to inhibit formation of cleavage products containing this neoepitope in a variety of in vitro cell biological situations. This new RIA detects an endogenous Aα(Val$^{360}$) normal human plasma and elevated levels of Aα(Val$^{360}$) in cystic fibrosis plasma and in rheumatoid arthritis synovial fluid samples. This RIA can monitor the severity of disease and evaluate the efficacy of PMNE inhibitors in vivo. The assay procedure is a single step assay which allows for the rapid and reproducible detection of PMNE-specific cleavage peptide.

YRGSAGHATSESSV (SEQ. ID. NO:2) probe-peptide. The antibody-bound radioactivity was separated from the unbound radioactivity and the percent bound in the presence of standard peptide was calculated relative to the amount bound in the absence of competitive peptide. Only unknown sample values falling between 20–80% were used for calculations.

Figure 2:
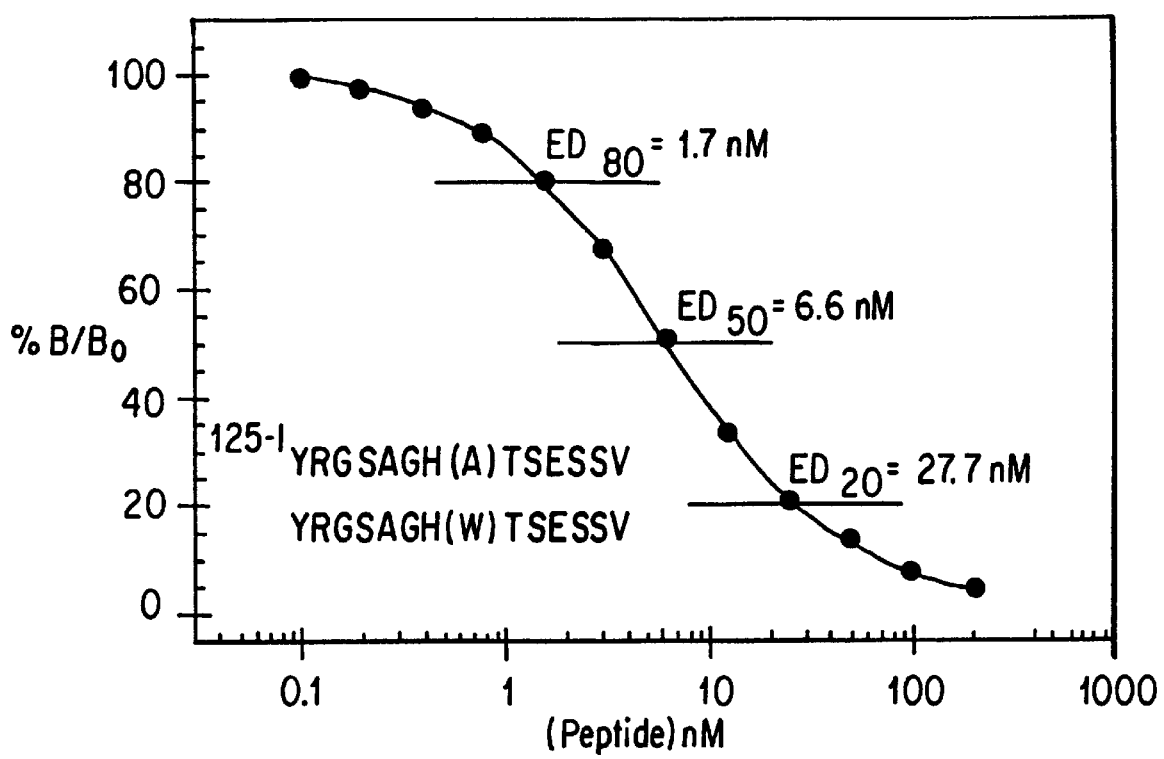

FIG. 2. The standard pepeide (YRGSAGHWTSESSV) (SEQ ID NO:1) was incubated overnight with antiserum and 125I-YRGSAGHATSESSV (SEQ ID NO:2) probe-peptide as described in Materials and Methods. The antibody bound radioactivity was separated from unbound radioactivity and the percent bound in the presence of the standard peptide was calculated relative to the amount bound in the absence of competitive peptide. Only unknown sample values falling between 20–80% were used for calculations.

Figure 3A:
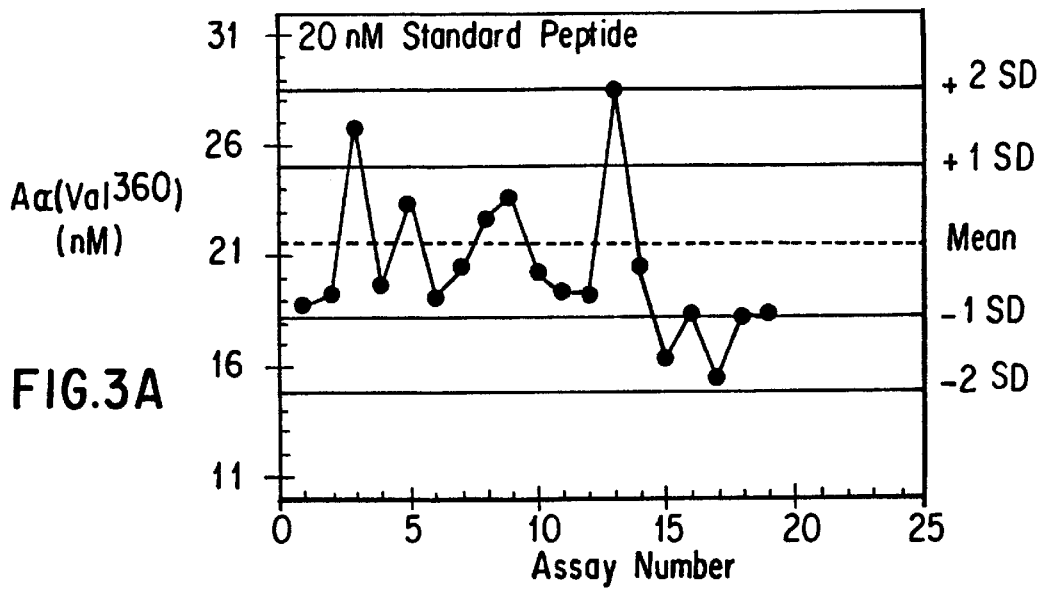
Figure 3B:
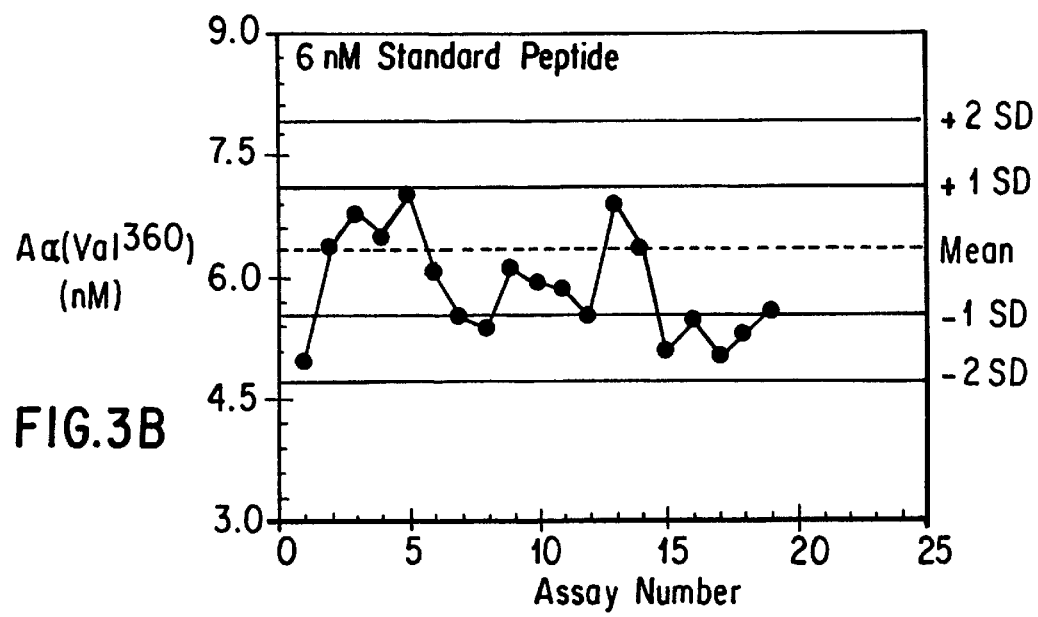
Figure 3C:
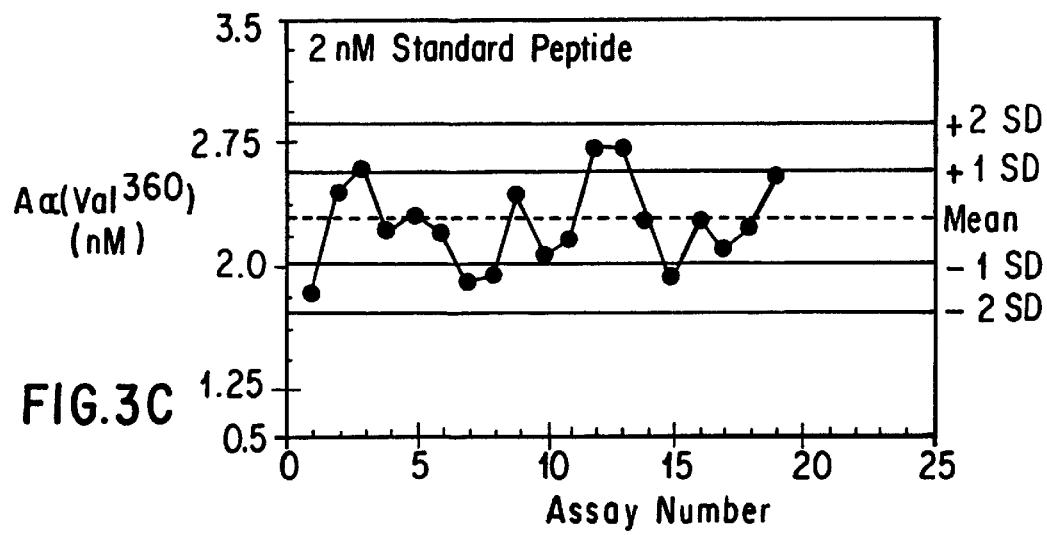

FIG. 3 shows variation of quality control standards in the A$\alpha$(Val$^{360}$) RIA.

Standard peptide solutions (20, 6 and 2 nM) were incubated in each assay to determine the variation of the RIA. The amount recovered was determined from the standard curve each day. Assays in which the standards fell outside the 2 SD limit were omitted.

Figure 4:
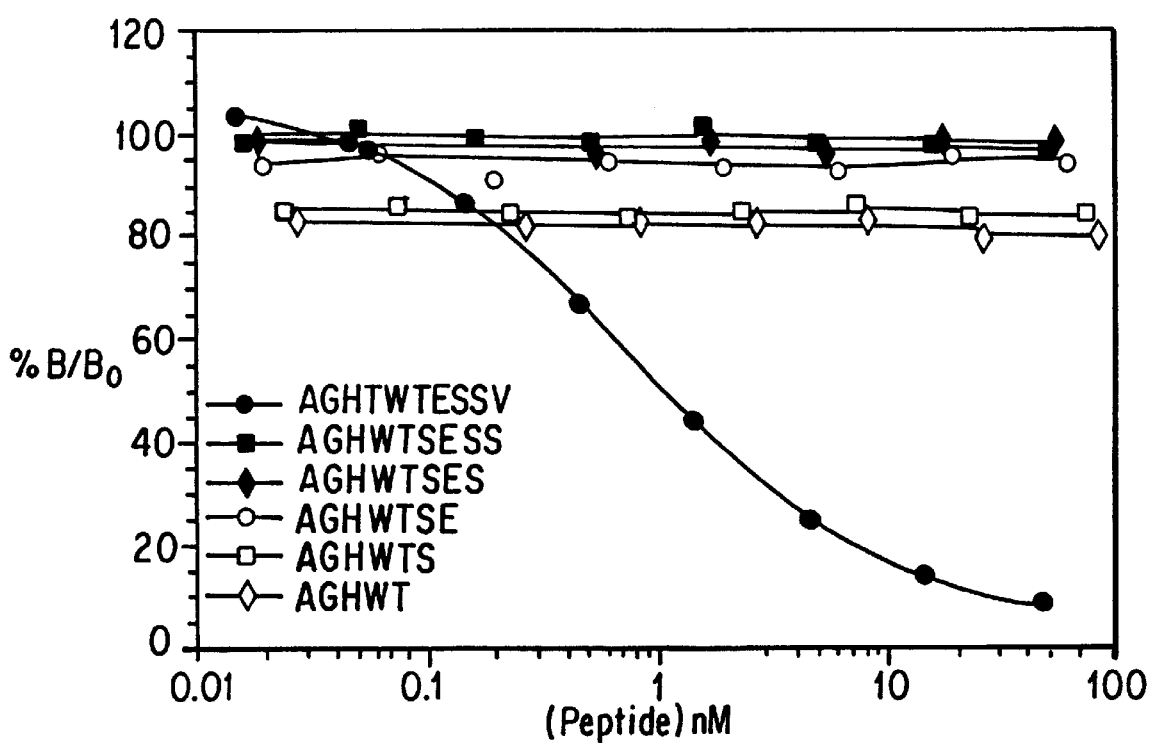

FIG. 4 shows specificity of R-770 A$\alpha$(Val$^{360}$) antiserum (C-terminal deletions).

A series of peptides with sequential deletions of C-terminal amino acids were incubated with R-770 antiserum and $^{125}$I-YRGSAGHATSESSY (SEQ. ID. NO:2) probe-peptide. When the C-terminal valine was truncated to form AGHVWTSESS$^{359}$ (SEQ. ID. NO:3), there was no recognition by the antiserum. These data confirm the requirement for the free carboxy terminal Val for recognition by the antibody.

Figure 5:
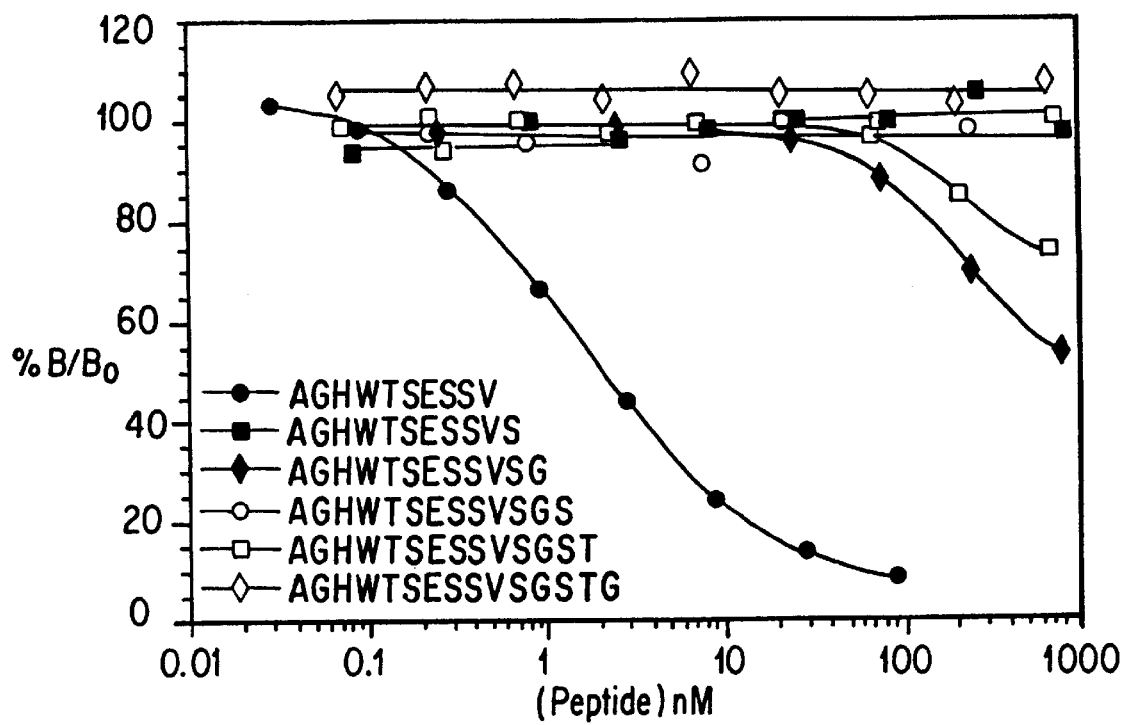

FIG. 5 shows specificity of R-770 of A$\alpha$(Val$^{360}$) antiserum (C-terminal extensions).

A series of peptides spanning the PMNE cleavage site were incubated with R-770 antiserum and with $^{125}$I-YRGSAGHATSESSV (SEQ. ID. No:2) probe-peptide. The addition of a single amino acid, Ser, to form AGHIWTSESSVS$^{361}$ (SEQ. ID. NO:4) resulted in a 300-fold loss in antibody recognition. Other spanning peptides were not recognized. These data confirmed the requirement for the free carboxy terminal Val for recognition by the antibody.

Figure 6:
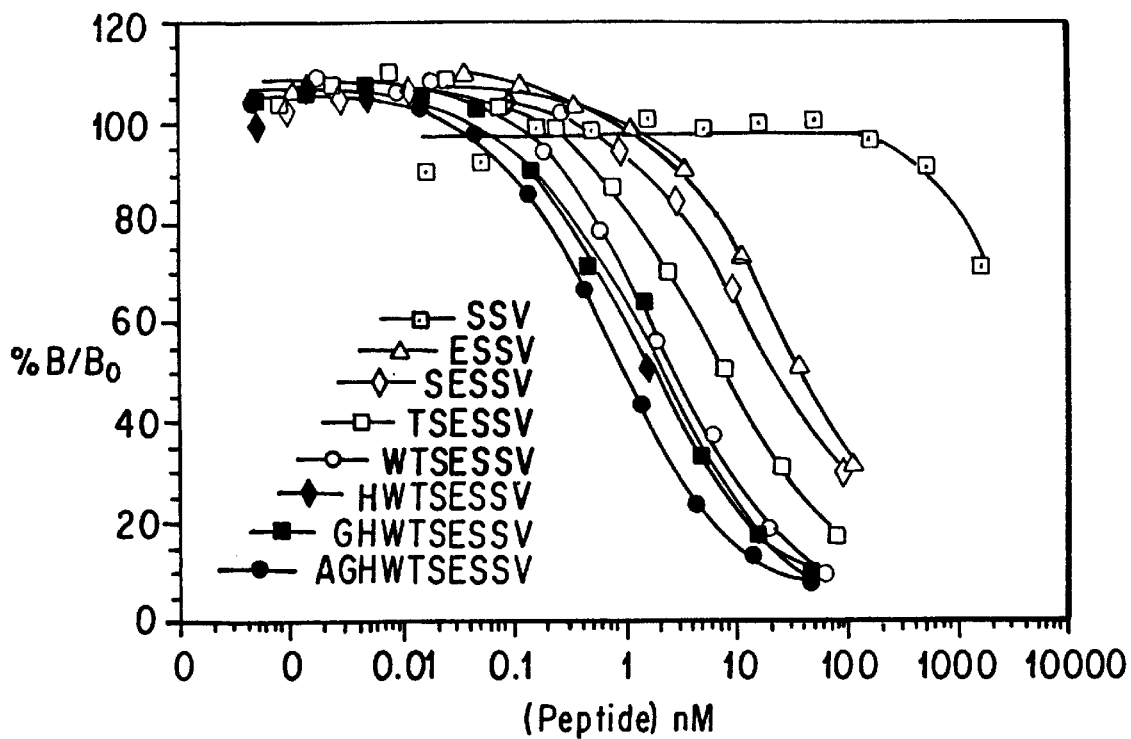

FIG. 6 shows specificity of R-770 A$\alpha$(Val$^{360}$) antiserum (N-terminal deletions).

A series of peptides to characterize the minimum length of peptide necessary for maximal recognition were incubated with R-770 antiserum and $^{125}$I-YRGSAGHATSESSV (SEQ. ID. NO:2) probe peptide. WTSESSV (SEQ. ID. NO:5) was determined to be the minimum sequence required for optimal recognition by R-770 antiserum.

Figure 7:
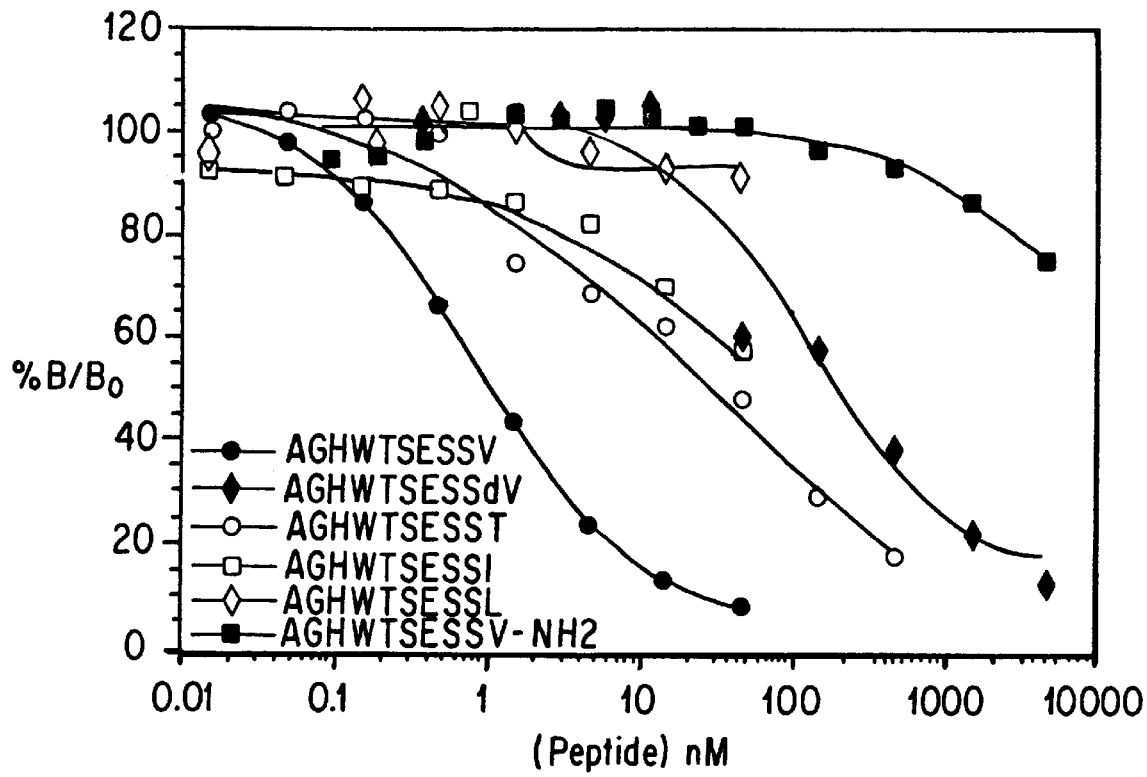

FIG. 7 shows specificity of R-770 A$\alpha$(Val$^{360}$) (C-terminal substitutions).

A series of peptides with various substitutions for the carboxy terminal Val were incubated with R-770 antiserum and $^{125}$I-YGRSAGHATSESSV (SEQ. ID. NO:2) probe peptide. The amidation of Val-COOH to Val-CONH$_2$) as well as the substitution of D-Val for L-Val resulted in a marked loss of recognition. Replacement of Val with Thr or Ile resulted in a 10–100 fold loss of recognition respectively. The replacement with Leu resulted in a complete loss of recognition.

Figure 8:
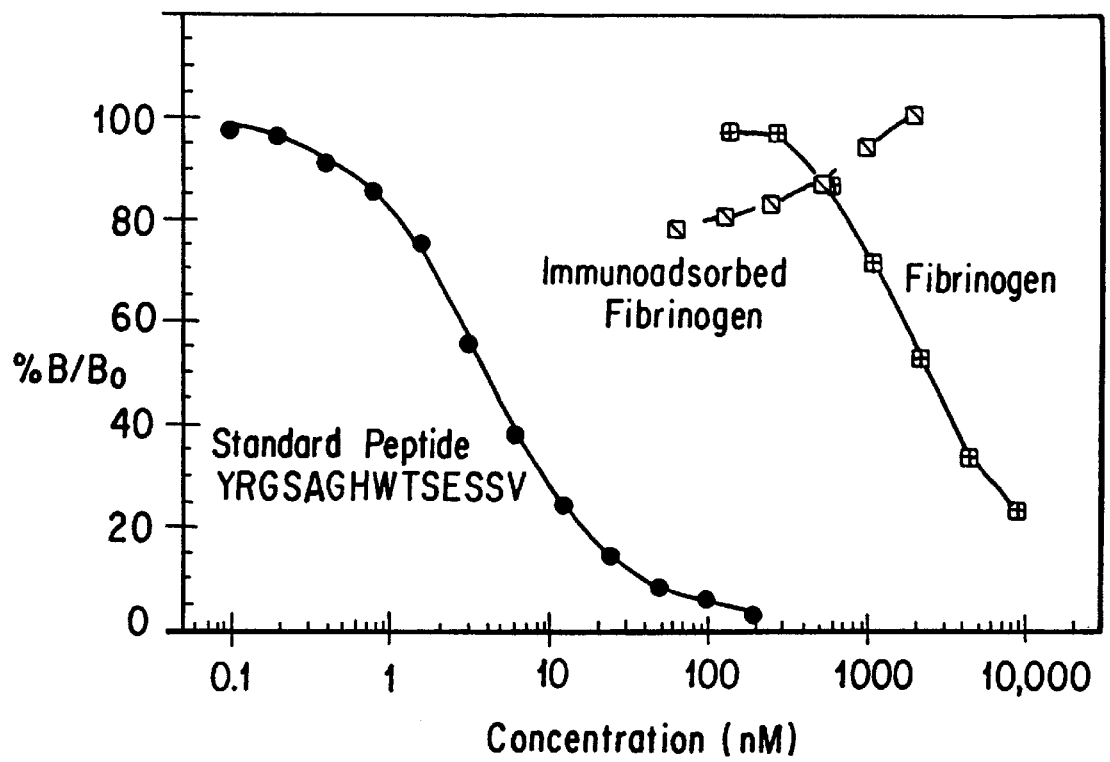

FIG. 8 shows the competitive displacement of $^{125}$I-A$\alpha$ (Val$^{360}$) with standard peptide, commercial fibrinogen and immunoadsorbed fibrinogen.

A commercial preparation of human fibrinogen was incubated with R-770 antiserum and $^{125}$I-YRGSAGHATSESSV (SEQ. ID. NO:2) probe peptide. The apparent slight cross-reactivity was removed by immunoadsorption with R-770. These data suggest that A$\alpha$(Val$^{360}$) is endogenously present in commercial preparations of fibrinogen and that R-770 does not recognize the intact (non-cleaved) molecule.

Figure 9:
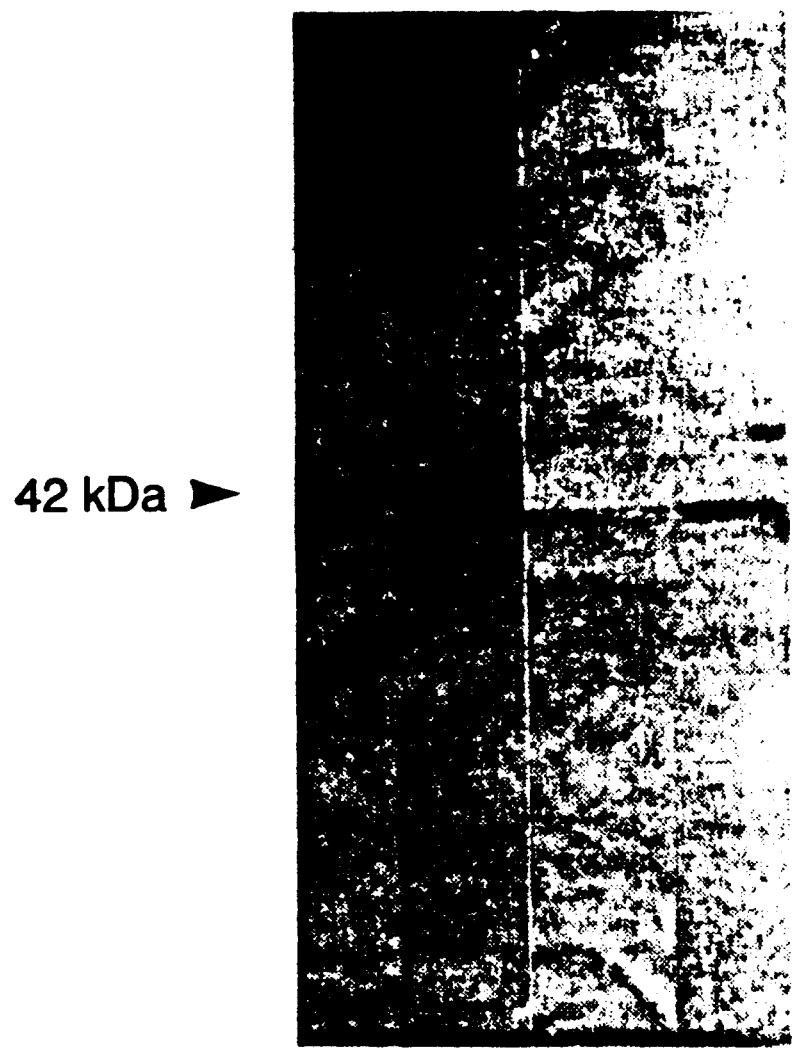

FIG. 9 shows commercial preparations of human fibrinogen that contain the A$\alpha$(Val$^{360}$) neoepitope.

A$\alpha$(Val$^{360}$) neoepitope is present in human fibrinogen. A commercial preparation of fibrinogen was evaluated by Western immunoblot analysis developed with alkaline phosphatase. A 42 kDa immunoreactive protein was detected with R-770 antiserum at about 42 kDa. No signal was found with the preimmune antiserum. The immunoreactive component was blocked by the standard peptide (10 $\mu$M) that spanned across the PMNE cleavage site.

Figure 10:
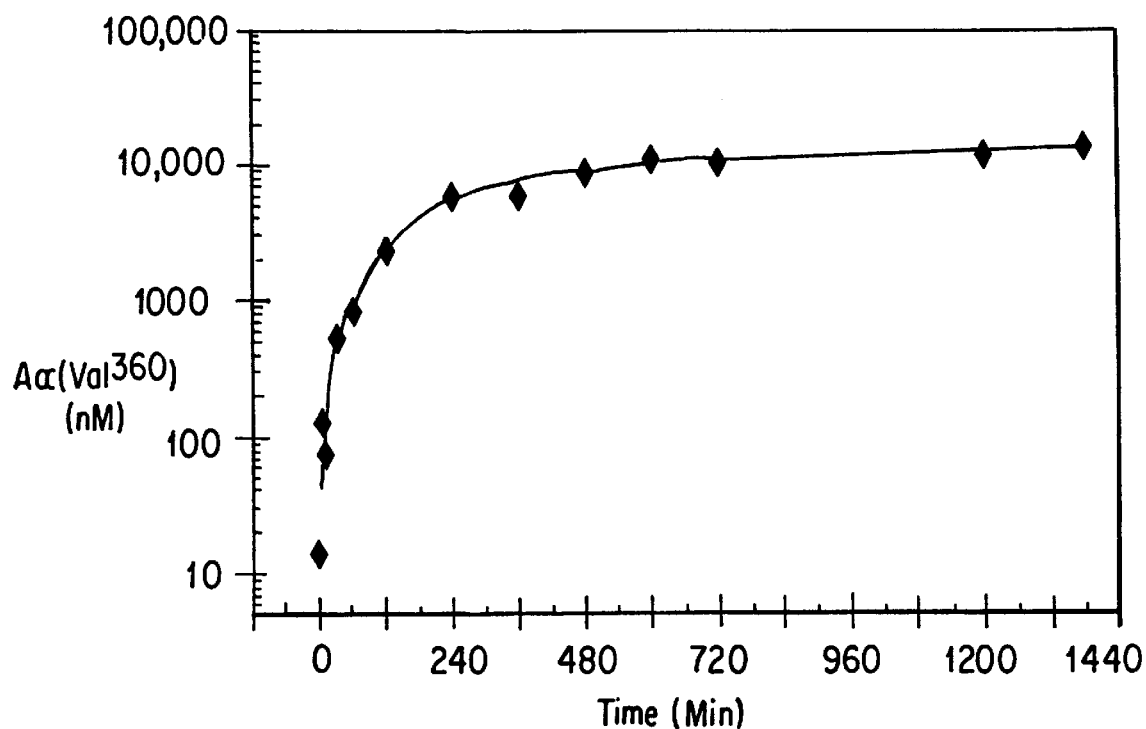

FIG. 10 shows PMN elastase incubated with human fibrinogen forms A$\alpha$(Val$^{360}$) neoepitope in a time-dependent manner.

Human fibrinogen was incubated with PMNE as a function of time at an enzyme to substrate ratio of 1:250. The amount of A$\alpha$(Val$^{360}$) was determined by RIA.

Figure 11:
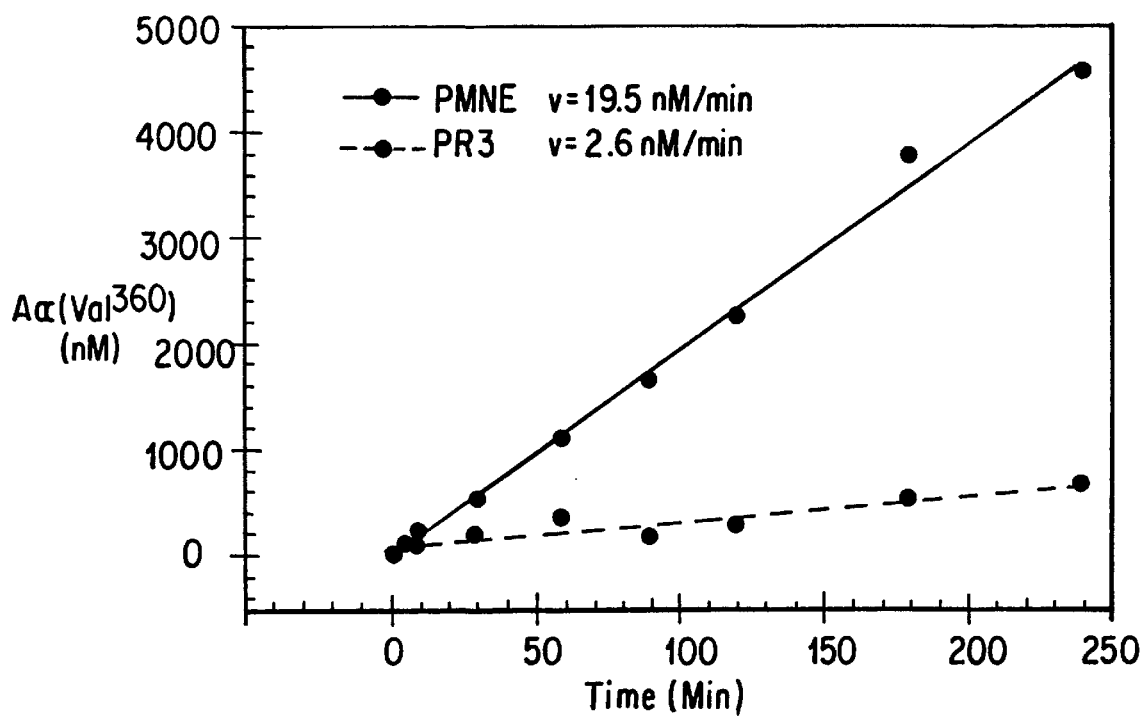

FIG. 11 shows PMN elastase and proteinase-3 hydrolyze human fibrinogen to form A$\alpha$(Val$^{360}$). Fibrinogen was incubated with PMNE and PR3 at 37° C. as a function of time at an enzyme to fibrinogen ration of 1:500. The amount of A$\alpha$(Val$^{360}$) was determined by RIA. PR3 hydrolyzed fibrinogen at 15% of the rate f PMNE.

Figure 12:
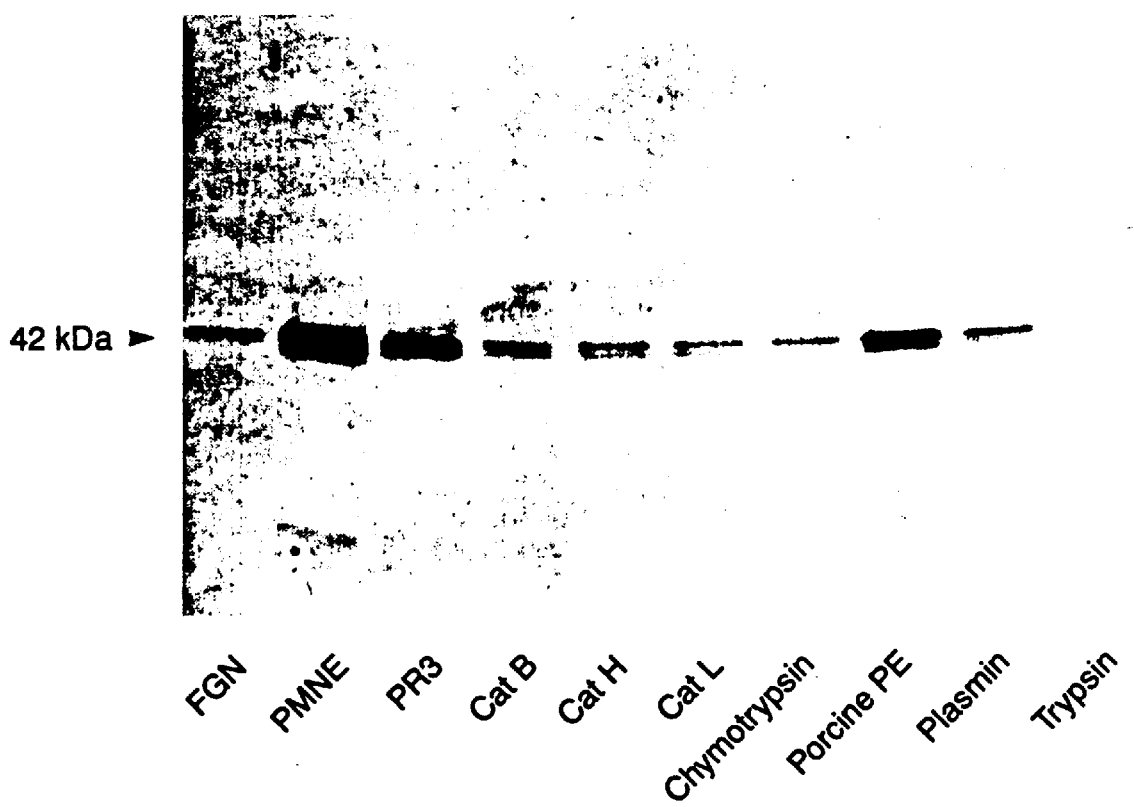

FIG. 12 shows the effect of various proteinases to hydrolyze human fibrinogen to produce A$\alpha$(Val$^{360}$). Generation of A$\alpha$(Val$^{360}$) from fibrinogen in PMNE and PR3. Fibrinogen was incubated with PMNE and other proteinases as 37° C. at an enzyme to substrate ration of 1:500. Aliquots were analyzed by Western blot. An intense immunoreactive component at 42 kDa was formed by PMNE and to a lesser amount by PR3. The human serine proteinases (plasmin and trypsin) showed no additional immunostaining over the endogenous A$\alpha$(Val$^{360}$) in the fibrinogen substrate. Likewise, the cysteine proteinases (Cat B, H and L) did not generate A$\alpha$(Val$^{360}$). However, porcine pancreatic elastase showed a detectable A$\alpha$(Val$^{360}$) signal.

Figure 13A:
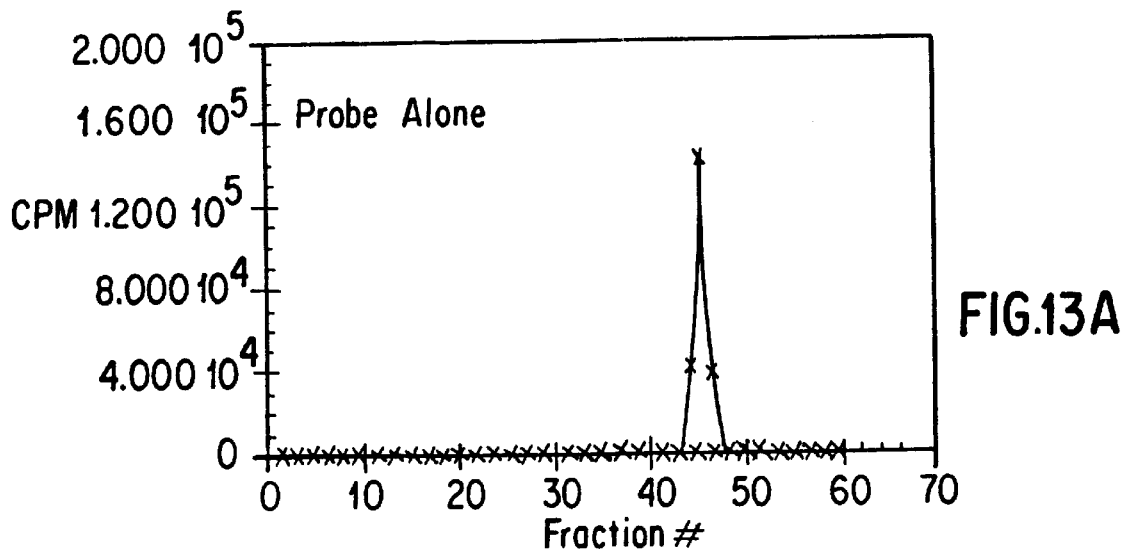
Figure 13B:
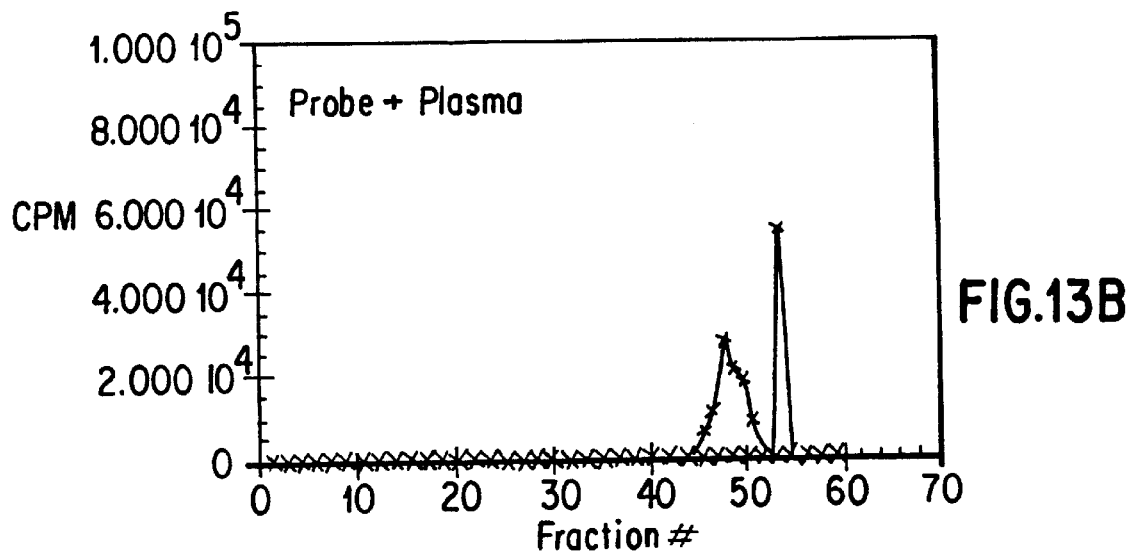
Figure 13C:
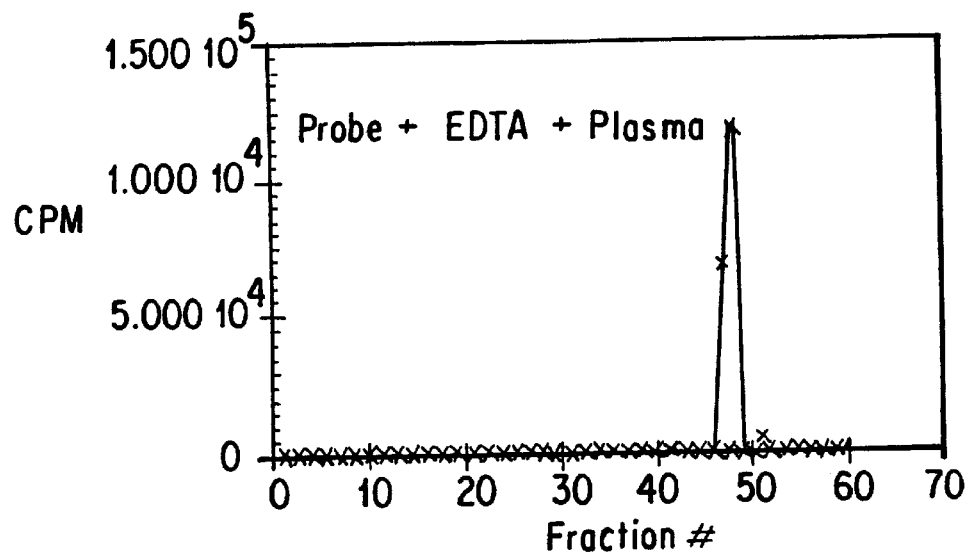

FIG. 13 shows that EDTA prevents the degradation of the A$\alpha$(Val$^{360}$) 125I-peptide probe in human plasma. $^{125}$I-YRGSAGHATSESSV (SEQ. ID. NO:2) probe peptide (200, 000 cpm) was incubated for 60 minutes at 37° C. with 100 $\mu$l of plasma containing 31 mM EDTA. The incubation mixtures were extracted into acetone, centrifuged and the supernatant chromatographed on RP-HPLC. Fractions (500 $\mu$l) were collected. and the radioactivity of each determined. This data demonstrates that EDTA (31 mM) prevented degradation of the $_{125}$I probe peptide. $^{125}$I probe peptide destriction by plasma would result in a false positive signal.

Figure 14:

FIG. 14 shows a limited digestion of fibrinogen by human PMN elastase. Characterization of a limited fibrinogen (FGN) digest by PMNE. A limited fibrinogen digest was prepared by incubation of PMNE with fibrinogen at an enzyme to substrate ration of 1:500 for 30 minutes. Aliquots were analyzed by Western immunoblot. Fibrinogen alone contained an endogenous 42 kDa immunoreactive species. Incubation of fibrinogen with PMNE formed an intense immunoreactive band at 42 kDa (the predicted MW).

Figure 15:
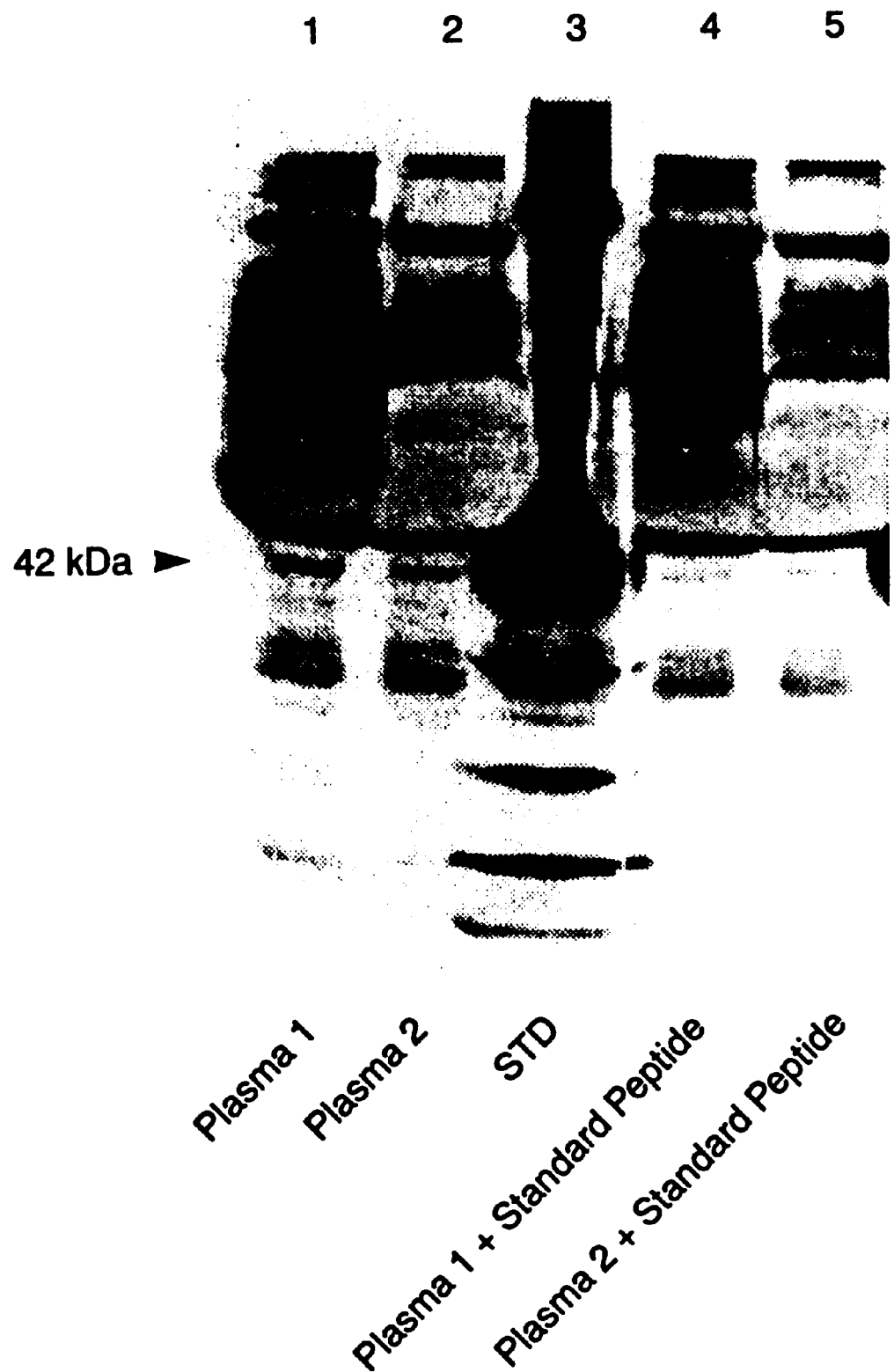

FIG. 15 shows identification of A$\alpha$(Val$^{360}$) neoepitope in normal human plasma by Western blot analysis. Normal plasma contains endogenous A$\alpha$(Val$^{360}$) neoepitope. Two plasma samples from normal individuals were analyzed by Western immunoblot using ECL detection. A 42 kDa species was seen in both samples. This immunoreactive band was blocked by standard peptide (10 μM) but not by a peptide spanning (10 μM) the PMNE cleavage site.

Figure 16B:
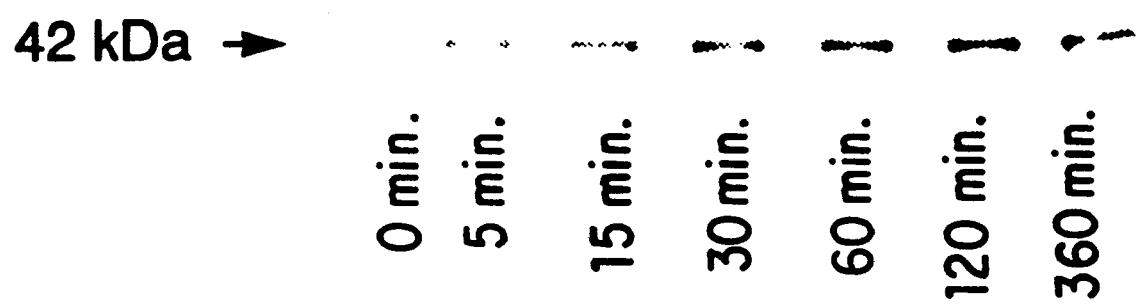

FIG. 16 shows the formation of Aα(Val$^{360}$) in human blood incubated with A23187. Time dependent formation of Aα(Val$^{360}$) in human blood incubated with the calcium ionophore A23187. Aliquots of human blood (1 ml) were incubated for various times with DMSO or A23187 (150 μm). Plasma was prepared and the concentration Aα(Val$^{360}$) was determined by RIA. The insert showed Western immunoblot analysis of the time course.

Figure 17:
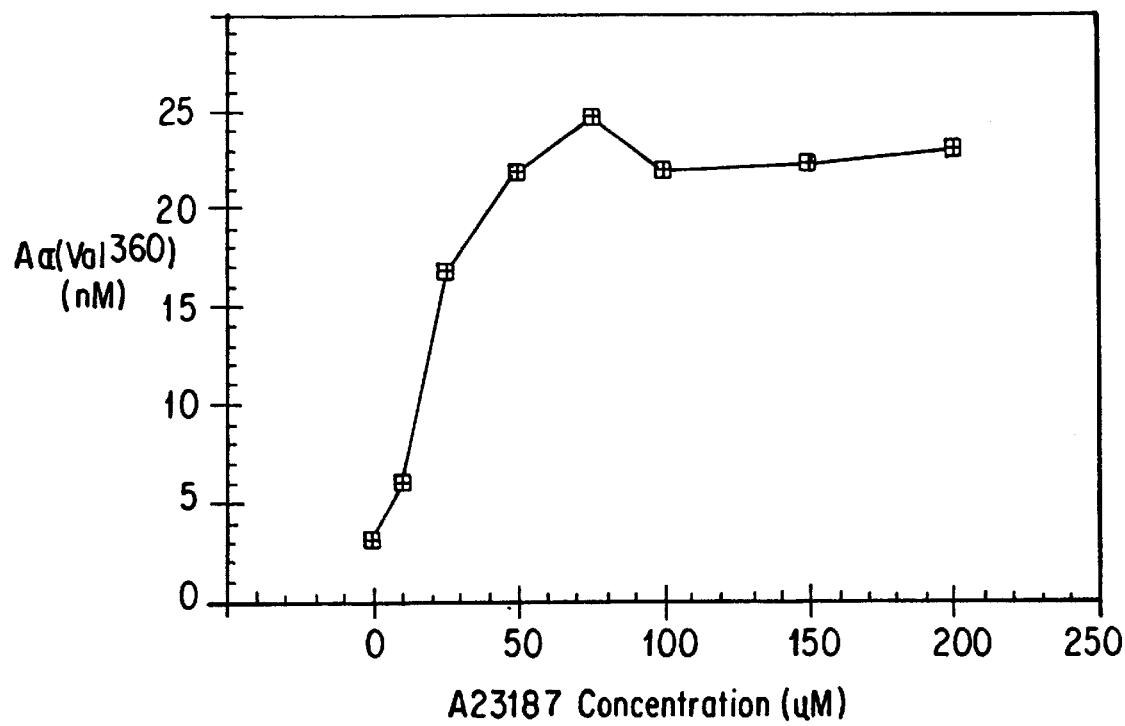

FIG. 17 shows the calcium ionophore A23187 concentration dependent formation of Aα(Val$^{360}$) in human blood. Human blood was incubated with increasing concentrations of the calcium ionophore A23187. Maximal formation of Aα(Val$^{360}$) neoepitope was achieved at 75 μM A23187.

Figure 18A:
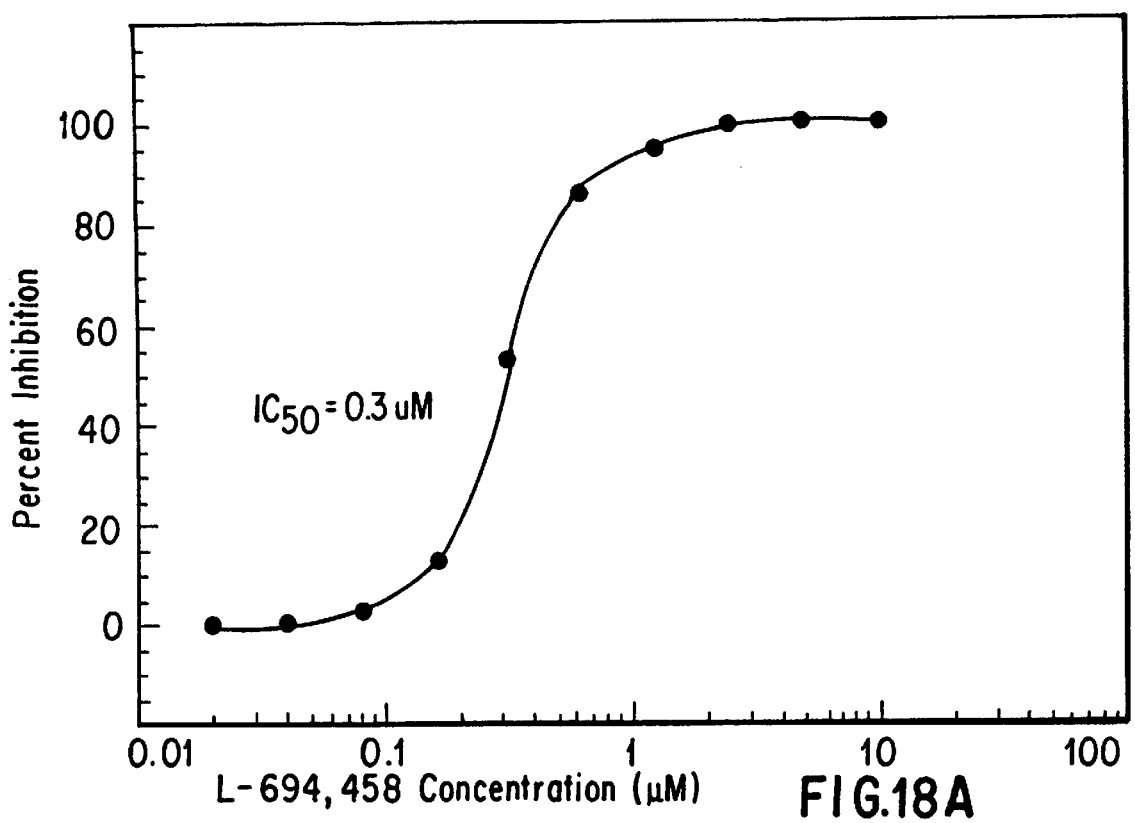
Figure 18B:
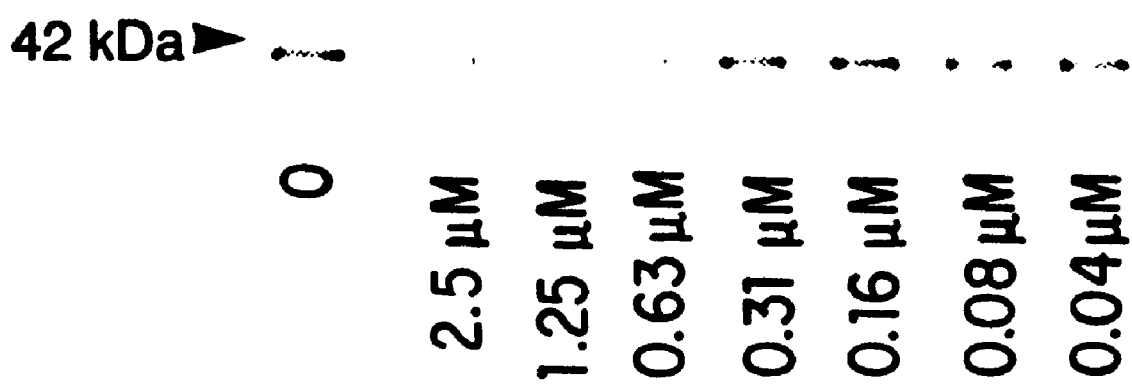

FIG. 18 shows that L-694,458 inhibits generation of the fibrinogen cleavage product Aα(Val$^{360}$) in A23187-stimulated human blood in a concentration-dependent manner. L-694,458 inhibited for formation of Aα(Val$^{360}$) in human blood. Human blood was incubated with various concentrations of L-694,458. After 10 minutes, A23187 was added. Plasma was prepared after an additional 1 hour of incubation. L-694,458 inhibited the A23187-induced Aα(Val$^{360}$) formation in a dose dependent manner with an IC$_{50}$=0.3 μM. The insert showed Western immunoblots consistent with the RIA results.

Figure 19B:
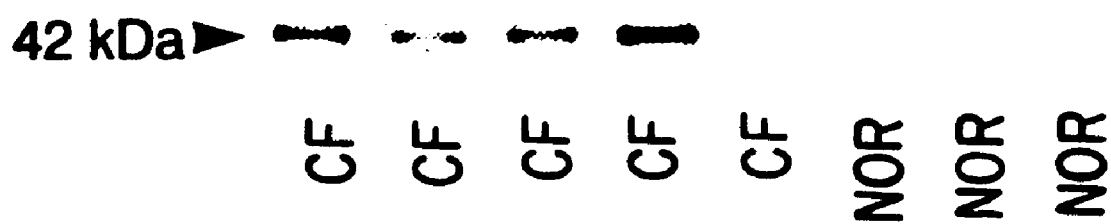

FIG. 19 shows the correlation between concentrations of Aα(Val$^{360}$) and elastase: α$_{1PI}$ complex in plasma from cystic fibrosis patients and normal donors. Aα(Val$^{360}$) and PMNE:α1PI complex concentrations in plasma from cystic fibrosis patients and normal donors. In a preliminary experiment to complete assay validation, arterial plasma samples from 25 cystic fibrosis patients and 5 normal volunteers were analyzed by RIA for Aα(Val$^{360}$) and by ELISA for PMNE:α$_{1PI}$ complexes. The insert shows selected CF and normal samples analyzed by Western immunoblot. An excellent correlation is observed between Aα(Val$^{360}$) and PMNE:a$_{1PI}$ concentrations (R=0.99).

Figure 20:
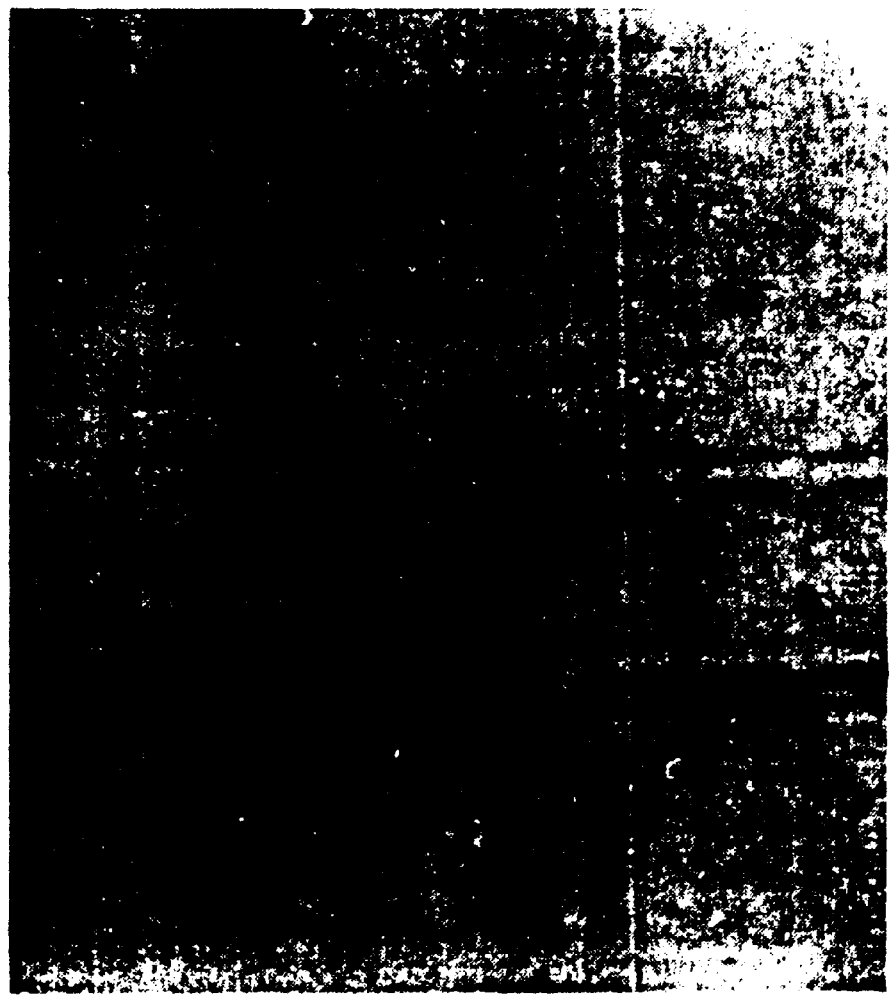

FIG. 20 shows the identification of Aα(Val$^{360}$) neoepitope in rheumatoid arthritis and gout synovial fluid. Western immunoblot of Aα(Val$^{360}$) neoepitope in synovial fluids. Synovial fluids from patients with various joint diseases were analyzed by Western blot. In contrast to plasma which showed predominately a single 42 kDa immunostaining band, synovial fluid contained an additional component at 20 kDa, suggesting as additional cleavage fibrinogen.

FIG. 21 is a table which shows the recovery of standard peptide and limited elastase fibrinogen digest containing Aα(Val$^{360}$) from human blood. Fibrinogen digest (FD) (9.74 pmoles) and the Aα(Val$^{360}$) standard peptide (SP) (20 pmoles) were added to 1 mL aliquots of human blood in the presence or absence of EDTA (22.7 mM). The samples were incubated at 37° C. for 1 hour, centrifuged and the plasma collected. EDTA (31 mM) was added to the plasma derived from blood not incubated with EDTA. The concentration of Aα(Val$^{360}$) in the plasma was determined by RIA. Note: The hematocrit of the donor was 38.9%, thus the plasma concentration of the FD=16.0 nM and the plasma concent5ration of SP 32.8 nM. These data indicate that the Aα(Val$^{360}$) neoepitope can be quantitatively recovered from blood containing 31 mM EDTA.

FIG. 22 shows normal human plasma containing the fibrinopeptide Aα(Val$^{360}$). Blood was collected into heparin by antecubital venipuncture or from the radial artery. Plasma was prepared and the concentration of Aα(Val$^{360}$) determined by RIA. These data are the first direct demonstration of PMNE activity in apparently healthy individuals.

FIG. 23 is a table which shows the concentration of Aα(Val$^{360}$) formed in human blood incubated with DMSO and A23187. Aliquots of human blood (1 mL) were incubated at 37° C. with A23187 (150 μM) or DMSO. After 60 minutes the samples were centrifuged. Plasma aliquots (350 ml) were added to 50 ml 250 mM EDTA. The amounts of Aα(Val$^{360}$) were determined by RIA. The data have been corrected for recovery of "Limited Elastase Fibrinogen Digest" (either 0.97 pmoles or 23.7 pmoles were added to 1 ml of blood) and for EDTA dilution. This is expressed as pmoles/ml of plasma as well as being corrected for the number of PMN (1×10$^6$). These data show that Aα(Val$^{360}$) was found in human blood incubated with A23187. An approximate 7-fold increase was observed over the endogenous signal.

FIG. 24 is a table which shows the concentration of Aα(Val$^{360}$) neoepitope in synovial fluids. EDTA (to yield a final concentration of 31 mM) was added to aliquots of synovial fluids and the concentration of Aα(Val$^{360}$) determined by RIA. A PMNE generated fibrinogen digest containing Aα(Val$^{360}$) was also added as a recovery standard. The data have been corrected for the recovery of the fibrinogen digest. These data demonstrate the activity of PMNE in rheumatoid arthritis and gout synovial fluid samples.

DETAILED DESCRIPTION OF THE INVENTION

The invention is a radioimmunoassay based on the Aα(Val$^{360}$) epitope which allows the evaluation of the potency of elastase inhibitors to inhibit formation of cleavage products containing this neoepitope in a variety of in vitro cell biological situations. This RIA detects an endogenous Aα(Val$^{360}$) normal human plasma and elevated levels of Aα(Val$^{360}$) in cystic fibrosis plasma and in rheumatoid arthritis synovial fluid samples. Thus, this RIA can monitor the severity of disease and evaluate the efficacy of PMNE inhibitors in vivo. The assay procedure is a single step assay which allows for the rapid and reproducible detection of PMNE-specific cleavage peptide.

Human polymorphonuclear leukocyte elastase (PMNE) cleaves human fibrinogen at multiple sites. Cleavage of the Aα chain at Aα(Val$^{360}$–Ser$^{361}$) generates a stable product as indicated by its presence in from biological fluids.

Figure 1:
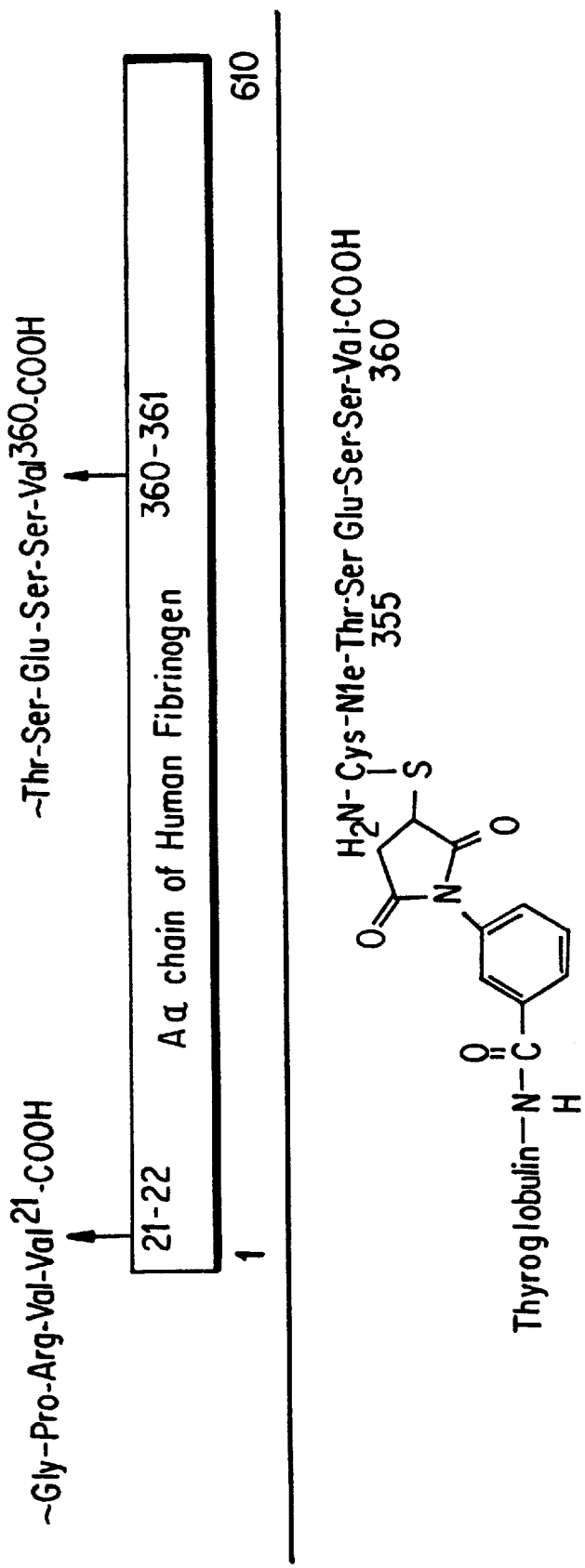
FIG. 1 shows neoepitopes generated by cleavage of the Aα(Val$^{360}$) assay. The standard peptide (YRGSAGHWTSESSV) (SEQ. ID.NO:1) was incubated overnight with R-770 antiserum and $^{125}$I-

Human fibrinogen is a hetero-dimeric glycoprotein consisting of 3 non-identical chains, Aα, Bβ and γ. PMNE cleaves human fibrinogen at multiple sites. Primary sites of cleavage include Aα(Val$^{21}$–Glu$^{22}$), Aα(Val$^{360}$–Ser$^{361}$), Aα(Val$^{450}$–Ile$^{451}$), Aα(Val$^{464}$–Thr$^{465}$), Aα(Met$^{476}$–Asp$^{477}$), Aα(Thr$^{568}$–Ser$^{569}$), γ(Thr$^{305}$–Ser$^{306}$), γ(Val$^{347}$–Tyr$^{348}$) and γ(Ala$^{357}$–Ser$^{358}$). We have developed two antipeptide antibodies, one of which specifically measures PMNE hydrolysis of fibrinogen at the Aα(Val$^{21}$–Glu$^{22}$) position to release a 21 residue N-terminal peptide, and a second which measures cleavage at Aα(Val$^{360}$–Ser$^{361}$), to release a 250 residue C-terminal fragment (FIG. 1). The Aα(Val$^{360}$) carboxyl terminal fragment remains associated with the β and γ chains of fibrinogen due to the disulfide network of the protein. Neither of the 2 specific antisera recognize intact fibrinogen. Both of these RIAs allow the evaluation of the potency of PMNE inhibitors, such as elastase inhibitors, to inhibit fibrinopeptide neoepitope generation in whole blood stimulated with the calcium ionophore A23187. However, a major disadvantage of the Aα(Val$^{21}$) assay is the rapid in vivo clearance and metabolism of the peptide neoepitope Aα(Val$^{21}$) (t$_{1/2}$ of 30 sec in both the dog and rhesus monkey). In an extensive series of experiments we have been unable to detect the Aα(Val$^{21}$) neoepitope in normal human plasma or in plasma samples from PiZZ individuals, nor in plasma from from patients with cystic fibrosis, emphysema or chronic bronchitis.

The Aα(Val$^{360}$) neoepitope is associated with a large protein fragment which results in a substantially slower clearance rate than Aα(Val$^{21}$) peptide. Utilizing the Aα(Val$^{360}$) RIA an endogenous signal is detected in normal human plasma. This signal is elevated in cystic fibrosis plasma samples. In addition, levels of Aα(Val$^{360}$) neoepitope are elevated in both rheumatoid arthritis and gout synovial fluid but not in osteoarthritis synovial fluid.

This assay may be incorporated into a diagnostic kit for measuring PMNE activity in man. This assay will allow the evaluation of the potency of elastase inhibitors in plasma, sputum and synovial fluid following oral administration of drug.

The present invention relates to the identification of time dependent, major human leukocyte elastase cleavage sites within an intact fibrinogen molecule. The structure of mammalian fibrinogen is known in the art and the human fibrinogen amino acid sequence has been schematically depicted by Doolittle, Ann. N.Y. *Acad. Sci.* 408: 13–26 (1983). The amino acid sequences in human fibrinogen have been characterized by Henschen et al., Ann. N.Y. *Acad. Sci.* 408: 28–43 (1983). The enzymatic cleavage sites are determined by reacting human fibrinogen (Sigma), about 200 nanomoles, with HLE (Elastin Products) or monocyte elastase, about 1 nanomole, at about 37° C. for various times periods ranging from about 0 minutes to about 2 hours. The reactions are carried out in an acceptable buffer, preferably Tris, at a pH of about 7.0 in a final volume of about 1.0 ml. Each reaction is stopped by the addition of cold alcohol, preferably ethanol at about 3° C. and incubated at about 3° C. for about 30 minutes. Following incubation the suspension is centrifuged at about 3,000×g at about 3° C. for about 20 minutes. The supernatant fluid is collected and transferred to clean tubes and concentrated to dryness in a Speed-Vac for about 16 hours. Each sample is reconstituted in an acceptable high performance liquid chromatography (HPLC) buffer, preferably water and acetonitrile mixtures and chromatographed on a C1–18 DUPONT-ZORBAX™ chromatography column, about 0.4×25 cm. The peptides are eluted with a linear gradient consisting of about H$_2$O:acetonitrile:trifluoroacetic acid 95:5:0.2 v/v/v, to about H$_2$O:acetonitrile:trifluoroacetic acid 60:40:0.2 v/v/v. Peptide peaks are collected, re-chromatographed to demonstrate purity and subjected to N-terminal amino acid sequence analysis on an Applied Biosystems Protein Peptide Sequencer, Model 470A. Eight major peaks are identified and the amino acid sequences are used to determine the sites of HLE cleavage. Nineteen minor amino acid peaks are also identified and can be used to identify minor or secondary HLE cleavage sites. The major HLE cleavage sites are shown in the following table.

TABLE 1

Major Human Leukocyte Elastase Cleavage Sites in Human Fibrinogen

| Chain | Site |
| --- | --- |
| 1. A alpha | 21–22 |
|  | Val  Glu |
| 2. A alpha | 360–361 |
|  | Val  Ser |
| 3. A alpha | 450–451 |
|  | Val  Ile |
| 4. A alpha | 464–465 |
|  | Val  Thr |
| 5. A alpha | 476–477 |
|  | Met  Asp |
| 6. A alpha | 568–569 |
|  | Thr  Ser |
| 7. gamma | 305–306 |
|  | Thr  Ser |
| 8. gamma | 347–348 |
|  | Val  Tyr |
| 9. gamma | 357–358 |
|  | Ala  Ser |

Knowing the specific elastase cleavage sites of human fibrinogen allows the synthesis of antigenic peptides and peptide probes of varying amino acid length corresponding to both the amino and carboxyl termini of the primary cleavage sites. Antigenic peptide as used herein denotes a peptide that can combine with or bind to specific antibody raised against the antigen or can induce the formation of antibody which will react with the antigen. The preferred embodiment of antigenic peptides and peptide probes includes, but is not limited to the first 15 amino acids on either the carboxyl or amino side of described enzymatic cleavage sites. It is to be understood that the embodiment of this invention includes peptides ranging in length from about 5 amino acids to about 25 amino acids or longer. All amino acid sequences depicted herein are numbered from the amino terminus to carboxyl terminus according to the scheme shown by Henschen et al., Ann. N.Y. *Acad. Sci.* 408: 28–43 (1983).

Representative carboxyl termini antigenic peptide and probe peptide amino acid sequences are shown in the following table.

TABLE 2

Carboxyl Terminus Antigenic Peptides

A alpha chain

```
       7                                                              21
1.  Asp Phe Leu Ala Glu Gly Gly Gly Val (SEQ ID NO:6) Arg Gly Pro Arg Val Val 346                                                             360
2.  Ser Glu Arg Gly Ser Ala Gly His Trp Thr Ser Glu Ser Ser Val (SEQ ID NO:7)

436                                                             450
3.  Thr Thr Thr Arg Arg Ser Cys Ser Lys Thr Val (SEQ ID NO:8) Thr Lys Thr Val 450                                                             464
```

TABLE 2-continued

Carboxyl Terminus Antigenic Peptides

4. Val (SEQ ID NO:9) Ile Gly Pro Asp Gly His Lys Glu Val Thr Lys Glu Val Val 462                                           476
5. Glu Val Val Thr Ser Glu Asp Gly Ser Asp Cys Pro Glu Ala Met (SEQ ID NO:10)

554                                             568
6. Arg Gly Lys Ser Ser Ser Tyr Ser Lys Gln Phe Thr (SEQ ID NO:11) Ser Ser Thr gamma chain 291                                             305
1. Asp Gly Phe Asp Phe Gly Asp Asp Pro Ser Asp Lys Phe Phe Thr (SEQ ID NO:12)

333                                             347
2. Gly Trp (Trp)* Met Asn Lys Cys His Ala Gly His Leu Asn Gly Val(SEQ ID NO:13)

343                                             357
3. His Leu Asn Gly Val Tyr Tyr Gln Gly Gly Thr Tyr Ser Lys Ala (SEQ ID NO:14)

*Tentative amino acid assignment.

The specificity of the antigenic peptides and the peptide determined by the epitope directly adjacent to the amino or carboxy terminus of the enzyme cleavage site. Epitope as used herein denotes an antigenic determinant site of know structure, amino acid sequence, which is responsible for the specificity of the antigen and can react specifically with antibody raised against the antigen which contains the eptiope. The preferred embodiment of epitopes includes, but is not limited to, the first 5 amino acids on either the carboxyl or amino side of the described enzymatic cleavage sites. Representative carboxyl termini epitope amino acid sequences are shown in the following table.

TABLE 3

Carboxyl Terminus Epitopes Peptides

A alpha chain 17             21
1. Gly Pro Arg Val Val (SEQ ID NO:15)

356          360
2. Ser Glu Ser Ser Val (SEQ ID NO:16)

446          450
3. Val Thr Lys Thr Val (SEQ ID NO:17)

TABLE 3-continued

Carboxyl Terminus Epitopes Peptides 460          464
4. Thr Lys Glu Val Val (SEQ ID NO:18)

472          476
5. Cys Pro Glu Ala Met 564          568
6. Phe Thr Ser Ser Thr gamma chain 301          305
1. Asp Lys Phe Phe Thr (SEQ ID NO:21)

343          347
2. His Leu Asn Gly Val (SEQ ID NO:22)

353          357
3. Thr Tyr Ser Lys Ala (SEQ ID NO:23)

Representative amino termini antigenic peptide and probe peptide amino acid sequences are shown in the following table.

TABLE 4

Amino Terminus Antigenic Peptides

A alpha chain 22                                             36
1. Glu Arg His Gln Ser Ala Cys (SEQ ID NO:24) Lys Asp Ser Asp Trp Pro Phe Cys 361                                      375
2. Ser Gly Ser Thr Gly Gln Trp His Ser Glu Ser Gly Ser Phe Arg (SEQ ID NO:25)

451                                      465
3. Ile Gly Pro Asp Gly His Lys Glu Val Thr Lys Glu Val Val Thr (SEQ ID NO:26)

465                                      479
4. Thr Ser Glu Asp Gly Ser Asp Cys Pro Glu Ala Met Asp Leu Gly (SEQ ID NO:27)

477                                      491
5. Asp Leu Gly Thr Leu Ser Gly Ile Gly Thr Leu Asp Gly Phe Arg (SEQ ID NO:28)

569                                      583
6. Ser Tyr Asn Arg Gly Asp Ser Thr Phe Glu Ser Lys Ser Tyr Lys (SEQ ID NO:28)

TABLE 4-continued

Amino Terminus Antigenic Peptides gamma chain

```
    306                                             320
7.  Ser His Asn Gly Met Gln Phe Ser Thr Trp Asp Asn Asp Asn Asp (SEQ ID NO:30)

348                                   362
8.  Tyr Tyr Gln Gly Gly Thr Tyr Ser Lys Ala Ser Thr Pro Asn Gly (SEQ ID NO:31)

358                                                   372
9.  Ser Thr Pro Asn Gly Tyr Asp Asn Gly Ile Ile (Trp)* Ala Thr (Trp)* (SEQ ID NO:32)
```

*Tentative amino acid assignment.

Representative amino termini epitope amino acid sequences are shown in the following table.

TABLE 5

Amino Terminus Epitopes-5 Amino Acids

A alpha chain
```
     22              26
1.   Glu Arg His Gln Ser (SEQ ID NO:33)

261             365
2.   Ser Gly Ser Thr Gly (SEQ ID NO:34)

451             455
3.   Ile Gly Pro Asp Gly (SEQ ID NO:35)

465             469
4.   Thr Ser Glu Asp Gly (SEQ ID NO:36)

477             481
5.   Asp Leu Gly Thr Leu (SEQ ID NO:37)

569             573
6.   Ser Tyr Asn Arg Gly (SEQ ID NO:38)
``` gamma chain
```
    306             310
1.   Ser His Asn Gly Met (SEQ ID NO:39)

348             352
2.   Tyr Tyr Gln Gly Gly (SEQ ID NO:40)

358             362
3.   Ser Thr Pro Asn Gly (SEQ ID NO:41)
```

The above identified and described peptides are used as angtigens to produce antibodies which react specifically with the unique amino acid sequence of the elastase cleavage product. The novel peptide are also used as specific probes or antigens for determining antiserum titer in body fluids. The various peptides can be used as specificity peptides to evaluate the specificity of the unique antibodies prepared against the various peptides.

Immunogens are prepared by attaching the individual antigenic peptides or individual epitope peptides, or any peptide containing said epitope onto an immunogenic carrier molecule capable of inducing antibody synthesis in animals. An immunogen is defined herein as a substance of sufficient size that when introduced into an animal stimulate the production of antibodies reactive with the specific antigen or epitope. Immunogenic carrier is defined herein as a protein or other high molecular weight compound to which an antigen or epitope is conjugated in vitro and which renders the antigen or epitope capable of stimulating or increasing an immune response. Peptides containing the specific amino acid epitope are termed herein antigenic peptides. Antigenic peptides include but are not limited to the peptides shown in Table 2, Table 3, Table 4 and Table 5. It is to be understood that the embodiment of this invention includes the use of the defined epitopes and antigens, without the addition of immunologic carriers or any other chemical modification, as direct stimulants of antibody formation.

The peptide antigens of the present invention may be synthesized using any suitable peptide synthesis technique, such as solid phase peptide synthesis chemistry following the method of Merrifield, *J. Am. Chem. Soc.* 85: 2149–2154. The peptides terminating in a carboxyl group are synthesized on the standard Merrifield resin. The peptides terminating in an amide group are synthesized on a 4-methyl benzhydrylamine resin. Hydrofluoric acid cleavage of the C-terminal amino acid residue from this resin yields a peptide containing an amide terminus. The procedures are known in the art. Linking amino acids such as cysteine are added, if necessary, to either the amino or carboxyl terminus of antigen peptides either during synthesis or chemically after synthesis to provide a free sulhydryl group to facilitate coupling to an immunogenic carrier. The linking amino acid is added at the opposite end of the peptide sequence from the cleavage site to allow attachment to the carrier protein leaving the proteolytic cleavage site exposed. Internal molecular markers such as norleucine may also be added during the synthesis of antigenic peptides to evaluate the number of peptide molecules bound to the carrier. Norleucine is preferred since it is not a usual amino acid component of natural proteins. The synthesized peptides are purified by preparative reverse phase high performance liquid chromatography (HPLC) with identity and purity being established by fast atom bombardment (FAB) mass spectrometry and amino acid analysis, techniques known in the art.

The antigenic peptides are convalently coupled to high molecular weight carrier proteins which include, but are not limited to bovine serum albumin (BSA), bovine thyroglobulin (BT), keyhole limpet hemocyanin (KLH), ovalbumin (OA), and the like, with BSA and BT being preferred. The antigenic peptides are coupled to the linking amino acid, cysteine, by maleimido-NHS-ester heterobifunctional coupling reagents which include, but are not limited to, m-Maleimidobenzoyl-N-hydroxysuccinimide ester (MSB), m-Maleimidobenzoyl-sulfosuccinimide ester (Sulfo-MBS), Succinimidyl 4-(Maleimidomethyl)-cyclohexane-1-carboxylate (SMCC) sulfosuccinimidyl 4-(N-Maleimidomethyl)cyclohexane-1-carboxylate (Sulfo-SMCC), Succinimidyl 4-(p-Maleimidophenyl) butryate, (SMPB), sulfoccinimidyl 4-(p-Maleimidophenyl) butyrate, (Sulfo-SMPB), with MBS and Sulfo-MBS being preferred. The carrier protein, generally BSA or BT, is prepared by dissolving about 10 mg in about 2.5 ml of about 100 mM phosphate (K$^+$) buffer at about pH 7.25. All buffers used in the coupling process must be exhaustively de-gassed prior to use. To the dissolved carrier is added about 5 mg of the coupling reagent, and the solution is stirred for 15 minutes to 30 minutes. The activated protein carrier is purified by size exclusion chromatography using SEPHADEX™ chromatography gel about G25, a PD10 pre-packed column (Pharmacia). The activated carrier is eluted with about 3.5 ml of about 100 mM phosphate (K$^+$) buffer, pH about 5.8 into about 6 micromoles of purified lyophilized peptide for carrier-peptide linking. The mixture is maintained at about 4° C. overnight, and the cross-linked peptide is purified by size exclusion chromatography using SEPHADEX™ chromatography gel about G25 (Pharmacia) or dialysis and lyophilized.

The antigenic peptide-carrier conjugate is analyzed to determine the number of molecules of peptide bound to each molecule of carrier. A sample of peptide-carrier conjugate, about 0.5 mg, is hydrolyzed in about 1 ml of about 6.0 N HCl maintained at about 110° C., constantly boiling HCL in vacuo for about 24 hours. There will be one norleucine molecule in the hydrolysate for each peptide molecule bound the carrier. An adequate immunogen, containing either a 15 amino acid peptide or a 5 amino acid peptide, will contain at least 5 moles of antigen peptide per mole of carrier.

Monospecific antibodies to the antigenic peptides are purified from mammalian antisera containing antibodies reactive against both the peptides and the carrier or prepared as monoclonal antibodies reactive with only the specific peptide using the technique of Kohler and Milstein. Monospecific antibody as used herein is defined as a single antibody species or multiple antibody species with homogenous binding characteristics for the relevant peptide antigen. Homogenous binding as used herein refers to the ability of the antibody species to bind to a specific antigen or epitope, such as those associated with the HLE cleavage sites of human fibrinogen, as described above. Peptide specific antibodies are raised by immunizing animals such as mice, rats, guinea pigs, rabbits, goats and horses, with rabbits and guinea pigs being preferred, with an appropriate concentration of the specific peptide-carrier complex either with or without an immune adjuvant. Preimmune serum is collected prior to the first immunization. Each animal receives between about 50 μg and about 300 μg of a single peptide-carrier complex associated with an acceptable immune adjuvant. Such acceptable adjuvants include, but are not limited to Freund's complete, Freund's incomplete, alum-precipitate, water in oil emulsion containing *Corynebacterium parvum* and tRNA. The initial immunization consisted of the specific peptide-carrier conjugate in, preferably, Freund's complete adjuvant at multiple sites either subcutaneously or intradermally. Each animal is bled at regular intervals, preferably weekly, to determine antibody titer. The animals may or may not receive booster injections following the initial immunization. Those animals receiving booster injections are given an equal amount of peptide-carrier conjugate in Freund's incomplete adjuvant by the same route. Booster injections are given at about three week intervals until maximal titer is obtained. At about 7 days after each booster immunization or about weekly after a single immunization, the animals are bled, the sera are collected, aliquoted and stored at about −20° C.

Monoclonal antibodies (mAb) reactive with the peptide antigens of human leukocyte elastase-cleaved fibrinogen, as shown in Tables 2, 3, 4 and 5, are prepared by immunizing inbred mice, preferably Balb/c mice with the appropriate peptide-conjugate. The mice are immunized by the intraperitoneal or subcutaneous route with about 0.1 mg to about 10 mg, preferably about 1 mg, of the specific antigenic peptide conjugate in about 0.5 ml buffer or saline incorporated in an equal volume of an acceptable adjuvant. Such acceptable adjuvants include, but are not limited to, Freund's complete, Freund's incomplete, alum-precipitate, water-in-oil emulsion containing *Corynebacterium parvum* and t-RNA, with Freund's incomplete adjuvant (IFA) being preferred. The mice received an initial immunization on day 0 and are rested for approximately 24 weeks. Immunized mice are given a booster immunization of about 1 mg of the conjugate or peptide in a buffer solution such as phosphate buffered saline by the intravenous route. At approximately day three after the booster immunization the mice are tested for peptide antibody. Lymphocytes, from antibody positive mice, preferably splenic lymphocytes, are obtained by removing spleens from immunized mice by standard procedures known to the art. Hybridoma cells are produced by mixing the splenic lymphocytes with an appropriate fusion partner under conditions which will allow the formation of stable hybridomas. Fusion partners may include, but are not limited to: mouse myelomas P3–NS1-Ag 4-1; MPC-11; S-194: NS.1 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatants are collected from growth positive wells on about days 14, 18 and 21 and are screened for antibody production by a solid phase immunoradioassay (SPIRA) using the specific peptide antigens as the antigen. The culture supernates are also tested in the Ouchterlony precipitin assay to determine the isotype of the mAb. Cells from the antibody positive wells are cloned in soft agar by the technique of MacPherson, "Soft Agar Techniques", in *Tissue Culture Methods and Applications*, Kruse and Paterson, Eds Academic Press, 1973.

Monoclonal antibodies are produced in vivo by injecting pristane primed BALB/c mice, approximately 0.5 ml per mouse, with about 2×10$^6$ to about 6×10$^6$ hybridoma cells, about 4 days after priming. Ascites fluid is collected at approximately 8–12 days and the monoclonal antibodies precipitated with ammonium sulfate, about 35% to about 60% of saturation, with 45% being preferred, washed and resuspended in a physiologically acceptable buffer at a pH of about 7.2. Such physiologically acceptable buffers include, but are not limited to, phosphate buffered saline, phosphate buffered saline glucose, buffered saline and the like.

In vitro production of anti-peptide mAb is carried out by growing the hybridoma in DMEM containing about 2% fetal calf serum to obtain sufficient quantities. The in vitro produced mAb is purified by the same procedure as that for the ascites fluid. The monoclonal antibodies are further purified by affinity chromatography using a protein A SEPHAROSE chromatography matrix and the technique of Ey et al., *Immunochemistry* 15: 429–436 (1978) for IgG antibodies or a similar technique for other antibody isotypes. The purified monoclonal antibody, is neutralized with about 1M phosphate buffer at about pH 8.0 and stored as above.

Antibody titers of animal sera or monoclonal antibodies, antibody sensitivity, antibody specificity and the presence of and concentration of unknown antigens in body fluids are determined by various serological or immunological assays including precipitation, passive agglutination, enzyme-linked immunosorbent antibody (ELISA) technique, and radioimmunoassay (RIA) with RIA being preferred. Titer is defined herein as a measure of the concentration of antibody in a serum sample. The antibody titer of a given serum sample is related to the affinity of the antibody for the antigen. A serological or immunological assay is defined as a method of determining a specific component of a mixture or a specific amount of a known substance in which specific antigens or antibodies are used for the determination. Each assay includes the appropriate controls. The RIA is carried out in an assay buffer which may include, but is not limited to, buffered saline, phosphate buffer, phosphate buffered saline, Dulbecco's calcium-and magnesium-free buffered saline with Dulbecco's calcium-and-magnesium-free phosphate buffered saline (GIBCO) being preferred. The assay buffer may be used alone or preferably supplemented with about 0.1% gelatin, about 0.01% thimerasol and 1.0 mM ethylene-diaminetetraacetic acid (EDTA). Antiserum or monoclonal antibodies are prepared for antibody titer determination by dilution in the assay buffer. The initial dilutions are generally 1:1,000, 1:5,000 and 1:10,000.

Antigenic probes useful for antibody binding and titer determination include either synthesized or native specific antigen peptides containing the specific epitope. The peptides used as antigenic probes may contain only the specific amino acid epitope sequence or the amino acid antigenic sequences as depicted in Tables 2, 3, 4 and 5, modifications thereof, or they may include longer peptide units of the A alpha or gamma chain of fibrinogen which include the specific antigenic or epitope sequences and modifications. The antigenic probes may also include native peptides or synthesized peptides of as many as about 20 to about 30 amino acids but which also include the specific antigen or epitope sequence. Synthesized peptide probes are produced by the Merrifield technique, supra. Probes are selected or designed to be easily attached to a label or a tracer such as enzymes, fluorescent dyes, radioisotopes or haptens. The tracer or label allows for quantification of the serologic reaction. Synthesized peptides are designed to contain one or more additional amino acids which will allow the coupling of the label to the antigenic probe. Radioisotopes are the preferred label or tracer for the embodiments of this invention. Probe peptides are labeled with tritium ($^3H$), $^{14}$carbon ($^{14}C$), $^{125}$iodine ($^{125}I$) or $^{131}I$, with $^{125}I$ being preferred. To facilitate radioiodination each synthesized peptide is designed to contain one or more tyrosine residues, which may be part of the natural sequence, to allow coupling of the label to the antigenic probe. Radioiodination is accomplished using the chloramine T, iodogen or lactoperoxidase process with the chloramine T process being preferred. The labeled probed peptides are purified by reverse phase HPLC, size exclusion chromatography or ion exchange chromatography with HPLC being preferred. The amount of radioactivity per peptide is determined by procedures known in the art.

The radioactive probe is diluted in assay buffer to yield about 10,000 counts per minute (cpm) to about 30,000 cpm per aliquot, with about 20,000 cpm being preferred. The appropriate concentration of the specific probe is contacted with the diluted antibody. All determinations are made in duplicate. Following the contacting of the diluted antibody with the labeled probe, the mixture is incubated at about 4° C. for about 10 to about 20 hours. Non-antibody-bound radioactive probe is removed from the reaction mixture by chromatographic, precipitation, immunoprecipitation or adsorption techniques with adsorpotion of the unbound probe onto dextran-coated activated charcoal being preferred. The dextran-coated charcoal is prepared by suspending activated charcoal, USP, at about 3% (w/v) in 10 mM phosphate buffer, pH 7.5, containing about 0.25% (w/v) dextran, about 60,000 to about 90,000 average mol. wt., with about 70,000 average mol. wt., being preferred. The dextran-charcoal mixture is allowed to stand overnight, sedimented by centrifugation, washed once in dextran-containing phosphate buffer as above and centrifuged again. The dextran-coated activated charcoal is resuspended in the same buffer about to a 3% concentration. Immediately before use in the assay, the dextran-coated activated charcoal is diluted about 10-fold in Dulbecco's PBS and an amount sufficient to bind free probe is added to each sample. After a brief incubation period in a slurry of ice in water, the charcoal is sedimented by centrifugation and the supernatant fluid collected and counted in a gamma counter. Each assay includes charcoal-free controls, to which about 1 ml of PBS is added, for determination of total counts, and antibody-free controls for determination of non-specific binding. Percent specific binding at each antiserum dilution is determined by subtracting the value for non-specific binding from the value of antiserum binding and then dividing by the total counts per minute.

Sensitivity of the antisera is also determined by serologic assays, with RIA being preferred. The antiserum is diluted in an appropriate buffer, such as assay buffer, such that it binds about 15 percent to about 40 percent of the total radioactive probe, with about 25 percent being preferred. The same buffer is used for all dilution. The appropriate peptide antigen, complementary to the specific antibody, is diluted in assay buffer to approximate concentrations to yield about 1 pmole, about 0.1 pmole and about 0.01 pmole of peptide per assay aliquot. Complementary as used herein is defined as the specific amino acid sequence of an epitope that will specifically bind to an antibody raised specifically against that epitope resulting in an antiepitope antibody. The radioactive probe, $^{125}$I-labeled peptide complementary to the specific antibody, is diluted in assay buffer to yield about 10,000 cpm per assay aliquot. The assay includes antibody-free samples for determination of non-specific binding, and controls containing antibody and probe without unlabeled peptide, to determine the control level of probe binding. All determinations are made in duplicate.

Following the contacting of the diluted antibody with the labeled probe the mixture is incubated at about 4° C. for about 10 to about 20 hours. Antibody-bound radioactive probe is removed from unbound probe by chromatographic, precipitation, immunoprecipitation of adsorption techniques with adsorption of the unbound probe onto dextran-coated activated charcoal being preferred, as described above. Diluted dextran-coated activated charcoal is added to each sample. After a brief incubation period in a slurry of ice in water, the charcoal is sedimented by centrifugation and the supernatant fluid collected and counted in a gamma counter. The presence of non-labeled peptide inhibits the binding of labeled probe. The inhibition increases as the concentration of non-labeled peptide increases. The extent of inhibition at each level of peptide is calculated as the percent of the specific binding observed in the absence of unlabeled peptide. The sensitivity of antisera are compared by determining for each antiserum the 50% inhibitory concentration ($IC_{50}$) of the specific peptide and then comparing that to the value for the other sera. The $IC_{50}$ as used herein is defmed as the concentration of antigen producing 50 percent inhibition of probe binding.

Specificity of the individual antisera is also determined by serologic assays, with RIA being preferred, as described above. The antiserum is diluted in an appropriate buffer, such as assay buffer, to a concentration that binds about 15 percent to about 40 percent of the total radioactive probe, with about 25 percent being preferred. Various length probe peptides, which may contain at least the five amino acids adjacent to the amino or carboxyl cleavage sites of the Aα or gamma chain, including as a standard the specific peptide antigen complementary to the antiserum are diluted in assay buffer to yield amounts ranging from about $10^{-13}$ moles to about $10^{-6}$ moles in the assay aliquot. Controls will include probes which do not contain the specific epitope. The radioactive probe, $^{125}$-1-labeled peptide complementary to the specific antibody is diluted in assay buffer to yield about 5,000 cpm to about 25,000 cpm with a range of about 10,000 cpm to about 20,000 cpm being preferred per assay aliquot. The volume of each reactant in an assay may range from about 1 μl to about 1 ml, with about 100 μg being preferred. Specificity is determined by either an equilibrium assay or a non-equilibrium assay. In an equilibrium assay the specificity probes are diluted and contacted with a constant amount of antibody and further contacted with a constant amount of complementary labeled probe and incubated for about 10 to about 20 hours. In a non-equilibrium assay the specificity probes are diluted and contacted with a constant amount of antibody and incubated for about 2 to about 20 hours. After the initial incubation, the labeled probe is added and the samples are incubated for a second time for about 30 minutes to about 4 hours. The equilibrium assay is the preferred assay. The assay includes antibody-free controls to evaluate non-specific binding and controls containing antibody and probe without unlabeled peptide to determine the control level of probe binding.

Following the contracting of the antibody and the specificity probe and the subsequent addition of the labeled probe, the mixture is incubated at about 4° C. for about 10 to about 20 hours. Antibody-bound radioactive probe is separated from unbound probe by chromatographic, precipitation, immunoprecipitation or adsorption techniques, with adsorption of the unbound probe onto dextran-coated activated charcoal being preferred, as described above. After a brief incubation period in a slurry of ice in water, the charcoal is sedimented by centrifugation and the supernatant fluid, containing the antibody-bound probe, is collected and counted in a gamma counter. All techniques are known to the art.

The control level of probe binding is determined and the extent of inhibition at each concentration of specificity probe is calculated from the percent of the specific binding observed in the absence of specificity probe. The specificity of each antiserum is measured by comparing the levels of the various specificity probes which yield 50 percent inhibition of labeled probe binding. For a highly specific antiserum, much higher levels of specificity probe more than the specific one complementary to the antiserum will be required to yield 50 percent inhibition.

The monospecific antibodies, as identified and characterized above, are used to assay for the formation of the complimentary elastase cleavage product antigens or epitopes in whole blood or other body fluids, peritoneal fluid, sputum or broncheoalveolar lavage fluid. The assay for cleavage products is dependent upon the presence of leukocyte elastase in the sample. The preferred elastase is neutrophil elastase, but the embodiment of the invention includes all leukocyte elastases. The elastase may be released from leukocytes present in the sample fluid, as described below, or may be added to the assay by adding viable leukocytes or by the addition leukocyte extracts or purified elastase. The disease state will generally determine what fluid samples are necessary for the detection of elastase cleavage products. Blood and broncheovalveolar lavage fluid are the preferred fluids for following disease states; pulmonary emphysema, chronic bronchitis, cystic fibrosis, chronic obstructive pulmonary disease, bronchiectasis, adult respiratory distress syndrome, myelogenous leukemia and infantile respiratory distress syndrome. Blood and synovial fluid are the preferred fluids for the following diseases; arthritis and gout. The fluids of choice for glomerulonephritis are blood, urine and peritoneal fluid.

Aliquots of freshly-drawn blood or other body fluids including lavage washes which contain cells, are treated with an anticoagulant. Such anticoagulants include, but are not limited to, ammonium or potassium oxalate, disodium citrate, sequestrene, fluoride and heparin, with heparin being preferred. The samples are incubated in the presence of compounds capable of perturbing the cell membranes of leukocytes resulting in the release of intracellular elastase. Perturbation as used herein is defmed as a variation in or alteration of or deviation from the normal structural integrity of leukocyte cellular and vesicular membranes. Perturbating agents allow the release of intracellular enzymes, such as elastase, from intact cells by membrane alteration resulting in exocytosis or the like or may lyse the membranes and release the enzymes. Agents capable of membrane perturbation include, but are not limited to, zymosan, antigen-antibody complexes, complement C5a, N-formyl-L-methionyl-L-leucyl-L-phenylalanine (FMLP), phobol-12-myristate-13-acetate (PMA) plus cytochalasin B, n-formyl-L-norleucyl-L-leucyl-L-phenylalanine (FNLP) plus cytochalasin B and calcium ionophore A23187, platelet activating factor or any membrane perturbing agent which can alter the membranes of leukocytes resulting in the release of intracellular enzymes. The preferred agent for membrane perturbation is the calcium ionophore A23187 in concentrations ranging from about 75 μM to about 300 μM per aliquot. Prior to adding to the blood or body fluid, the calcium ionophore is dissolved in DMSO with the final concentration of DMSO in blood remaining constant at about 0.2%. Following incubation at about 37° C. for about 25 minutes, the blood or body fluid is centrifuged at about 2,000×g and the plasma or cell free body fluid is collected. The unique elastase cleavage products of fibrinogen in plasma or a cellular fluid can be assayed by the above procedure or the protein can be removed from the plasma by precipitation with chilled ethanol at a ratio of about 3:1 ethanol to plasma or fluid. The plasma-ethanol or fluid-ethanol mixture is centrifuged at about 3,000×g, the supernatant fluid collected and evaporated to dryness in a Speed-vac concentrator. The treated plasma or fluid is reconstituted to original volume with distilled water and samples are assayed for the presence of the unique elastase cleavage products of fibrinogen by an assay procedure capable of detecting the specific antigens or epitopes. As the concentration of calcium ionophore A23187 increases the amount of cleavage product increases until it reaches a maximum at an ionophore concentration of about 150 μM.

Fluid samples which do not contain neutrophils can also be assayed in a similar manner. These samples may be treated with a standard concentration of neutrophils and then treated with a perturbing agent or they may be treated with a standard amount of purified elastase. The fluids, cells and elastase in most situations would be homologous.

Elastase cleavage products can be identified and the concentration determined by a variety of immunoassays, which include but are not limited to: immunoradiometric assays, employing labeled antibodies, Miles and Hales, *Nature* 219: 186-(1968) or a sandwich variant according to Addison and Hales, *Hormone Meta. Res.* 3: 59-(1971); enzyme immunoassays, employing competitive assays with antigen-enzyme conjugates according to the method of Van Weeman and Schours, *F.E.B.S. Lett.* 15: 232-(1971) or enzyme-labeled antibody assays according to the procedure of Envall and Perlmann, *Immunochem.* 8: 871-(1971) or a variant of the enzyme-labeled antibody assay which employs detection by a second antibody according to the process of Hammarstrom et al., *Proc. Natl. Acad. Sci. USA* 72: 1528-(1975) or non-competitive sandwich (ELISA) methods, see Nakamura et al., in *Handbook of Experimental Immunology*, Vol. 1, "Immunochemistry", D. M. Weir, ed. 4th Edition (1986), Blackwell Scientific Publications, Oxford, pp. 27.1–27.20: or labeled antigen (RIA) as described above or any other assay which will determine antigen concentration. The preferred assay is the RIA as generally described above and in more detail hereinafter. The total volume of the assay fluid may range from about 5 $\mu$l to about 1 ml with about 100 $\mu$l to about 500 $\mu$l being preferred. Standard solutions or known or unknown cleavage products are prepared assay buffer, as described above, in the range of about $1\times10^{-10}$ M to about $2\times10^{-8}$ M which represents amounts of peptide ranging from about 0.01 picomoles to about 2.0 picomoles in an appropriate volume, about 100 $\mu$l of buffer. The standard solutions or dilutions of unknown samples are contacted with an antibody solution. The antibody solution may contain one or more monospecific antibodies specifically reactive with the antigens listed in Tables 2, 3, 4 and 5 or antibodies reactive with any epitope listed in the Tables on any length fragment of fibrinogen. The antibody solution is generally at a concentration sufficient to give a positive reaction, usually about a 1:1000 dilution of serum in an appropriate buffer such as assay buffer. The samples containing antigen and antibody are mixed and a labeled probe complementary to the specific antibody or antibodies is added. A radioactive probe or probes will be diluted in an appropriate buffer, assay buffer, to yield about 10,000 to about 25,000 cpm per about 100 $\mu$l of buffer. Each assay includes antibody-free controls to measure non-specific binding and controls containing antibody plus probe without added standard or unknown to determine the control level of peptide binding.

Following the contacting of the diluted antibody with the labeled probe, the mixture is incubated at about 4° C. for about 10 to about 20 hours or at about 37° C. for about 10 minutes to about 2 hours. Antibody-bound radioactive probe is separated from unbound radioactive probe by chromatographic, precipitation, immunoprecipitation or adsorption techniques with adsorption of the unbound probe onto dextran-coated activated charcoal being preferred, as described above. Diluted dextran-coated activated charcoal is added to each sample. After a brief incubation period in a slurry of ice in water, the charcoal is sedimented by centrifugation and the supernatant fluid collected and counted in a gamma counter. Each assay includes charcoal-free controls for determination of total counts and antibody-free controls for determination of non-specific binding. The antibody-free control and the zero-peptide antibody control are counted in a gamma counter to determine the 0% bound and 100% bound values respectively. The assay standards are counted and related to the antibody control to determine the percent probe bound, and a standard curve is generated. When the percent bound is plotted as a function of the logarithm of the amount of peptide in the standard, a sigmoidal curve is generated which is close to linear between the limits of about 80% of control to about 20% of control. Unknowns are counted, their percent of control calculated, and they are compared to the standard curve to determine the amount of peptide present in the sample. Only those unknowns counting between about 80% and about 20% of control binding are considered valid.

The above defined assay technology is used to monitor the activity of human elastase inhibitors of human leukocyte elastase activity in human and primate blood. Generally an elastase inhibitor is combined with whole blood or given to primates or humans and the effect of leukocyte elastase on fibrinogen is determined. Replicate aliquots of freshly-drawn heparinized whole human blood are prepared with concentrations of elastase inhibitor ranging up to about 300 $\mu$g/ml. Following a brief pre-incubation with the incubator, a membrane perturbator, such as calcium ionophore A23187, is added at a concentration of between about 75 $\mu$M and about 300 $\mu$M. Non-membrane perturbator controls containing blood and perturbator-only controls are included to measure the extent of uninhibited peptide generation. All assay samples are incubated at about 37° C. for about 25 minutes. The plasma is then prepared and assayed fibrinogen cleavage products as described above. Elastase inhibitors are capable of inhibiting the generation of fibrinogen cleavage products and the levels of inhibition are easily detected using this novel assay system.

In vivo inhibition of fibrinogen cleavage products following treatment of primates with an elastase inhibitor is evaluated. Blood or fluid samples are collected both before and after treatment with either an elastase inhibitor or saline. Each heparinized blood sample is divided into about 4 aliquots (about 1 ml) and processed as described above. Treatment of an animal with an elastase inhibitor causes a marked reduction in the amount of elastase cleavage product produced.

The ability of the novel assay to determine the presence of the unique fibrinogen cleavage products and to determine the relative amounts of these products is evaluated with blood from individuals genetically deficient in alpha 1-proteinase inhibitor ($\alpha$1Pi), a normal serum elastase inhibitor. Individuals deficient in $\alpha$1Pi, exhibit the PiZZ phenotype, and produce less than normal levels of circulating $\alpha$1Pi which is a natural inhibitor of leukocyte elastase, Janoff, *Am. Rev. Respir. Dis.* 132: 417–433 (1985). Consequently individuals exhibiting the PIZZ phenotype would not have the capacity to inhibit elastase activity and they should have increased fibrinogen cleavage products when assayed by the above procedure. When heparinized blood is collected from individuals who possess the PiZZ phenotype and processed as described above and levels of specific cleavage peptide antigen are measured, they are higher than normal volunteers.

The components of the assay described herein can easily be assembled into a package or kit. For example, the components can be used to coat the surface of a substratum or solid carrier. Suitable carrier materials include cellulose, cross linked dextrose, silicone rubber, microcrystalline glass, and a wide variety of plastics. The most common types of carriers or substratum are plastics including but not limited to polyethylene, polyvinyl chloride, polyamides, polystyrene, polypropylene and other polymers. The carrier or substratum can be formed into various shapes including but not limited to tubes, dishes, plates, multiwell plates, beads or any vessel. The assay components may be covalently bonded to the carrier or substratum, cross-linked, or physically coupled thereto. A variety of detection techniques may be utilized in the assay kit of the present invention, including but not limited to, a colorimetric detection, fluorescence detection, ultraviolet radiation detection, and isotope detection. Kits suitable for immunodiagnosis, or for any other purpose described herein containing the appropriate reagents are constructed by packaging the appropriate materials, including the antibodies of the present invention, in a suitable container along with the remaining reagents and materials required for the assay. A set of instruction should be included.

The following examples illustrate the present invention without, however, limiting the same hereto.

EXAMPLE 1

Primary Cleavage of Human Fibrinogen By Human Leukocyte Elastase

Purified human fibrinogen (Sigma) was combined with human neutrophil elastase (Elastin Products), at the ratio of 200 moles fibrinogen/mole human neutrophil elastase in Tris-buffer, pH 7.0 in a final volume of 1.0 ml. Samples of the reaction mixture were incubated at 37° for 5, 15, 30, 45 and 60 minutes. The reaction was stopped by the addition of 3 volumes of ice-cold ethanol (3° C.) incubated at that temperature for 30 minutes. Following incubation the samples were centrifuged at 3,000×g at 3° C. for 20 minutes, the supernatant fluid was removed and placed in clean tubes and the samples concentrated to dryness in a Speed-Vac overnight. Each sample was reconstituted in high performance liquid chromatography HPLC buffer consisting of a mixture of water and acetonitrile and chromatographed on a DUPONT-ZORBAX™ C-18 chromatogrphy column (0.4× 25 cm). A linear gradient was developed over a 75 minute interval in $H_2O$:acetonitrile:trifluoroacetic acid, 95:5:0.2 v/v/v, to $H_2O$:acetonitrile:trifluoroacetic acid, 60:40:0.2 v/v/ v. peptide peaks emerging from the column were collected, rechromatographed to prove purity and subjected to N-terminal amino acid sequence analysis on an Applied Biosystems Protein Peptide Sequencer, Model 470A, following the manufacturer's procedures.

A 15 minute incubation time allowed the best resolution of fibrinogen cleavage products. Eight major peaks and nineteen minor peaks were identified. The major peaks represent the primary cleavage products and the minor peaks represent the minor or secondary cleavage sites. Amino acid sequence analysis of the major peptide peaks allowed the identification of nine elastase cleavage sites in human fibrinogen. Six of the cleavage sites reside in the A alpha chain while three sites are located in the gamma chain, see Table 1.

EXAMPLE 2

Synthetic Peptide Antigens

Knowing the specific elastase cleavage sites on both the A alpha and gamma chain of human fibrinogen allowed the identification of antigenic peptides and peptide probes representing the amino and carboxyl termini adjacent to the cleavage sites. The specific amino acid sequences associated with carboxyl termini are illustrated in Tables 2 and 3 while the sequences associated with the amino termini are illustrated in Tables 4 and 5.

Peptide antigens and peptide probes were synthesized using t-Boc chemistry on a SAM TWO Peptide Synthesizer (Biosearch, Inc.) and an Applied Biosystems (Model 430) peptide synthesizer. The peptides terminating in a carboxyl group were synthesized on the standard Merrifield resin. The synthesis procedure is described in detail in the SAM TWO Peptide Synthesizer Operator's Manual (Biosearch, 1985). Cleavage of the peptide from the resin was accomplished by treatment with hydrogen fluoride in a Protein Research Foundation hydrogen fluoride apparatus following procedures outlined in the SAM TWO Operator's Manual. Correct molecular ions were obtained by fast atom bombardment spectral analysis for each peptide. The peptides were purified by HPLC using an alkyl silane substrate with 18 carbon atoms (C18) as described in the SAM TWO Operator's Manual. Purity of the individual peptides was assessed by reversed phase HPLC and amino acid analysis, again following set procedures as described in the SAM TWO Operator's Manual. Correct molecular ions were obtained by fast atom bombardment mass spectral analysis for each peptide. The primary antigen associated with the carboxyl terminus for the Val (21) Glu (22), see Table 1, elastase cleavage site of the A alpha chain, Gly (17)-Pro-Arg-Val-Val (21), (SEQ. ID. NO.:15) is synthesized with two additional amino acid residues. The cysteine-norleucine is attached to the Aα 17–21 antigen to give the following antigen: Cys-Nle-Gly-Pro-Arg-Val-Val. The integrity of the carboxyl group on the terminal valine residue was unaltered. The cysteine is a linking amino acid because it allows the antigen to be linked or attached to an immunogenic carrier. The norleucine was added as an internal marker to determine the actual number of antigen molecules attached to a single immunogenic carrier. The 360 immunogen has the following sequence: Cys-Nle-(355)Thr-Ser-Glu-Ser-Ser-Val (SEQ. ID. NO.:43) (360).

EXAMPLE 3

Attachment of Antigen to Carrier

Attachment of the antigenic peptides of Example 2 to the carrier protein was carried out according to a modification of the method of Lemer et al., Proc. Nat. Acad. Sci. USA 78: 3403–3407 (1981) using either of the heterobifunctional coupling reagents, MBS or Sulfo-MBS (Price Chemical Co.). The peptide antigen is attached to the carrier bovine serum albumin (BSA), by combining 10 mg BSA dissolved in 2.5 ml phosphate buffer, 20 mM, pH 7.0 with 4.2 mg Sulfo-MBS and incubating for 30 minutes at room temperature with stirring. The Aα360 immunogen was coupled to thyroglobulin. The carrier-coupling reagent mixture was then applied to a PD-10 disposable SEPHADEX™ chormatography gel G-25 column (Pharmacia) which had been equilibrated with de-gassed 50 mM phosphate buffer, pH 6.0. The material which eluted from the column during sample application corresponded to the void volume of the column and was discarded. A small vial containing 6 micromoles of the purified, lyophilized peptide antigen was placed under the column outlet and the activated albumin was eluted into the vial with an additional 3.5 ml of the pH 6.0 buffer. The peptide antigen-activated carrier complex was allowed to react overnight. The antigen-carrier complex was purified by a second gel filtration as previously described, dialyzed against three changes of distilled water and lyophilized.

The degree of coupling was determined by amino acid analysis following hydrolysis of 0.5 mg of the lyophilized conjugate in 1 ml of 6.0 N HCl maintained at 110° C. for 24 hours. The sample was subjected to amino acid analysis with ninhydrin detection. The analysis showed that there were 11 moles of antigen peptide per mole of BSA.

EXAMPLE 4

Production of Monospecific Antibody

New Zealand White Rabbits and Hartley outbred guinea pigs were immunized with the immunogen of Example 3.

Multiple intradermal (ID) injections based on the method described by Vituakaitis, *Meth. Enzymol.* 73: 46–52 (1981) were employed. The initial immunizations employed 1 mg of the immunogen conjugate per ml saline homogenized with 1 ml Freund's Complete adjuvant. Rabbits received a total of 2 ml divided over 20 ID sites while guinea pigs received 1 ml. Animals were boosted 30 days later. Rabbits received 0.5 mg immunogen per ml saline, homogenized with 1 ml Freund's Incomplete adjuvant while guinea pigs received 0.25 mg immunogen. The boost was divided between an intramuscular and subscutaneous site. Frequent analytical bleeds were taken in order to assess the titer and sensitivity of the antisera. The antibody titer was allowed to fall almost to basal levels before re-boosting. Ten days after the final booster immunization, the animals were bled, the serum was collected and the serum was frozen and stored at −70° C.

EXAMPLE 5

Synthetic Probes

Antigen probes to determine antibody specificity and to evaluate the presence of and amounts of fibrinogen cleavage products were synthesized by the process of Example 2. Antigenic probes used to determine the presence of and amounts of cleavage products were designed to include a tyrosine residue at the terminus distal to the epitope so that the probe could be coupled to $^{125}$I. The initial probe used to determine antibody titer consisted of the first 21 amino acids of the A alpha chain plus an amino terminal tyrosine residue.

```
                1
H2N-Tyr-Ala-Asp-Ser-Gly-Glu-Gly-Asp-Phe-Leu-Ala-Glu-Gly-Gly-    (SEQ ID NO:44)
                        21
Gly-Val-Arg-Gly-Pro-Arg-Val-Val-COOH
```

Specificity probes used to evaluate antibody specificity and to demonstrate that specificity resided in the Aα 17 to 21 amino acid sequence included the following:

```
            1
H2N-Ala-Asp-Ser-Gly-Glu-Gly-Asp-Phe-Leu-Ala-Glu-Gly-Gly-        (SEQ ID NO:45)
                        21
Gly-Val-Arg-Gly-Pro-Arg-Val-Val-COOH

5
H2N-Glu-Gly-Asp-Phe-Leu-Ala-Glu-Gly-Gly-Val-Arg-Gly-Pro-        (SEQ ID NO:46)
                21
Arg-Val-Val-COOH 9                                         21
H2N-Leu-Ala-Glu-Gly-Gly-Val-Arg-Gly-Pro-Arg-Val-Val-COOH        (SEQ ID NO:47)

12                              21
H2N-Gly-Gly-Gly-Val-Arg-Gly-Pro-Arg-Val-Val-COOH                (SEQ ID NO:48)

14                        21
H2N-Gly-Val-Arg-Gly-Pro-Arg-Val-Val-COOH                        (SEQ ID NO:49)

15                      21
H2N-Val-Arg-Gly-Pro-Arg-Val-Val-COOH                            (SEQ ID NO:50)

17              21
H2N-Gly-Pro-Arg-Val-Val-CONH2                                   (SEQ ID NO:51)

1
H2N-Ala-Asp-Ser-Gly-Glu-Gly-Asp-Phe-Leu-Ala-Glu-Gly-Gly-        (SEQ ID NO:52)
                            22
Gly-Val-Arg-Gly-Pro-Arg-Val-Val-Glu-COOH

1
H2N-Ala-Asp-Ser-Gly-Glu-Gly-Asp-Phe-Leu-Ala-Glu-Gly-Gly-        (SEQ ID NO:53)
                        20
Gly-Val-Arg-Gly-Pro-Arg-Val-COOH

1
H2N-Ala-Asp-Ser-Gly-Glu-Gly-Asp-Phe-Leu-Ala-Glu-Gly-Gly-        (SEQ ID NO:54)
                    19
Gly-Val-Arg-Gly-Pro-Arg-COOH
```

```
                                            -continued
H2N-Ala-Asp-Ser-Gly-Glu-Gly-Asp-Phe-Leu-Ala-Glu-Gly-Gly-        (SEQ ID NO:55)

18
Gly-Val-Arg-Gly-Pro-COOH

1
H2N-Ala-Asp-Ser-Gly-Glu-Gly-Asp-Phe-Leu-Ala-Glu-Gly-Gly-        (SEQ ID NO:56)

16
Gly-Val-Arg-COOH
```

Radioiodination of the assay probe was accomplished by reaction with chloramine T. The peptide probe was dissolved in water at a concentration of 220 µg/ml. A 50 µl, volume of this solution (containing 11 µg) was added to 10 µl of 0.5 M phosphate (K⁺) buffer and then combined with 2 mCi of $^{125}$I Na and 10 µl (0.1 mg/ml) freshly prepared chloramine T in water. The mixture was allowed to react for 30 seconds and the reaction was stopped with 10 µl of 1 mg/ml NaI plus 1 mg/ml sodium thiosulfate. The radioiodinated probe was purified by HPLC using a Supelco C-8 column (0.4×25 cm). The iodinated probe was eluted by a 30 minute 2% per-minute gradient of 90% eluant A-10% eluant B to 30% eluant A-70% eluant B at a flow rate of 1 ml per minute. Eluant A consisted of 0.1% trifluoroacetic acid in water and eluant B consisted of 0.1% trifluoroacetic acid in acetonitrile.

EXAMPLE 6

General Immunoassay Protocol

The assay was conducted in a total volume of 300 µl of Dulbecco's calcium-and-magnesium-free phosphate buffered saline supplemented with 0.1% gelatin, 0.01% thimerosal and 1.0 mM EDTA. To 100 µl of buffer or sample were added 100 µl each of antiserum and radioactive probe diluted in the same buffer. The dilution of radioactive probe was prepared such that 15,000 to 20,000 cpm are added to each sample or control. The assay was incubated overnight at 4° C. and terminated by the addition of 0.3% dextran-coated charcoal. After sedimentation of the charcoal by centrigfugation, the supernatant fluid was decanted and the amount of radioactivity determined.

Antiserum titers were determined in this protocol by varying the dilution of the antiserum added in the 100 µl volume. The antibody dilution used in competition experiments was selected to yield approximately 30% binding of the radioactive probe. Antibody sensitivities were determined using samples containing different known amounts of the Aα 1–21 peptide. Specificites were determined by comparing the displacement curve generated by Aα 1–21 peptide to those generated by putative crossreactive peptides. The concentration of peptide in unknown samples was determined by relating the percent of control antibody binding of probe obtained in the presence of sample to a standard curve generated using know concentrations of peptide.

EXAMPLE 7

Determination of Antibody Binding

The antibody titer for the most active rabbit antisera, Example 4, against the peptide antigen of Example 1 were determined using a radioimmunoassay. The antisera were diluted in assay buffer, see Example 6, with dilutions ranging from 1:3,000 to 1:30,000 per 100 µl. The diluted antibody was contacted with Aα 1–21 radiolabeled probe, see Example 3, containing the appropriate antigenic peptide sequence, Gly-Pro-Arg-Val-Val (SEQ. ID. NO.:57), 100 µl. The radioactive probe was diluted in assay buffer to yield approximately 13, 000 cpm per 100 µl aliquot. The assay volume was made up to 300 µl by the addition of 100 µl assay buffer. All determinations were made in duplicate.

After overnight incubation of 4° C., antibody-bound and unbound radioactive probe were separated by adsorption of the unbound probe onto dextran-coated charcoal. Dextran-coated charcoal was prepared by suspending activated charcoal, USP, at a 3%, w/v, concentration in 10 mM phosphate buffer, pH 7.5, containing 0.25%, w/v, T-70 dextran, 70,000 average molecular weight (Pharmacia). The mixture was allowed to stand overnight was sedimented by centrifugation, washed once in dextran-containing phosphate buffer as above, and was then resuspended to a 3% concentration in the dextran-containing assay buffer. Immediately prior to use in the assay, the dextran-coated charcoal was diluted 10-fold in Dulbecco's PBS and 1 ml is added to each assay tube. After an incubation period of 30 minutes in an ice/water slurry, the charcoal was sedimented by centrifugation at 3,000×g for 10 minutes and the supernatant fluid was decanted and counted in a gamma counter. The assay included charcoal-free controls, to which 1 ml PBS was added, for determination of total counts and antibody-free controls for determination of non-specific binding. The percent specific binding at each antiserum dilution was determined by subtracting the antibody-free, or non-specific binding value from each value for antibody binding, and dividing that by the total counts in the system. The results are shown in the following table.

TABLE 6

| Percent Specific Antibody Binding | | |
|---|---|---|
| Antiserum Dilution | $^{125}$I-CPM | Percent Specific Binding |
| 3,000 | 3,700 | |
| | 3,828 | 26.5 |
| 15,000 | 1,134 | |
| | 1,109 | 6.5 |
| 30,000 | 717 | |
| | 787 | 3.7 |
| Total | 12,980 | |
| | 13,454 | — |
| Non-specific | 243 | |
| | 273 | — |

Rabbit antiserum designated number 20, at a final dilution of 1:3000 binds 26 percent of the total radioactive probe. This antibody concentration is more than sufficient for determining the presence of specific cleavage peptide.

EXAMPLE 8

Determination of Antibody Sensitivity

Antibody sensitivity was determined by evaluating the ability of various concentrations of unlabeled probe to inhibit binding to the radioactively labeled probe. The antiserum, Example 4, was diluted in the assay buffer, Example 6, to a concentration of 1:1,000 and 100 μl was used in each sample of the assay. The unlabeled probe, Aα 1–21, was diluted in assay buffer to give final concentrations of 1.0, 0.1, 0.01 picomoles per 100 μl. The radioactive probe $^{125}$I-tyrosyl-Aα 1–21 was diluted in assay buffer to yield approximately 10,000 cpm per 100 μl. The assay was set up in a total volume of 300 μl, with the volume made up where necessary with assay buffer. The assay included antibody-free controls to determine non-specific binding and controls containing antibody plus probe, without added specificity probe to determine the control level of probe binding. All determinations were made in duplicate. The assay samples and controls were processed and counted as described in Example 7. Percent control binding was determined by calculating the average cpm for the duplicate samples at each concentration of specificity probe, subtracting the average non-specific binding cpm, and dividing the results by the antibody-only counts. The results are shown in the following table.

TABLE 7

Sensitivity of Antibody

| Sample | $^{125}$I-CPM | Percent Control Binding |
|---|---|---|
| Amount of Unlabeled Probe (pmole) | | |
| 1.0 | 402 | |
|  | 416 | 10.5 |
| 0.1 and | 1,383 | |
|  | 1,393 | 57.1 |
| 0.01 | 2,243 | |
|  | 2,158 | 95.8 |
| Antibody only | 2,186 | |
|  | 2,390 | |
| Non-specific | 193 | — |
|  | 185 | |
| Total cpm | 9,564 | — |
|  | 9,498 | |

The sensitivity assay shows that the amount of Aα 1–21 peptide capable of inhibiting the binding of radiolabeled probe by 50 percent is approximately 0.1 picomole.

EXAMPLE 9

Determination of Antibody Specificity

Antibody specificity was determined by evaluating the ability of unlabeled peptides, specificity probes, of varying length, see Example 6, to inhibit the binding of the Aα 1–21 radioactive probe. Rabbit antiserum prepared against the Aα 17–21 immunogen described in Example 2 was diluted in assay buffer, see Example 6, at a dilution of 1:1,000. The specificity peptides of Example 5 were diluted in assay buffer at concentrations ranging from $1.6 \times 10^{-10}$ M to $1 \times 10^{-5}$ M. One hundred μl of each dilution was added to 100 μl of antiserum and 100 μl of radioactive probe. This represents specificity probe peptide in concentrations ranging from 0.016 picomoles to 1.0 nanomoles in the 100 μl aliquot used in the assay. The radioactive probe $^{125}$I-tyrosyl-Aα 1–21, see Example 5, was diluted in assay buffer to yield approximately 20,000 cpm per 100 μl aliquot, the amount used per sample or control. The assay was set up in a volume of 300 μl, with the volume made up where necessary with assay buffer. The assay included antibody-free controls used to determine non-specific binding and controls containing antibody plus probe to determine the control level of probe binding. All determinations were made in duplicate. After overnight incubation at 4° C., non-antibody-bound radioactive probe was separated form antibody-bound radioactive probe by adsorption onto dextran-coated activated charcoal as described in Example 7. The assay included charcoal-free control, to which 1 ml of PBS was added, for the determination of total counts.

The antibody-free control and the zero-peptide antibody control are counted to determine the 0% bound and the 100% bound values respectively. Radioactivity was determined using a gamma counter and standard techniques known in the art. The samples containing the test peptides are then counted and the amount of radioactivity associated with the antibody-free control subtracted from each. The resulting net counts are divided by the net counts in the antibody-only control to determine the percent bound in the presence of each amount of peptide. The following table shows the amount of each specificity probe necessary to inhibit antibody binding of labeled probe by 50 percent.

TABLE 8

Antibody Specificity

| Specificity | Inhibitory Concentration (IC50) picomoles | |
|---|---|---|
| Probe | Rabbit (#20) | Guinea Pig (#3) |
| Aα 1-21 | 0.1 | 0.1 |
| Aα 2-21 | 0.1 | — |
| Aα 9-21 | 0.1 | — |
| Aα 12-21 | 0.1 | — |
| Aα 14-21 | 0.2 | — |
| Aα 15-21 | 0.2 | — |
| Aα 17-21 | 1.6 | 10 |
| Aα 17-21-NH$_2$ | >1000.0 | 5000 |
| Aα 1-22 | >1000.0 | — |
| Aα 1-20 | 600.0 | — |
| Aα 1-19 | 800.0 | — |
| Aα 1-18 | >1000.0 | — |

The table lists the amount of each peptide required to inhibit radioactive probe binding by 50 percent, the inhibitory concentration. Only those specificity peptides which have the entire Aα 17–21 carboxyl sequence cross-react with the labeled probe Aα 1–21. It should be noted that the amidated analog of Aα 17–21 is not cross-reactive.

EXAMPLE 10

Immunoassay Protocol for the Determination of Aα 17–21 Epitope Containing Peptide Concentration In Unknown Samples The radioimmunoassay was conducted in a total volume of 300 μl with all dilutions carried out in assay buffer, Example 6. Standard solutions were prepared at concentrations in the range of $1 \times 10^{-10}$M to $2 \times 10^{-8}$M which represents amounts of peptide ranging from 0.01 picomoles to 2.0 picomoles in the 100 μl aliquot used in the assay. The assay included antibody-free controls to measure non-specific binding, and controls containing antibody and probe without added standard samples or unknown samples to determine the control level of peptide binding. To 100 μl of buffer, standard sample or unknown was added, 100 μl of specific antiserum from Example 2 and 7, diluted 1:1,000 in assay buffer. This was followed by the addition of 100 μl of radioactive probe, $^{125}$I-Tyrosyl-Aα 1–21 fibrinogen peptide, diluted in assay buffer to yield approximately 15,000 to 20,000 cpm per 100 μl aliquot. The assay was incubated overnight at 4° C. and the non-antibody-bound radioactive probe was separated form antibody-bound probe by adsorption onto dextran-coated activated charcoal, see Example 7. Each assay included charcoal-free controls, to which 1 ml PBS was added for the determination of total counts. Radioactivity was determined using a gamma counter and standard techniques known in the art.

The antibody-free control and the zero-peptide antibody control were counted to determine the 0% bound and 100% bound values respectively. The assay standards are then counted and divided by the antibody control to determine the percent bound and a standard curve was generated. When the percent bound is plotted as a function of the logarithm of the amount of peptide in the standard, a sigmoidal curve is generated which is close to linear between the limits of 80% bound and 20% bound. Unknowns are counted, their percent of control calculated and they are compared to the standard curve to determine the amount of peptide present in the sample. Only those unknowns with values between 80% and 20% of control binding are considered valid.

In Vitro Production of Cleavage Epitope
Containing Peptide Aα 17–21 In Human Blood.
Effect of Inonophore Concentrations Duplicate 1.0 ml aliquots of freshly-drawn heparinized vaccutainers containing 50 u per ml whole human blood were incubated for 15 minutes at 37° C. in the presence of calcium ionophore A23187 at concentrations ranging up to 200 μM. The calcium ionophore was dissolved in dimethyl sulfoxide (DMSO) with the DMSO concentration in blood kept constant at 0.2%. Following incubation the aliquots were placed on ice, centrifuged and the plasma collected. Plasma aliquots (400 μl) were removed and placed in 12×75 mm glass tubes and 1200 μl chilled ethanol was added to precipitate the protein. The sample was centrifuged and 800 μl of the supernatant fluid was removed and evaporated to dryness in a Speed-vac concentrator. The sample was reconstituted to original plasma volume with 200 μl of distilled water. Duplicate 100 μl aliquots were assayed for Aα 17–21 epitope containing peptide (Aα 1–21) as described in this Example. The following table shows the amount of Aα 17–21 epitope containing peptide produced in response to by various amounts of ionophore.

TABLE 9

Ionophore Stimulated Production of Aα 17-21 Epitope Containing Peptide From Whole Human Blood

| Ionophore Concentration (μM) | Aα 17-21 Epitope Containing (picomoles per ml blood) |
|---|---|
| 0 | 0 |
| 5 | 1.2 |
| 15 | 1.6 |
| 25 | 2.6 |
| 50 | 2.8 |
| 100 | 4.0 |
| 150 | 4.1 |
| 200 | 3.8 |

The optimal production of Aα 17–21 epitope-containing peptide occured following stimulation with 150 μM of calcium ionophore A23187.
Ionophore Incubtion Time Calcium ionophore A23187 was added to replicate 1.0 ml aliquots of freshly-drawn heparinized whole blood as described above, to a final concentration of 150 μM. Additional control aliquots of blood received DMSO at a concentration of 0.2%. The blood aliquots were incubation at 37° for various time intervals ranging up to 60 minutes. Following the incubation, plasma was prepared, processed and assayed as above. The are shown in the following table.

TABLE 10

Time dependent Production of Aα 17-21 Epitope Containing Peptide From Whole Blood By Ionophore A23187

| Incubation Time minutes | Aα 17-21 Epitope (picomoles/ml plasma) |
|---|---|
| <1.0 | 0.7 |
| 2.5 | 2.3 |
| 7.5 | 2.8 |
| 10.0 | 3.5 |
| 15.0 | 3.7 |
| 20.0 | 3.7 |
| 25.0 | 3.8 |
| 30.0 | 3.8 |
| 40.0 | 3.6 |
| 50.0 | 3.1 |
| 60.0 | 3.2 |

The concentration of Aα 17–21 epitope containing peptide increases with time and reaches a maximum concentration of between 3.5 and 4.0 mM between 10 and 40 minutes. Controls containing DMSO alone caused no peptide production. An incubation time of 25 minutes was selected for future experiments.

Other Membrane Perturbators

Other known membrane perturbators have been used to evaluate the in vitro production of the epitope containing cleavage peptide Aα 17–21 in human blood. Aliquots of freshly-drawn heparinized whole blood were incubated for 25 minutes at 37° C. in the presence of either 5 μg/ml cytochalasin B and concentrations of phorbol-12-myristate-13-acetate (PMA) ranging up to 20 μM or in the presence of the combination of 5 μg/ml cytochalasin B and concentrations of n-formyl-L-norleucyl-L-leucyl-L-phenylalanine (FNLP) ranging up to 20 μM. Plasma was collected, prepared and assayed as described above. The results are shown in the following tables.

TABLE 11

PMA And Cytochalasin B Stimulated Production of Aα 17-21 Epitope Containing In Whole Human Blood

| PMA μMolar | Aα 17-21 Epitope Containing Peptide Produced (picomoles/ml plasma) |
|---|---|
| 0.003 | 0.0 |
| 0.010 | 0.3 |
| 0.03 | 0.3 |
| 0.10 | 0.4 |
| 0.30 | 0.9 |
| 1.0 | 1.5 |
| 3.0 | 2.6 |
| 10.0 | 3.0 |
| 20.0 | 3.7 |

TABLE 12

FNLP And Cytochalasin B Stimulated Release of Aα 17-21 Epitope Containing Peptide From Whole Human Blood

| FLNP µMolar | Aα 17-21 Epitope Containing Peptide Produced (picomoles/ml plasma) |
|---|---|
| 0.001 | 0.0 |
| 0.003 | 0.0 |
| 0.010 | 0.0 |
| 0.03 | 0.4 |
| 0.1 | 0.9 |
| 0.3 | 1.1 |
| 1.0 | 1.1 |
| 3.0 | 1.3 |
| 10.0 | 1.2 |
| 20.0 | 1.3 |

EXAMPLE 11

Applications of Aα 17–21 Epitope-Containing Peptide Radio-immunoassay

The following descriptions illustrate that the fibrinogen peptide immunoassay can be used to monitor the effective activity of human leukocyte elastase in human blood.

Calcium Ionophore A23187-Stimulated Production of Fibrinogen Cleavage Peptide in The Blood of Normal Humans Heparinized venous blood was drawn from seventeen normal healthy volunteers on three occasions over a five week period. On each occasion, calcium ionophore A23187 was added to replicate aliquots of the freshly drawn blood to a final concentration of 150 µM. The blood was incubated at 37° for 25 minutes, the plasma collected and assayed for cleavage peptide. A representative example of the results are shown in the following table.

TABLE 13

Calcium Ionophore A23187 Stimulation of Fibrinogen Cleavage Product In Normal Human Blood

| | Picomoles Aα 17-21 $10^6$Neutrophils | | |
|---|---|---|---|
| Donor | Week 1 | Week 3 | Week 5 |
| 1 | 0.78 | 0.74 | 0.72 |
| 2 | 0.81 | 1.07 | 2.04 |
| 3 | 0.98 | 1.04 | 1.22 |
| 4 | 0.69 | 0.90 | 1.25 |
| 5 | 0.58 | 0.65 | 0.59 |
| 6 | — | 1.16 | 1.04 |
| 7 | — | 0.88 | 1.21 |
| 8 | — | 0.62 | 1.10 |
| 9 | — | 1.12 | 1.07 |
| 10 | 0.97 | 1.55 | 0.98 |
| 11 | — | 0.84 | — |
| 12 | — | 0.55 | — |
| 13 | 1.46 | 1.23 | 1.00 |
| 14 | 1.25 | 0.89 | — |
| 15 | 1.05 | 1.15 | 1.54 |
| 16 | — | 1.00 | 1.27 |

Normal individuals produced consistent amounts of fibrinogen cleavage peptide as determined by this assay. The dashed lines indicated that so sample was obtained from the individual at that time.

Effect of An Elastase Inhibitor on Calcium Ionophore A23187-Stimulated Production of Fibrinogen Cleavage Peptide In The Blood of Normal Humans The effect of the elastase inhibitor 3-Acetoxymethyl-1α-methoxy-6-oxo-5-thia-1-azabicyclo[4.2.0]oct-2-ene-2-(2-(S)carboxy-pyrrolidinecarboxamide)5,5-dioxide (Compound 1) on the calcium ionophore A23187-induced fibrinogen cleavage peptide production was evaluated. Replicate 2 ml aliquots of freshly-drawn heparinized whole human blood were prepared with concentrations of Compound 1 ranging up to 100 µl/ml. Following a brief pre-incubation of 5 minutes at 37° C., calcium ionophore A23187 was added to a final concentration of 150 µM. Non-ionophore containing blood and ionophore-only (no inhibitor) controls were included to measure the extent of uninhibited peptide generation. All aliquots were incubated at 37° C. for 25 minutes, the plasma collected, processed and assayed for fibrinogen cleavage peptide as described above. The results are shown in the following table.

TABLE 14

Elastase Inhibitor Activity Assay

| Elastase Inhibitor µg/ml | Cleavage Product Produced picomoles/ml | Percent Inhibition |
|---|---|---|
| 0 | 2.4 | 0 |
| 1 | 2.3 | 4 |
| 5 | 1.6 | 33 |
| 10 | 1.6 | 33 |
| 20 | 1.5 | 37 |
| 30 | 1.2 | 50 |
| 40 | 0.8 | 67 |
| 80 | 0.4 | 85 |

The results demonstrate that a known elastase inhibitor is capable of inhibiting the ionophore-induced formation of the elastase cleavage product in human blood. This is consistant with the observation that exposure of whole human blood to calcium ionophore A23187 results in stase cleavage product by allowing the release of neutrophil elastase.

Effect of An Elastase Inhibitor on Calcium Ionophore A23187-Stimulated Production of Fibrinogen Cleavage Peptide In Primate Blood Two chimpanzees were anesthetized and fitted with venous catheters for the collection of blood. Blood was collected from each animal at intervals over a 60 minute period prior to the administration of the elastase inhibitor. All blood samples were collected in heparin. After the intial 60 minute period one animal was given an intravenous injection of 10 mg/kg of the elastase inhibitor Compound 1 while the other animal received an equivalent volume of normal saline. Additional heparinzed blood samples were taken from both animals at regular intervals over the next 60 minutes. Each freshly-drawn sample of whole heparinized chimpanzee blood was divided into 4 aliquots. Calcium ionophore A23187 was added at a final concentration of 150 µM to two of the aliquots and an equivalent volume of the DMSO vehicle was added to the other two. All blood samples were incubated at 37° for 25 minutes, plasma collected and assayed as described above. The results are shown in the following table.

TABLE 15

Ionophore-Induced Production of Aα 17-21 Epitope Containing Peptide in Chimpanzee Blood Form An Elastase Inhibitor-Treated and Control Animal

| Time | A1-21 Peptide Produced (picomoles/ml plasma) | |
|---|---|---|
| (min) | Treated | Control |
| −60.0 | 2.70 | 0.80 |
| −45.0 | 3.50 | 1.00 |
| −30.0 | 3.10 | 0.81 |
| −15.0 | 3.00 | 0.95 |
| 0.0 | 3.00 | 0.98 |
| 1.0 | 1.10 | 1.20 |
| 2.5 | 1.30 | 1.10 |
| 5.0 | 1.60 | 0.97 |
| 7.5 | 2.00 | 1.10 |
| 10.0 | 1.80 | 1.20 |
| 12.5 | 1.70 | 1.10 |
| 15.0 | 0.98 | 1.50 |
| 20.0 | 1.90 | 1.50 |
| 30.0 | 2.20 | 1.20 |
| 40.0 | 3.10 | 1.50 |
| 50.0 | 2.60 | 1.20 |
| 60.0 | 2.50 | 0.96 |

Elastase inhibitor was infused into the treated animal at time 0.

The blood samples drawn from the treated chimpanzee after infusion of the elastase inhibitor produced markedly lower levels of the fibrinogen peptide in response to calcium ionophore A23187. Fibrinogen cleavage peptide was not detected in the non-ionophore treated blood samples from either animal. Over the course of 30 to 40 minutes, the amount of ionophore-stimulated peptide production in freshly-drawn samples gradually returned to the pretreatment level. No consistent change over time was observed in the untreated animal.

Calcium Jonophore A23187-Stimulated Production of Fibrinogen Cleavage Peptide in The Blood of Alpha-1 Proteinase Deficient Humans Heparinized venous blood was drawn from four individuals who process the PiZZ phenotype, deficient for alpha-1 proteinase inhibitor. Blood was also collected form two normal volunteers. Calcium ionophore A23187 was added to replicate aliquots of the freshly drawn blood to a final concentration of 150 µM. The blood was incubated at 37° for 25 minutes, the plasma collected and assayed cleavage peptide. The results are shown in the following table.

TABLE 16

Production of Aα 17-21 Epitope Containing Peptide In Whole Blood of PiZZ and Normal Individuals In the Presence of Calcium Ionophore

| Patient | Control | A23187 |
|---|---|---|
| Normal | <0.4 | 4.2 |
| Normal | <0.5 | 4.6 |
| PiZZ | <0.7 | 8.4 |
| PIZZ | <0.6 | 26.5 |
| PIZZ | <0.5 | 20.5 |
| PiZZ | <0.4 | 17.8 |

Values are expressed as pM Aα 17-21 epitope containing peptide produced per ml of plasma. The blood samples derived from the four individuals who were genetically deficient in alpha-1 proteinase inhibitor produced greater amounts of peptide than did those derived from the normal volunteers. Under basal conditions no fibrinogen cleavage products could be detected in the blood of any of the donors.

EXAMPLE 12

The Aα 17–21 epitope is one of several carboxyl terminus epotope peptides and antibodies to them are readily used to measure leukocyte elastase-derived fibrinogen cleavage product epitope-containing peptides in samples. Such a method may be described as follows:

A method for detecting leukocyte elastase-derived fibrinogen cleavage product epitope-containing peptides in body fluid samples containing leukocytes and fibrinogen, comprising the following steps:

a) combining the sample with an anticoaguled to form a mixture;

b) optionally, adding a leukocyte membrane perturbating agent to the mixture to release elastase from the leukocytes;

c) optionally, incubating the mixture under conditions that permit cleavage of the fibrinogen by the elastase to yield fibrinogen cleavage product epitope-containing peptides;

d) centrifuging the mixture to form a pellet and an epitope-containing supernatant;

e) collecting the supernatant;

f) adding at least one antibody to the supernatant to form an epitope-antibody mixture;

g) measuring the epitope-antibody mixture; and h) comparing the measurement of step g) to a standard;
wherein the fibrinogen cleavage product epitope containing peptides are selected from the group consisting of peptides terminating in A alpha 17–21 residues, A alpha 356–360 residues, and A alpha 564–568 residues;
wherein the antibody is reactive with fibrinogen cleavage product epitope containing peptides selected from the group consisting of peptides terminating in A alpha 17–21 residues, A alpha 355–360 residues, and A alpha 564–568 residues; and
wherein the antibody is nonreactive with uncleaved fibrinogen.

EXAMPLE 13

Synthesis of Peptides

Peptides were synthesized via the Merrifield solid-phase technique on an Applied Biosystems 430A peptide synthesizer using either tBoc or Fmoc chemistries. Using the tBoc syntheses, peptides were synthesized according to the manufacturer's recommended protocols for N-hydroxybenzotriazole ester couplings on phenylacetamidomethyl resins for peptide acids. Methylbenzylhydrylamine resin was used for peptide amides. The peptides were deprotected and cleaved from the resin with 90% hydrofluoric acid, 10% anisole at 0° C. for 1 hour and extracted from the resin with 10% acetic acid and lyophilized.

For Fmoc synthesis, the peptides were synthesized according to the manufacturer's suggested protocols for 2-(1-H-benzotriazole-1-yl)1,1,3,3, -tetramethyluronium-hexafluorophosphate mediated couplings on p-benzyloxybenzyl alcohol resins. The peptides were deprotected and cleaved from the resin with 90% trifluoroacetic acid (TFA), 5% thioanisole, 3% ethanedithiol and 2% anisole at room temperature for 2 hours. Crude peptides were precipitated with ethyl ether, dissolved in 10% acetic acid, lyophilized and purified by reverse phase HPLC on a Waters C18 Deltapak column. The column was eluted with a gradient of 5 to 50% acetonitrile in aqueous 0.1% TFA. All peptides were >95% pure as assessed by reverse phase HPLC on a Brownlee Spheri-ODS column with a gradient of 5 to 50% acetonitrile in aqueous 0.1% TFA. Molecular ions were obtained by electrospray ionization mass spectrometry or matrix-assisted laser desorption ionization time-of-flight mass spectrometry to confirm the structure of each peptide.

EXAMPLE 14

Immunogen/Hapten Coupling Chemistry

The immunogen $C(Nle)T^{355}SESSV^{360}$ (SEQ. ID. NO.:58) synthetic peptide was coupled to bovine thyroglobulin (Sigma) by the following method. Bovine thyroglobulin (33 nmoles) was dissolved in 2.5 ml of degassed 20 mM phosphate buffer, pH 7.0, and incubated with 10 mmoles Sulfo-MBS (Pierce Chemicals) for 30 minutes at room temperature. The mixture was next applied to a PD-10 column (9 ml bed volume from Pharmacia 17-0851-01) and the activated thyroglobulin was eluted with 3.5 ml of 50 mM phosphate buffer, pH 7.0 into a vial containing 6 mmoles of lyophilized peptide. This mixture was incubated overnight at 4° C. with stirring. The thyroglobulin-$C(Nle)T^{355}SESSV^{360}$ immunogen was separated from free unreacted peptide and reaction by-products by chromatography on a 9 ml bed volume PD-10 column eluted with PBS. The extent of peptide coupling was determined after acid hydrolysis (6 N HCl containing 0.1% phenol at 100° C.) for 24 hours followed by amino acid analysis using a Beckman Model 6300 amino acid analyzer.

EXAMPLE 15

Production of Antiserum

A rabbit polyclonal antiserum, designated R-770, was raised by Research & Diagnostic Antibodies, Richmond, Calif. Six New Zealand white rabbits were immunized with the thyroglobulin-C(Nle)TSESSV conjugate prepared as described above. The initial immunizations employed 1 mg of the immunogen conjugate per ml of saline homogenized with 1 ml of Freund's complete adjuvant. Rabbits received a total of 0.4 ml divided between two intramuscular sites. Animals were boosted 10 days later receiving 0.5 mg immunogen per ml of saline homogenized with 1 ml Freund's incomplete adjuvant. The boost was divided between an intramuscular and a number of subcutaneous sites. Thirty days later the animals were again boosted. Thereafter the rabbits were boosted every 20 days Ten days after each boost blood was taken and sera prepared to assess the titer. The antiserum used in these studies was from rabbit 770 second bleed and designated R-770 2nd bleed. The antiserum was diluted 1:1 with glycerol and stored at −20° C. The antiserum from the terminal bleed of rabbit 770 (66 ml) showed equivalent binding and competitive dilution kinetics with the standard peptide. In addition, an antiserum (68 ml) from rabbit 3065 (R-3065 terminal bleed) showed identical binding and competitive displacement Antisera is available for 1,224,000 assays slots.

EXAMPLE 16

Radioiodination of $^{125}$I-YRGSAGHATSESSV(SEQ. ID. NO.:1)$^{360}$ Probe

YRGSAGHATSESSV, which corresponds to residues 347 to 360 of the Aα chain of human fibrinogen, was radioiodinated utilizing the iodogen method by Research & Diagnostic Antibodies (Richmond, Calif.). Alanine was substituted for the naturally occurring tryptophan$^{354}$ of the standard peptide to prevent oxidation. This substitution, 7 amino acids distal to valine$^{360}$, does not impair antibody binding when compared to the binding of the natural peptide standard. Complete antibody recognition is achieved with the heptapeptide $W^{354}TSESSV^{360}$(SEQ. ID. NO.:5).

YRGSAGHATSESSV (SEQ. ID. NO.:1) (0.2 nmoles) was incubated for 12–15 minutes with 400–500 mCi Na$^{125}$I in an Iodogen (Pierce Chemical Co.) coated microfuge tube. The radiolabeled peptide was separated from the unreacted Na$^{125}$I by chromatography on a 5 ml bed volume G-10 SEPHADEX™ chromatograhy gel column eluted with 25% acetic acid containing 0.1% Triton X-100. The non-retained material, which contained the radiolabeled peptide, was lyophilized to dryness. The $^{125}$I-peptide was further purified on RP-HPLC. The peptide was reconstituted into a minimal volume of H$_2$O and injected onto a ZORBAX™ C18 chromatograhy matrix reverse phase column and eluted with an acetonitrile/H$_2$O gradient at 1 ml/min. Buffer A was 0.1% TFA in H$_2$O and buffer B was 0.1% TFA in acetonitrile. The column was eluted for 10 min with 90% buffer A/10% buffer B; for 10 min with a linear gradient to 70% buffer A/30% buffer B; and for 30 min with 70% buffer A/30% buffer B. Fractions of 500 ml, were collected and the radioactivity determined. The fractions containing the monoiodinated peptide, usually eluting in fractions 48–52, were combined and lyophilized to dryness in serum vials. The vials were stored at −20° C. until use. The final probe routinely had a specific activity of approximately 2,000 Ci/mmole.

EXAMPLE 17

Competitive Radioimmunoassay for Aα(Val$^{360}$)

A 10-X stock buffer solution containing 250 mM EDTA and 0.1% thimerasol is prepared in 1-X calcium and magnesium free Dulbecco's phosphate-buffered saline (PBS) (Gibco Cat. No. 14190-045). The RIA buffer (Aα(Val$^{360}$) PET/GEL) is prepared by diluting 100 ml of the stock solution to 1 L with H$_2$O and by addition of gelatin to a final concentration of 0.1% (W/V). The pH was adjusted to 7.4±0.1. The assay is conducted in a total volume of 300 μl of this buffer. One hundred microliters of Aα(Val$^{360}$)Pet/Gel buffer or sample diluted in this buffer were mixed with 100 μl of anti-TSESSV(SEQ. ID. NO.:59)R-770 antiserum (final dilution 1:18,000) and 100 μl of the $^{125}$I-probe (~30,000 CPM) and incubated overnight at 4° C.

The synthetic peptide YRGSAGHWTSESSV (SEQ. ID. NO.:1)was used to generate the standard curve. This peptide contained the natural sequence of Aα(Tyr$^{347}$–Val$^{360}$) and differed from the $^{125}$I-probe in which an Ala$^{354}$ replaced Trp$^{354}$. A 200 nM stock solution of standard peptide was prepared in Aα(Val$^{360}$) PET/GEL buffer and stored frozen at −20° C. In each experiment 12 concentration standards (0.01–20 pmoles/100 μl) were prepared by serially diluting 100 g aliquots of the stock solution 1:2 in Aα(Val$^{360}$) PET/GEL buffer 11 times. Therefore, the standard curve concentrations of peptide were 0.01, 0.02, 0.04, 0.08, 0.16, 0.31, 0.625. 1.25, 2.5, 5.0, 10.0 and 20.0 pmoles/100 μl. Tubes without standard (to measure the total amount of antiserum binding) and tubes without antiserum (to measure the total amount of radioactivity added and background) were also included. All determinations were performed in duplicate.

The antibody-bound radiolabeled probe was separated from unbound radiolabeled material by an anti-rabbit-IgG antibody attached to magnetic beads. A suspension of BioMag beads (Goat anti-rabbit IgG (H&L) (PerSeptive Diagnostics, Cambridge Mass.) was diluted 1:2 just prior to use with PBS. One ml aliquots of the suspension were added to all tubes, except tubes not containing antiserum which were used for the determination of total radioactivity, and incubated at room temperature for 5 minutes. During the 5 minute incubation period, the tubes containing beads were transferred to a rack with compression springs (Amersham, Arlington Heights, Ill.) which securely held the test tubes. The rack was applied to a magnetic plate (Amersham, Arlington Heights, Ill.) and incubated for an additional 10 minutes. The rack was then inverted and the supernatant fluid containing the unbound $^{125}$I-probe was collected in vermiculite and discarded. The ends of the tubes were blotted onto paper towels. The antiserum bound $^{125}$I-probe peptide was "held" to the bottom of the test tube by the magnetic field.

The radioactivity associated with the $^{125}$I-probe was determined in a 10-well Cobra II Auto Gamma Counter (Packard Instruments). The percent binding of probe to antisera ($B/B_o$) in the presence of the competitive unlabeled peptide was determined based on the amount bound in the absence of the competitive unlabeled peptide. The $B/B_o$ as a function of standard peptide concentration was plotted by a 4-parameter algorithm (Immunofit Packard Instruments). The $B/B_o$ of the samples was similarly determined and the concentration of the $A\alpha(Val^{360})$ neoepitope, expressed as pmoles of unlabeled peptide, was determined from the standard curve. Only values falling between 20–80% binding were considered to be valid for calculations.

The standard curve parameters ($EC_{80}$, $EC_{50}$, $EC_{20}$) and the percent binding were recorded for each assay. In addition, 3 quality control standard solutions of the standard peptide (100 µl of 2, 6 and 20 nM) were run in each assay. The quality control standards were required to be within 2 standard deviations of mean of the initial 5 assays to be considered valid.

EXAMPLE 18

Gel Electrophoresis and Western Immunoblots
A. Sample and Standard Preparation

Samples of plasma or synovial fluids were diluted 1:10 with PBS and then 1:1 with 2X sample buffer containing 2% mecaptoethanol (NOVEX LC2676) and boiled for 5 minutes. Kaleidoscope prestained standards (Bio-Rad 161-0324) (10 ml/well) were used as received, without reduction, for alkaline phosphatase detection. For enhanced chemiluminescence (ECL) detection, biotininylated SDS-PAGE molecular weight standards (Broad Range Bio-Rad 161-0319) were diluted 1:100 in PBS, then 1:1 into 2X sample buffer and boiled for 5 minutes. Standards (10 µl), plasma and synovial fluid samples (10–30 µl) were routinely analyzed.

B. SDS-PAGE and Transfer Conditions

Gel electrophoresis analyses were performed using 10-lane 1 mm Tris-Glycine 4–20% gradient gels (NOVEX EC6025), Tris-glycine SDS running buffer (NOVEX 2675) in the NOVEX mini-gel system. Each well was flushed with running buffer to remove any unpolymerized acrylamide. The system was assembled and run at 4° C. for 7 minutes at a potential of 100 V and then increased to 200 V for approximately 1 hour or until the sample dye-front was observed to be close to the bottom of the gel.

The gels were equilibrated for 30 minutes with Trisglycine buffer (BioRad 161-0734) and the components electrophoretically transfered onto nitrocellulose membranes (NOVEX LC2001) using the BioRad Mini Trans-Blot system as described by the manufacture. A potential of 105 V was applied for about 55 minutes or until the unit became slightly warm. The nitrocellulose membrane was placed into distilled water for a few minutes then dried and stored for subsequent immuno-blocking.

The membrane(s) were blocked for 30 minutes with 3% non-fat dried milk solution (Sigma M-7409) and then washed once in PBS containing 0.05% Tween-20 (Bio-Rad 170–6531) (PBS-T) for 10 minutes. The membrane was then incubated for 1 hour with R-770 (diluted 1:10,000 in PBS-T). The membrane was then washed 3 times for 10 minutes each with PBS-T.

C. Detection with Alkaline Phosphatase

For visualization with alkaline phosphatase, the membrane was incubated for 1 hour with anti-rabbit IgG-alkaline phosphatase conjugate (diluted 1:1,000 in PBS-T) (Sigma A-0407). The membrane(s) were then washed (3 times for 10 minutes each) with PBS alone (no Tween) and then added to the substrate solution of BCIP-NBT (Sigma B5655) prepared as described by the manufacturer (2 tablets/20 ml $H_2O$). After maximal color development, usually within 10 minutes, the reaction was stopped by removing the membrane to a container of 4 mM EDTA in PBS.

D. Detection with Enhanced Chemiluminescence

For detection by the enhanced chemiluminescence system (ECL) (Amersham RPN 2108) the membrane was incubated with anti-rabbit IgG peroxidase conjugate (Sigma A-4914) diluted 1:1,000 in PBS-T in combination with ExtrAvidin peroxidase (Sigma E-2886) diluted 1:5,000 to visualize the biotinylated standards.

After 1 hour the membrane was washed with PBS-T for 15 minutes followed by 2 additional 5 minute washes. The membrane was incubated for 1 minute with the 2 components of the ECL system (Amersham RPN 2108) as described by the manufacturer. The membrane was wrapped with plastic wrap and placed into a film cassette. Hyperfilm ECL film (Amersham, RPN 2114) was exposed from 10 seconds to 1 minute and developed by conventional procedures.

E. Digestion of Fibrinogen by Various Proteinases

Fibrinogen (Sigma Lot 117F9451) was incubated at 37° C. with various serine proteinases including PMNE, PR3, plasmin, trypsin and porcine pancreatic elastase as well as with the cysteine proteinases cathepsins B, H and L at an enzyme to substrate ratio of 1:500. After 30 minutes, PMNE and PR3 activity were terminated with the monocyclic betalactam PMNE inhibitor L-680,833 (50 µM) and trypsin and porcine pancreatic elastase by PMSF (50 µM). The thiol proteinases cathepsins B, H and L were inactivated by boiling for 5 min. The amount of $A\alpha(Val^{360})$ formed was determined by RIA or visualized by Western immunoblots using alkaline phosphatase detection.

F. Blood Collection

Blood was obtained by antecubital venipuncture or from the radial artery from informed adult volunteers and collected into heparin (Elkins-Sinn Inc #6505-00-153-9740), 10 units/ml. The blood was immediately mixed by inverting the tube 5 times and then placed onto a slowly rocking platform at room temperature. All experiments utilizing A23187 stimulation of blood were started within 2 hours from the time of collection.

G. Plasma Preparation

Heparinized blood (2 ml) was centrifuged at 5° C. at 1800xg for 10 min in a Beckman GS6R centrifuge. Plasma (700 µl) was removed and added to 100 µl of 250 mM EDTA and frozen (final EDTA concentration=31 mM).

H. Synovial Fluid Collection

Synovial fluids from patients with a variety of joint diseases were collected without anticoagulant or with heparin. All samples were centrifuged and the supernatant fluids removed, frozen and stored at −70° C. In preparation for the Aα(Val$^{360}$) analysis, the fluids were thawed and 50 μl of 250 mM EDTA added to 350 μl of the sample. The EDTA was included to inhibit endogenous proteinases which can destroy the $^{125}$I-probe peptide.

I. Calcium Ionophore A23187-Stimulated Formation of Aα(Val$^{360}$) in Human Blood Heparinized blood, 1 ml aliquots, was incubated at 37° C. with 150 μM A23187 (CalbioChem #100105), dimethylsulfoxide (DMSO) control solvent and spike recovery fibrinogen digest (FD) prepared as described below. A stock 75 mM solution of A23187 was prepared in DMSO. The A23187 solution (2 μl of a 75 mM in DMSO), 2 μl DMSO and 23.7 pmoles of fibrinogen digest (FD) were added to empty 2.0 ml polypropylene micro-tubes (Sarstedt #72.608) prior to the addition of 1 ml of blood. The 2 ml additions were performed with P2 or P10 Gilson Pipetman (Ranin Instruments) or with "dedicated" Hamilton syringes. The 1 ml blood additions were done with an Eppendorf repeater (Brinkmann 2226-0006) fitted with 12.5 ml Eppendorf Combitips (Brinkmann 2226-1401). After 1 hour the samples were centrifuged in a 5° C. refrigerated centrifuge (Beckman) for 10 minutes at 2800 rpm. Plasma aliquots (350 μl) were added to 50 μl of 250 mM EDTA to achieve a final EDTA concentration of 31 mM. The samples were frozen and stored at −70° C. prior to RIA analysis.

J. Preparation of Aα(Val$^{360}$) Fibrinopeptide Recovery Standard

A spike recovery standard was prepared to evaluate the stability of Aα(Val$^{360}$) neoepitope in various biological fluids and to monitor recovery throughout sample processing. Human fibrinogen (Sigma Lot 53H9320) (4,500 pmoles) was incubated at 37° C. with 18 pmoles of human PMNE (substrate:enzyme ratio of 250:1) for 60 minutes. The reaction was terminated by the addition of 200 nM α$_1$PI (Athens Research and Technology). The material was aliquoted into 100 ml fractions, frozen and stored at −70° C. The concentration of PMNE generated Aα(Val$^{360}$) neoepitope was determined by RIA. The material contained essentially a single immunoreactive 42 kDa species [the predicted MW of fibrinogen Aα(1–360)] reacting with the R-770 antisera, when analyzed by Western blots.

EXAMPLE 19

Development of an RIA for Aα(Val$^{360}$)

A. Generation of Antiserum

The ultimate goal of this study was to establish a direct RIA to measure the PMNE generated fibrinopeptide neoepitope Aα(Val$^{360}$). It was necessary that the antiserum should not cross react with intact fibrinogen. Also, it was important to establish which other proteinase, if any, generated this neoepitope. In order to achieve such specificity, the antiserum should recognize the free carboxy group of Val$^{360}$ which is normally in an amide linkage with Ser$^{361}$. To raise such an antiserum, C(Nle)T$^{355}$SESSV$^{360}$ (SEQ. ID. NO.:43) was conjugated to thyroglobulin using the cross-linking reagent Sulfo-MBS, which specifically orients the carboxy group of Val$^{360}$ away from the thyroglobulin. The degree of peptide substitution on thyroglobulin was found to be approximately 25 moles of peptide per mole of thyroglobulin. Typically, it was necessary to incorporate at least 20 moles of a short peptide onto a carrier protein to elicit a significant antibody response in either rabbits or in guinea pigs. This conjugate was then injected into rabbits.

B. Sensitivity and Reproducibility of the Assay

A number of rabbit antisera were generated and a RIA was established using an antiserum, termed R-770, at a final dilution of 1:18,000. This RIA detected the peptide antigen Y$^{348}$RGSAGHWTSESSV$^{360}$ (SEQ. ID. NO.:1) with a detection limit of 1.7 nM at 80% bound and 6.6 nM for 50% bound (FIG. 2). Three quality control standards are included in each assay (100 μl of 2, 6, and 20 nM standard peptide) to assess the day-to-day variability of the assay procedure. For a valid assay, the three quality control standards must be within two standard deviations of the mean of the first five assays (FIG. 3). This RIA possessed an inter-assay variation of 11% (N=5) with one plasma sample assayed on 5 different days giving a value of 5.1±0.5 nM. An intra-assay variation of 13% (N=12) with one plasma sample yielding a value of 5.4±0.7 nM when assayed in dodecaduplicate.

C. Specificity of the Antibody

The anti-TSESSV (SEQ. ID. NO.:59) antiserum, R-770, possessed remarkable specificity for the free carboxy group of Val$^{360}$. When the C-terminal Val was truncated from the sequence to generate the peptide AGHWTSESS$^{359}$(SEQ. ID. NO.:60), there was no recognition by the antiserum (FIG. 4). Additional C-terminal truncation peptides were prepared including AGHWTSES(SEQ. ID. NO.:61)$^{358}$, AGHWTSE(SEQ. ID. NO.:62)$^{357}$, AGHWTS(SEQ. ID. NO.:63)$^{356}$, and AGHWT(SEQ. ID. NO.:60)$^{355}$. None of these peptides were recognized by the antiserum at concentrations up to 100 μM, confirming the requirement for the carboxy-terminal Val. A series of peptides were also prepared that extended across the PMNE cleavage site to determine if fibrinogen fragments that might be generated by cleavage distal to the Val$^{360}$ terminal site would be recognized by the anti-TSESSV antiserum (FIG. 5). There is greater than a 300 fold loss in recognition by R-770 with the peptides AGHWTSESSVS$^{361}$, AGHWTSESSVSG$^{362}$(SEQ. ID. NO.:65), AGHWTSESSVSGS$^{363}$(SEQ. ID. NO.:66), AGHWTSESSVSGST$^{364}$(SEQ. ID. NO.:67), and AGHWTSESSVSGSTG$^{365}$(SEQ. ID. NO.:68), again confirming the requirement of the valine carboxyl group for recognition by R-770.

A series of peptides were synthesized to characterize the length of the peptide required for maximal recognition by the antiserum. When the sequence WTSESSV$^{360}$ (SEQ. ID. NO.:5)was shortened by one, two, three, or four amino acids to TSESSV(SEQ. ID. NO.:59), SESSV(SEQ. ID. NO.:60), ESSV(SEQ. ID. NO.:16), and SSV(SEQ. ID. NO.:16), there was 10, 50, 70, and 300-fold loss in recognition, respectively (FIG. 6). Therefore, $^{354}$WTSESSV$^{360}$ (SEQ. ID. NO.:5) was determined to be the minimum sequence required for optimal recognition by the antiserum. Additional C-terminal substitution data are presented in FIG. 7. The amidation of the ValCOOH to ValCONH$_2$ as well as the substitution of D-Val for the L-Val also resulted in a marked loss of recognition by the antisera. Replacement of Val with Thr or Ile resulted in a 10–100-fold loss of recognition. The replacement of Val with Leu resulted in a complete loss of recognition.

FIG. 8 shows that a commercial preparation of human fibrinogen gave a 50% displacement in the RIA at 2 μM. This slight cross-reactivity (0.1%) was immunoadsorbed with the anti-TSESSV(SEQ. ID. NO.:59) antiserum R-770. These data suggested that the Aα(Val$^{360}$) neoepitope was present in the commercial fibrinogen preparation and that R-770 does not detect intact human fibrinogen at concentrations normally found in human plasma. Additionally, Western-blot analysis data of commercial human fibrinogen confirmed the presence of a 42 kDa component, which is consistent with the predicted MW for the Aα(Val$^{360}$)(SEQ. ID. NO.:1) neoepitope fragment. This signal was blocked by the standard peptide YRGSAGHWTSESSV$^{360}$, but not by the spanning peptide AGHWTESSV$^{360}$SGST(SEQ. ID. NO.:70). The Aα(Val$^{360}$) signal was not detected with preimmune serum (FIG. 9).

D. Time-dependent Production of Aα(Val$^{360}$) by PMNE and PR3 but not by Other Proteinases In order to determine the selectivity of PMNE to produce the Aα(Val$^{360}$) neoepitope, a series of proteinases were analyzed for their ability to hydrolyze fibrinogen at the Val$^{360}$–Ser$^{361}$ site. PMNE, incubated at an enzyme to substrate ratio of 1:250, hydrolyzed fibrinogen to form Aα(Val$^{360}$) neoepitope in a time dependent manner (FIG. 10).

Proteinase 3 (PR3) is a serine proteinase with 54% sequence homology to PMNE. It is also localized in the azurophilic granule of PMN. The incubation of fibrinogen with PR3 resulted in the time-dependent formation of Aα(Val$^{360}$) forming the neoepitope at approximately 15% of the PME catalyzed rate (FIG. 11).

Fibrinogen was incubated at 37° C. with PMNE, PR3 and other proteinases at 37° C. at enzyme:substrate of 1:500 and analyzed by Western-blot (FIG. 12). An intense immunoreactive component at 42 kDa was formed by PMNE and PR3. The human serine proteinases (plasmin and trypsin) showed no additional immunostaining over the endogenous Aα (Val$^{360}$) present in the fibrinogen substrate. Likewise, the cysteine proteinases (cathepsins B, H and L) did not form the neoepitope. However, porcine pancreatic elastase showed a moderate Aα(Val$^{360}$) signal.

E. Human Plasma Degrades the $^{125}$I-Probe Peptide

In order to validate the assay for use with biological fluids, the stability of the $^{125}$I-probe ($^{125}$I-YRGSAGHATSESSV) (SEQ. ID. NO.:9)in human plasma was investigated (FIG. 13). The incubation of the RP-HPLC purified probe with 100 μl of human plasma for 30 minutes at 37° C. resulted in the breakdown of the $^{125}$I-probe into at least 2 new radiolabeled species as determined by subsequent HPLC analysis (FIG. 13). The inclusion of EDTA (31 mM) in the incubation mixture prevented this breakdown (FIG. 13). Similarly to plasma, EDTA prevented the breakdown of the $^{125}$I-probe in incubations of various synovial fluid samples. These findings support the idea that an EDTA sensitive proteinase, such as carboxypeptidase, may remove the C-terminal Val residue from the $^{125}$I-probe peptide and thus inhibit binding. Decreased antibody binding of the $^{125}$I-probe peptide would appear as an artifactual positive signal in the RIA, increasing the detected neoepitope concentration above its true value.

A spike recovery standard was prepared to evaluate the stability of Aα(Val$^{360}$) in biological fluids and assess recovery throughout the sample processing protocol. A limited digest of fibrinogen (FD) was prepared using a 1:500 ratio of PMNE:fibrinogen incubated for 30 minutes at 37° C. Western immunoblot analysis showed the digest contained predominantly one inumuno-reactive fragment of approximately 42 kDa (FIG. 14). The concentration of Aα(Val$^{360}$) in the FD, as determined by RIA, was 0.97 μM. Aliquots (10 μl containing 9.7 pmoles), were added to duplicate biologic samples (ie. blood or synovial fluid) to determine recovery and stability of the Aα(Val$^{360}$) neoepitope during the RIA analysis.

Excellent recoveries of the limited fibrinogen digest were found in incubations with human blood (Table 1). When blood was incubated with Aα(Val$^{360}$) FD and 31 mM EDTA for one hour, the recovery of Aα(Val$^{360}$) FD in the plasma was 99% versus 108% when blood was incubated with FD alone. The plasma concentration of FD was corrected for the individual donor's hematocrit. However, in the absence of EDTA, it was not possible to recover the standard peptide from blood (Table 1). In the presence of 31 mM EDTA, a partial recovery (69%) was achieved. These data are consistent with the idea that EDTA protects the $^{125}$I-probe peptide from inactivation due to proteolysis by carboxypeptidase(s).

F. Identification of Aα(Val$^{360}$) Neoepitope in Control Human Plasma

RIA analysis of normal human plasma detected an endogenous Aα(Val$^{360}$) neoepitope in both arterial blood collected into heparin of 6.1±1.1 nM (Mean±SD, N=10) and venous blood collected into heparin of 4.2±1.5 nM (Mean±SD, N=13) (Table 2). Normal human plasma concentration of fibrinogen ranges from 4 to 8 μM. Therefore, the amount of the Aα(Val$^{360}$) neoepitope is approximately 0.1% of the total fibrinogen pool. This is identical to the amount of Aα(Val$^{360}$) detected in commercial preparations of fibrinogen (FIG. 8). The Aα(Val$^{360}$) neoepitope in plasma containing 31 mM EDTA was stable to 5 repetitive freeze/thaw cycles over a 7 day period. The mean value of 5 repetitive freeze/thaws was 5.1±0.5 nM Aα(Val$^{360}$) (Mean±SD).

The existence of the endogenous plasma Aα(Val$^{360}$) fragment was further confirmed by Western immunoblots. An Aα(Val$^{360}$) immunoreactive band migrating at 42 kDa was detected in plasma from 2 normal donors when visualized by enhanced chemiluminescence (FIG. 15) This signal was partially blocked by the addition of the standard peptide YRGSAGHWTSESSV(SEQ. ID. NO.:1) (10 μM) to the R-770 antibody solution. These data are the first direct demonstration of PMNE activity in healthy individuals.

G. Production of Aα(Val$^{360}$) in Human Blood Stimulated by A23187 and its Inhibition by L-694,458

FIG. 16 demonstrated the time-dependent production of Aα(Val$^{360}$) peptide in human blood stimulated with the calcium ionophore A23187 (150 μM). The maximal amount of Aα(Val$^{360}$) peptide was produced by within 30–60 minutes. Aα(Val$^{360}$) production measured by RIA was confirmed by Western blot analysis of increasing amounts of a 42 kDa peptide. Other stimuli such as zymosan and phorbol myristate acetate also gave similar results. These findings demonstrated that the cleavage of an endogenous substrate by PMNE released from PMN occurs in blood in the presence of large concentrations of the natural inhibitors α$_1$PI and α$_2$-macroglobulin. FIG. 17 displayed the concentration dependence of the calcium ionophore A23187 to form Aα(Val$^{360}$) in human blood incubated at 37° C. for 60 minutes. Maximal Aα(Val$^{360}$) peptide formation was achieved with an A23187 concentration of approximately 75 μM. This concentration of A23187 did not cause release of lactic dehydrogenase, suggesting that PMNE was released by exocyotosis in the milieu of whole blood. Routinely, 150 μM of A23187 was used in this ex vivo blood assay.

The extent of Aα(Val$^{360}$) formation was studied in blood from different individuals. Aliquots of blood from each donor were incubated with DMSO or A23187 and the amount of Aα(Val$^{360}$) formed was measured by RIA (Table 3). The plasma Aα(Val$^{360}$) concentration in the DMSO treated blood was 4.5±1.2 nM, ranging from 2.9 to 6.9 nM. The plasma concentration of Aα(Val$^{360}$) in blood incubated with A231287 was 33.9±15.1 nM, ranging from 16.8 to 66.1 nM. After normalizing the Aα(Val$^{360}$) values for the number of PMN in a blood sample, DMSO treated blood contained 1.5±0.5 pmoles Aα(Val$^{360}$)/1×10$^6$ PMN and 11.0±3.7 pmoles Aα(Val$^{360}$)/1×10$^6$ PMN was present in blood stimulated with A23187 (Table 3). In these experiments the recovery of the fibrinogen digest was 100±21%.

FIG. 18 demonstrated that the PMNE inhibitor L-694,458 blocked Aα(Val$^{360}$) peptide formation in the calcium ionophore blood assay in a concentration-dependent fashion with an EC$_{50}$ of 0.3 μM; complete inhibition was achieved at about 1 μM. Normal human blood contains approximately 0.3 μM PMNE. Thus maximal inhibition of Aα(Val$^{360}$) was achieved with amounts of L-694,458 which were only 3–5 times the molar excess over the total amount of PMNE present in this system. This indicates the great tropism of L-694,458 for PMNE in PMN, bearing in mind that the enzyme is present in a compartment within PMN that represents only a fraction of a percent of the total blood volume. Clearly, this ex vivo stimulation of human blood by A23187 to produce Aα(Val$^{360}$) peptide could be used to monitor the biochemical efficacy of L-694,458 following the oral administration of the drug in man.

H. Identification of Elevated Levels of Aα(Val$^{360}$) in Cystic Fibrosis Plasma Compared with Control Plasma It is well documented that PMN accumulate at sites of inflammation in diseases of acute onset or in acute exacerbations of chronic inflammatory diseases. This accumulation of PMN is associated with the release of PMNE into the circulation as detected by increased levels of α$_1$PI-PMNE complexes or of free enzyme in excess of natural inhibitors in the large airways in diseases such as cystic fibrosis and bronchitis. It has been difficult up to now to provide direct evidence for the activity of PMNE released during inflammation as opposed to its presence as a complex with α$_1$PI.

Plasma samples from 25 patients with cystic fibrosis and from 5 normal individuals were analyzed for Aα(Val$^{360}$) obtained from Children's Hospital, Boston, Mass. FIG. 19 showed a clear elevation of Aα(Val$^{360}$) in the plasma of cystic fibrosis patients indicative of PMNE activity. The increases in Aα(Val$^{360}$), up to 100-fold above normal, correlated closely with increased α$_1$PI:PMNE levels (R=0.99). These data are the first direct demonstration of elevated PMNE activity in disease. This assay should provide a precise indicator of the inhibition of increased PMNE activity present in the cystic fibrotic lung following drug treatment.

I. Identification of Aα(Val$^{360}$) Neoepitope in Synovial Fluids from Rheumatoid Arthritis and Gout Patients The presence of Aα(Val$^{360}$) neoepitope was evaluated in other inflammatory diseases chararacterized by PMN infiltration. Elevated PMN levels are found in synovial fluid from patients with rhematoid arthritis and gout. In contrast, joint fluids from osteoarthritis patients have few, if any, PMN and less fluid accumulation. A series of synovial fluids from various joint diseases were evaluated for the Aα(Val$^{360}$) neoepitope (Table 4). All 17 samples from RA patients contained Aα(Val$^{360}$), with values ranging from ranging from 7–88 nM. Four out of 5 samples from patients with gout also contained the Aα(Val$^{360}$) neoepitope. In contrast, Aα(Val$^{360}$) was not found in synovial fluids from 4 osteoarthritis patients. The Aα(Val$^{360}$) neoepitope was also present in synovial fluids from patients with pseudogout and psoriatic arthritis. In contrast to plasma where the molecular weight of the Aα(Val$^{360}$) neoepitope is 42 kDa, the molecular weight of the redominant neoepitope in synovial fluid from both RA and gout patients was approximately 20 kDa, with smaller amounts of the 42 kDa component observed in some, but not all samples (FIG. 20). This finding indicated that other proteinases, possible including PMNE, present in RA and gout synovial fluids may be making an additional cleavage in the fibrinogen molecule. Although the importance of PMNE in joint disease and cartilage erosion is not known, these observations suggest that measurement of Aα(Val$^{360}$) in synovial fluid may be a useful biochemical marker to monitor the effectiveness of an PMNE inhibitor in rheumatoid arthritis.

EXAMPLE 20

General Assay Protocol

The Aα(Val$^{360}$) epitope is one of the C terminus neoepitope peptides and antibodies to them are readily used to measure PMNE-derived fibrinogen cleavage neoeptiopes in biologic samples. Such a method may be described as follows:

a) combining the sample with an anticoagulant to form a mixture;

b) optionally, adding a leukocyte membrane perturbing agent to the mixture to release PMNE from the leukocytes;

c) optionally, incubating the mixture under conditions that permit the cleavage of fibrinogen by PMNE to yield fibrinogen cleavage product neoepitope;

d) optionally, centrifuging the mixture to form a pellet and a neoepitope containing supernatant fluid;

e) collecting the supernatant fluid and adding EDTA (fmal concentration of about 31 mM) to the supernatant fluid to form an EDTA-fluid mixture;

f) mixing an aliquot of the EDTA-fluid mixture with a specific antibody and $^{125}$I-probe solutions;

g) separating antibody-bound probe from unbound probe and measuring the $^{125}$I-probe in the antibody-bound probe fraction; and h) comparing the measurement of step g to a standard.

---

What is claimed is:

1. A method for determining the presence of absence of leukocyte elastase produced fibrinogen cleavage peptides in a sample of a body fluid containing leukocytes and fibrinogen, comprising the following steps:

a) combining the sample with an anticoagulant to form a mixture;

b) centrifuging the mixture to form a pellet and a supernatant;

c) collecting the supernatant;

d) contacting the supernatant with at least one antibody which specifically binds to a leukoce-elastase produced fibrinogen cleavage peptide-specific epitope to form an immunocomplex, wherein said epitope is a termal epitope selected from the group of epitopes consisting of Aα 356–360 residues and Aα 564–568 residues, and wherein siad at least one antibody does not bind uncleaved fibrinogen; and e) determining the presence or absence of an immunocomplex formed as an indication of the presence or absence of ad leukocyte-elastase produced fibrinogen cleavage peptides in the sample.

2. The method of claim 1 further comprising releasing the elastase from the leukocytes by adding a leukocyte membrane perturbating agent to the mixture of step a).

3. A method for evaluating the efficacy of inhibitors of human leukocyte elastase activity comprising:

a) combining a sample of a body fluid of a human patient with an anticoagulant to form a mixture;

b) centrifuging the mixture to form a pellet and a supernatant;

c) collecting the supernatant;

d) contacting the supernatant with at least one antibody which specifically binds to a leukocyte-elastase produced fibrinogen cleavage peptide-specfic epitope to form an immunocomplex, wherein said epitope is a terminal epitope selected from the group of epitopes consisting of Aα 356–360 residues and Aα 564–568 residues, and wherein said at least one antibody does not bind uncleaved fibrinogen; and e) determining the presence or absence of an immunocomplex formed as an indication of human leukocyte-elastase activity in said patient;

f) treating the patient with at least one inhibitor of leukocyte elastase;

g) repeating steps a) through e); and h) evaluating the efficacy of the at least one inhibitor by comparing the measurements of steps e) and g).

4. A method for detecting leukocyte elastase produced fibrinogen cleavage peptides in a sample of a body fluid which contains fibrinogen but which does not contain leukocytes or leukocyte elastase, comprising:

a) adding an anticoagulant and leukocytes or leukocyte elastase to the sample to form a mixture;

b) incubating the mixture, c) centrifuging the mixture to form a pellet and a supernatant;

d) collecting the supernatant;

e) contacting the supernatant with at least one antibody which specifically binds to a leuk elastase produced fibrinogen cleavage peptide-specific epitope to form an immunocomplex, wherein said epitope is a terminal epitope selected from the group of epitopes consisting of Aα 356–360 residues and Aα 564–568 residues, and wherein said at least one antibody does not bind uncleaved fibrinogen; and f) detecting the presence or absence of an immunocomplex formed as an indication of the presence or absence of said leukocyte-elastase produced fibrinogen cleavage peptides in the sample.

5. The method of claim 4, wherein the incubation in step b) is between about 10 minutes and about 40 minutes.

6. The method of claim 4 wherein the incubation is at about 37° C.

7. A competitive radioimmunoassay for determining the presence or absence of leukocyte elastase activity in a sample of a body fluid comprising:

a) combining the sample with an anticoagulant to form a mixture;

b) centrifuging the mixture to form a pellet and a supernatant;

c) collecting the supernatant and adding EDTA to a final concentration of about 31 mM to form an EDTA-supernatant mixture;

d) mixing an aliquot of the EDTA-supernatant mixture with an antibody that specifically binds an epitope directly adjacent to the amino acid or carboxyl terminus of leukocyte-elastase produced fibrinogen Aα $Val^{360}$–$Ser^{361}$ cleavage peptides to form, when the cleavage peptides are present in said sample, an antibody-cleavage product complex, e) contacting the mixture of step d) with a an $^{125}$I-probe that competes with said cleavage peptides and specifically binds to said antibody to form an antibody-$^{125}$I-probe immunocomplex;

f) separating any said antibody-$^{125}$I-probe immunocomplex formed in step e) from unbound probes; and g) measuring said separated antibody-$^{125}$I-probe immunocomplex as an indication of the presence or absence of said leukocyte elastase activity in the sample.

8. The method of claim 7 further comprising adding a leukocyte membrane perturbing agent to the mixture of step a) to release leukocyte elastase from the leukocytes.

* * * * *

SEQUENCE LISTING (1) GENERAL INFORMATION:

(iii) NUMBER OF SEQUENCES: 71

(2) INFORMATION FOR SEQ ID NO:1:

(i) SEQUENCE CHARACTERISTICS:
        (A) LENGTH: 14 amino acids
        (B) TYPE: amino acid
        (C) STRANDEDNESS: single

```
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Tyr Arg Gly Ser Ala Gly His Trp Thr Ser Glu Ser Ser Val
1               5                  10

(2) INFORMATION FOR SEQ ID NO:2:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

Tyr Arg Gly Ser Ala Gly His Ala Thr Ser Glu Ser Ser Val
1               5                  10

(2) INFORMATION FOR SEQ ID NO:3:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

Ala Gly His Trp Thr Ser Glu Ser Ser
1               5

(2) INFORMATION FOR SEQ ID NO:4:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

Ala Gly His Trp Thr Ser Glu Ser Ser Val Ser
```

```
1               5                    10
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

```
Trp Thr Ser Glu Ser Ser Val
1               5
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

```
Asp Phe Leu Ala Glu Gly Gly Gly Val Arg Gly Pro Arg Val Val
1               5                   10                  15
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:7:

```
Ser Glu Arg Gly Ser Ala Gly His Trp Thr Ser Glu Ser Ser Val
1               5                   10                  15
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide

```
        (iii) HYPOTHETICAL: NO (iv) ANTI-SENSE: NO (v) FRAGMENT TYPE: internal (xi) SEQUENCE DESCRIPTION: SEQ ID NO:8:

Thr Thr Thr Arg Arg Ser Cys Ser Lys Thr Val Thr Lys Thr Val
1               5                  10                  15

(2) INFORMATION FOR SEQ ID NO:9:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:9:

Val Ile Gly Pro Asp Gly His Lys Glu Val Thr Lys Glu Val Val
1               5                  10                  15

(2) INFORMATION FOR SEQ ID NO:10:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:10:

Glu Val Val Thr Ser Glu Asp Gly Ser Asp Cys Pro Glu Ala Met
1               5                  10                  15

(2) INFORMATION FOR SEQ ID NO:11:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

Arg Gly Lys Ser Ser Ser Tyr Ser Lys Gln Phe Thr Ser Ser Thr
1               5                  10                  15

(2) INFORMATION FOR SEQ ID NO:12:
```

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

Asp Gly Phe Asp Phe Gly Asp Asp Pro Ser Asp Lys Phe Phe Thr
1               5                   10                  15

(2) INFORMATION FOR SEQ ID NO:13:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

Gly Trp Trp Met Ala Lys Cys His Ala Gly His Leu Asn Gly Val
1               5                   10                  15

(2) INFORMATION FOR SEQ ID NO:14:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:14:

His Leu Asn Gly Val Tyr Tyr Gln Gly Gly Thr Tyr Ser Lys Ala
1               5                   10                  15

(2) INFORMATION FOR SEQ ID NO:15:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

Gly Pro Arg Val Val
1               5

(2) INFORMATION FOR SEQ ID NO:16:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:16:

Ser Glu Ser Ser Val
1               5

(2) INFORMATION FOR SEQ ID NO:17:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:17:

Val Thr Lys Thr Val
1               5

(2) INFORMATION FOR SEQ ID NO:18:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Thr Lys Glu Val Val
1               5

(2) INFORMATION FOR SEQ ID NO:19:

(i) SEQUENCE CHARACTERISTICS:
           (A) LENGTH: 5 amino acids
           (B) TYPE: amino acid (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

Cys Pro Glu Ala Met
1               5

(2) INFORMATION FOR SEQ ID NO:20:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

Phe Thr Ser Ser Thr
1               5

(2) INFORMATION FOR SEQ ID NO:21:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:21:

Asp Lys Phe Phe Thr
1               5

(2) INFORMATION FOR SEQ ID NO:22:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:22:

```
His Leu Asn Gly Val
1               5
```

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:23:

```
Thr Tyr Ser Lys Ala
1               5
```

(2) INFORMATION FOR SEQ ID NO:24:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:24:

```
Glu Arg His Gln Ser Ala Cys Lys Asp Ser Asp Trp Pro Phe Cys
1               5                   10                  15
```

(2) INFORMATION FOR SEQ ID NO:25:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:25:

```
Ser Gly Ser Thr Gly Gln Trp His Ser Glu Ser Gly Ser Phe Arg
1               5                   10                  15
```

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide -continued (iii) HYPOTHETICAL: NO (iv) ANTI-SENSE: NO (v) FRAGMENT TYPE: internal (xi) SEQUENCE DESCRIPTION: SEQ ID NO:26:

```
Ile Gly Pro Asp Gly His Lys Glu Val Thr Lys Glu Val Val Thr
1               5                   10                  15
```

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:27:

```
Thr Ser Glu Asp Gly Ser Asp Cys Pro Glu Ala Met Asp Leu Gly
1               5                   10                  15
```

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:28:

```
Asp Leu Gly Thr Leu Ser Gly Ile Gly Thr Leu Asp Gly Phe Arg
1               5                   10                  15
```

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:29:

```
Ser His Asn Gly Met Gln Phe Ser Thr Trp Asp Asn Asp Asn Asn
1               5                   10                  15
```

(2) INFORMATION FOR SEQ ID NO:30:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:30:

Ser His Asn Gly Met Gln Phe Ser Thr Trp Asp Asn Asp Asn Asn
1               5                   10                  15

(2) INFORMATION FOR SEQ ID NO:31:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:31:

Tyr Tyr Gln Gly Gly Thr Tyr Ser Lys Ala Ser Thr Pro Asn Gly
1               5                   10                  15

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:32:

Ser Thr Pro Asn Gly Tyr Asp Asn Gly Ile Ile Trp Ala Thr Trp
1               5                   10                  15

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:33:

Glu Arg His Gln Ser
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:34:

Ser Gly Ser Thr Gly
1               5

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:35:

Ile Gly Pro Asp Gly
1               5

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:36:

Thr Ser Glu Asp Gly
1               5

(2) INFORMATION FOR SEQ ID NO:37:

(i) SEQUENCE CHARACTERISTICS:
        (A) LENGTH: 5 amino acids (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:37:

Asp Leu Gly Thr Leu
1               5

(2) INFORMATION FOR SEQ ID NO:38:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:38:

Ser Tyr Asn Arg Gly
1               5

(2) INFORMATION FOR SEQ ID NO:39:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:39:

Ser His Asn Gly Met
1               5

(2) INFORMATION FOR SEQ ID NO:40:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:40:

```
Tyr Tyr Gln Gly Gly
1               5
```

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:41:

```
Ser Thr Pro Asn Gly
1               5
```

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Modified-site
        (B) LOCATION: 2..3
        (D) OTHER INFORMATION: /product= "Xaa is Nle"

(xi) SEQUENCE DESCRIPTION: SEQ ID NO:42:

```
Cys Xaa Gly Pro Arg Val Val
1               5
```

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Modified-site
        (B) LOCATION: 2..3
        (D) OTHER INFORMATION: /product= "Xaa is Nle"

(xi) SEQUENCE DESCRIPTION: SEQ ID NO:43:

```
Cys Xaa Thr Ser Glu Ser Ser Val
1               5
```

(2) INFORMATION FOR SEQ ID NO:44:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:44:

```
Tyr Ala Asp Ser Gly Glu Gly Asp Phe Leu Ala Glu Gly Gly Gly Val
1               5                   10                  15

Arg Gly Pro Arg Val Val
            20
```

(2) INFORMATION FOR SEQ ID NO:45:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:45:

```
Ala Asp Ser Gly Glu Gly Asp Phe Leu Ala Glu Gly Gly Gly Val Arg
1               5                   10                  15

Gly Pro Arg Val Val
            20
```

(2) INFORMATION FOR SEQ ID NO:46:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:46:

```
Glu Gly Asp Phe Leu Ala Glu Gly Gly Gly Val Arg Gly Pro Arg Val
1               5                   10                  15

Val
```

(2) INFORMATION FOR SEQ ID NO:47:

(i) SEQUENCE CHARACTERISTICS:

```
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:47:

Leu Ala Glu Gly Gly Gly Val Arg Gly Pro Arg Val Val
1               5                  10

(2) INFORMATION FOR SEQ ID NO:48:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:48:

Gly Gly Gly Val Arg Gly Pro Arg Val Val
1               5                  10

(2) INFORMATION FOR SEQ ID NO:49:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:49:

Gly Val Arg Gly Pro Arg Val Val
1               5

(2) INFORMATION FOR SEQ ID NO:50:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal
```

(xi) SEQUENCE DESCRIPTION: SEQ ID NO:50:

Val Arg Gly Pro Pro Val Val
1               5

(2) INFORMATION FOR SEQ ID NO:51:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:51:

Gly Pro Arg Val Val
1               5

(2) INFORMATION FOR SEQ ID NO:52:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:52:

Ala Asp Ser Gly Glu Gly Asp Phe Leu Ala Glu Gly Gly Gly Val Arg
1               5                   10                  15

Gly Pro Arg Val Val Glu
            20

(2) INFORMATION FOR SEQ ID NO:53:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:53:

Ala Asp Ser Gly Glu Gly Asp Phe Leu Ala Glu Gly Gly Gly Val Arg
1               5                   10                  15

Gly Pro Arg Val
            20

(2) INFORMATION FOR SEQ ID NO:54:

```
        (i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:54:

Ala Asp Ser Gly Glu Gly Asp Phe Leu Ala Glu Gly Gly Gly Val Arg
1               5                   10                  15

Gly Pro Arg (2) INFORMATION FOR SEQ ID NO:55:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:55:

Ala Asp Ser Gly Glu Gly Asp Phe Leu Ala Glu Gly Gly Gly Val Arg
1               5                   10                  15

Gly Pro (2) INFORMATION FOR SEQ ID NO:56:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:56:

Ala Asp Ser Gly Glu Gly Asp Phe Leu Ala Glu Gly Gly Gly Val Arg
1               5                   10                  15

(2) INFORMATION FOR SEQ ID NO:57:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide
```

(iii) HYPOTHETICAL: NO (iv) ANTI-SENSE: NO (v) FRAGMENT TYPE: internal (xi) SEQUENCE DESCRIPTION: SEQ ID NO:57:

Gly Pro Arg Val Val
1               5

(2) INFORMATION FOR SEQ ID NO:58:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
             (A) NAME/KEY: Modified-site
             (B) LOCATION: 2..3
             (D) OTHER INFORMATION: /product= "Xaa is Nle"

(xi) SEQUENCE DESCRIPTION: SEQ ID NO:58:

Cys Xaa Thr Ser Glu Ser Ser Val
1               5

(2) INFORMATION FOR SEQ ID NO:59:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:59:

Thr Ser Glu Ser Ser Val
1               5

(2) INFORMATION FOR SEQ ID NO:60:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:60:

```
Ala Gly His Trp Thr Ser Glu Ser Ser
1               5
```

(2) INFORMATION FOR SEQ ID NO:61:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:61:

```
Ala Gly His Trp Thr Ser Glu Ser
1               5
```

(2) INFORMATION FOR SEQ ID NO:62:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

```
Ala Gly His Trp Thr Ser Glu
1               5
```

(2) INFORMATION FOR SEQ ID NO:63:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:63:

```
Ala Gly His Trp Thr Ser
1               5
```

(2) INFORMATION FOR SEQ ID NO:64:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide -continued

```
        (iii) HYPOTHETICAL: NO (iv) ANTI-SENSE: NO (v) FRAGMENT TYPE: internal (xi) SEQUENCE DESCRIPTION: SEQ ID NO:64:

Ala Gly His Trp Thr
1               5

(2) INFORMATION FOR SEQ ID NO:65:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:65:

Ala Gly His Trp Thr Ser Glu Ser Ser Val Ser Gly
1               5                   10

(2) INFORMATION FOR SEQ ID NO:66:

(i) SEQUENCE CHARACTERISTICS:
              (A) LENGTH: 13 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:66:

Ala Gly His Trp Thr Ser Glu Ser Ser Val Ser Gly Ser
1               5                   10

(2) INFORMATION FOR SEQ ID NO:67:

(i) SEQUENCE CHARACTERISTICS:
              (A) LENGTH: 14 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:67:

Ala Gly His Trp Thr Ser Glu Ser Ser Val Ser Gly Ser Thr
1               5                   10
```

(2) INFORMATION FOR SEQ ID NO:68:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:68:

```
Ala Gly His Trp Thr Ser Glu Ser Ser Val Ser Gly Ser Thr Gly
 1               5                  10                  15
```

(2) INFORMATION FOR SEQ ID NO:69:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:69:

```
Ser Glu Ser Ser Val
 1               5
```

(2) INFORMATION FOR SEQ ID NO:70:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:70:

```
Ala Gly His Trp Thr Glu Ser Ser Val Ser Gly Ser Thr
 1               5                  10
```

(2) INFORMATION FOR SEQ ID NO:71:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO

```
    (v) FRAGMENT TYPE: internal (xi) SEQUENCE DESCRIPTION: SEQ ID NO:71:

Phe Thr Ser Ser Thr
1               5
```